US012319930B2

(12) United States Patent
Haddad et al.

(10) Patent No.: US 12,319,930 B2
(45) Date of Patent: Jun. 3, 2025

(54) CELL SPECIFIC TRANSCRIPTIONAL REGULATORY SEQUENCES AND USES THEREOF

(71) Applicant: VALORISATION-HSJ, LIMITED PARTNERSHIP, Montréal (CA)

(72) Inventors: Élie Haddad, Hampstead (CA); Panojot Bifsha, Montréal (CA); Aurélien Colamartino, Montréal (CA); Kathie Béland, Montréal (CA)

(73) Assignee: VALORISATION HSJ, LIMITED PARTNERSHIP, Quebec (CA)

( * ) Notice: Subject to any disclaimer, the term of this patent is extended or adjusted under 35 U.S.C. 154(b) by 932 days.

(21) Appl. No.: 17/310,107

(22) PCT Filed: Jan. 24, 2020

(86) PCT No.: PCT/CA2020/050084
§ 371 (c)(1),
(2) Date: Jul. 16, 2021

(87) PCT Pub. No.: WO2020/150832
PCT Pub. Date: Jul. 30, 2020

(65) Prior Publication Data
US 2022/0042041 A1 Feb. 10, 2022

Related U.S. Application Data

(60) Provisional application No. 62/796,254, filed on Jan. 24, 2019.

(51) Int. Cl.
| | |
|---|---|
| *C12N 15/63* | (2006.01) |
| *A61K 40/11* | (2025.01) |
| *A61K 40/31* | (2025.01) |
| *A61K 40/42* | (2025.01) |
| *C07K 14/725* | (2006.01) |
| *C12N 5/0781* | (2010.01) |
| *C12N 5/0783* | (2010.01) |
| *C12N 15/86* | (2006.01) |

(52) U.S. Cl.
CPC .............. *C12N 15/86* (2013.01); *A61K 40/11* (2025.01); *A61K 40/31* (2025.01); *A61K 40/421* (2025.01); *A61K 40/4212* (2025.01); *A61K 40/4258* (2025.01); *C07K 14/7051* (2013.01); *C12N 5/0635* (2013.01); *C12N 5/0636* (2013.01); *C12N 5/0646* (2013.01); *A61K 2239/47* (2023.05); *A61K 2239/48* (2023.05); *C12N 2740/15043* (2013.01); *C12N 2830/15* (2013.01)

(58) Field of Classification Search
None
See application file for complete search history.

(56) References Cited

U.S. PATENT DOCUMENTS

2008/0279870 A1  11/2008  Inghirami et al.

FOREIGN PATENT DOCUMENTS

| EP | 2518153 A1 | 10/2012 |
|---|---|---|
| WO | 2017/066172 A1 | 4/2017 |
| WO | 2018/213786 A1 | 11/2018 |

OTHER PUBLICATIONS

Jenks, Trends in Comparative Endocrinology and Neurobiology, 2009. Ann. N. Y. Acad. Sci. vol. 1163, pp. 17-30 (Year: 2009).*
Dickmeis, Briefings in Functional Genomics and Proteomics, 2005. vol. 3, No. 4, pp. 332-350, see p. 341, 2nd col. lines 1-3 (Year: 2005).*
Wang et al. (Nucleic Acids Research, 2009. vol. 37, No. 8, pp. 2618-2629) (Year: 2009).*
Poole et al. (Gene, 2001. vol. 269, pp. 1-12) (Year: 2001).*
Andersson et al., "An atlas of active enhancers across human cell types and tissues", Nature 507: 455-461 (2014).
Barolo, "How to tune an enhancer", PPNAS, vol. 113, 23:6330-6331 (2016).
Boshart et al., "A Very Strong Enhancer Is Located Upstream of an Immediate Early Gene of Human Cytomegalovirus", Cell, 41:521-530 (1985).
Cico et al., "Enhancers and their dynamics during hematopoietic differentiation and emerging strategies for therapeutic action", FEBS Letters, 590:4084-4104 (2016).
Dion et al., "HIV Infection Rapidly Induces and Maintains a Substantial Suppression of Thymocyte Proliferation", Immunity, 21:757-768 (2004).
Dronadula et al., "Construction of a novel expression cassette for increasing transgene expression in vivo in endothelial cells of large blood vessels", Gene Therapy, 18:501-508 (2011).
Ede et al., "Quantitative Analyses of Core Promoters Enable Precise Engineering of Regulated Gene Expression in Mammalian Cells", ACS Synth Biol., 5:395-404 (2016).
Fitzgerald et al., "Cytokine Release Syndrome After Chimeric Antigen Receptor T Cell Therapy for Acute Lymphoblastic Leukemia", Crit Care Med, 45(2): e124-e131 (2017).
Girard-Gagnepain et al., "Baboon envelope pseudotyped LVs outperform VSV-G-LVs for gene transfer into early-cytokine-stimulated and resting HSCs", Blood, 124(8):1221-1231 (2014).
Grupp et al., "Chimeric Antigen Receptor-Modified T Cells for Acute Lymphoid Leukemia", N Engl J Med, 368: 1509-1518 (2013).

(Continued)

*Primary Examiner* — Celine X Qian
(74) *Attorney, Agent, or Firm* — Lavery, de Billy, L.L.P.; Alain Dumont

(57) ABSTRACT

New synthetic expression cassettes comprising a minimal promoter and a cell-specific enhancer for expression of a nucleic acid of interest in one or more specific cell subtypes are disclosed. Vectors and host cells comprising such synthetic expression cassettes are also disclosed. The application also discloses methods for expressing a nucleic acid of interest, such as a nucleic acid encoding a chimeric antigen receptor (CAR), in a cell and for treating diseases or conditions such as cancers and genetic diseases using the synthetic expression cassettes, vectors and cells.

15 Claims, 19 Drawing Sheets

Specification includes a Sequence Listing.

(56) References Cited

OTHER PUBLICATIONS

Hacein-Bey-Abina et al., "Efficacy of Gene Therapy for X-Linked Severe Combined Immunodeficiency", N Engl J Med, 363: 355-364 (2010).
Hacein-Bey-Abina et al., "A modified gamma-retrovirus vector for X-linked severe combined immunodeficiency", N Engl J Med, 371:1407-1417 (2014).
Hacobian et al., "Pusing the Right Buttons: Improving Efficacy of Therapeutic DNVA Vectors", Tissue Engineering: Part B, 24(3) (2018).
Halkias et al., "Tracking migration during human T cell development", Cell. Mol. Life Sci., 71:3101-17 (2014).
Hambor et al., "Identification and Characterization of an Alu-Continaing, T-Cell-Specific Enhancer Located in the Last Intron of the Human CD8alpha Gene", Molecular and Cellular Biology, 7056-7070 (1993).
Harrison et al., "Unlocking the potential of anti-CD33 therapy in adult and childhood Acute Myeloid Leukaemia (AML)", Experimental Hematology, 54:40-50 (2017).
Haso et al., "Anti-CD22-chimeric antigen receptors targeting B-cell precursor acute lymphoblastic leukemia", Blood 121:1165-1174 (2013).
Huang et al., "Maintenance of hematopoietic stem cells through regulation of Wnt and mTOR pathways", Nat Med, 18:1778-1785 (2021).
Humbert et al., "Measles virus glycoprotein-pseudotyped lentiviral vectors are highly superior to vesicular stomatitis virus G pseudotypes for genetic modification of monocyte-derived dendritic cells", Journal of Virology, 86:5192-5203 (2012).
Jena et al., "Chimeric antigen receptor (CAR)-specific monoclonal antibody to detect CD19-specific T cells in clinical rials", PLoS One, 8:e57838 (2013).
Kalscheuer al., "A model for personalized in vivo analysis of human immune responsiveness", Sci Transl Med., 4:125ra30 (2012).
Kershaw et al., "Gene-engineered T cells for cancer therapy", Nat Rev Cancer, 13:525-541 (2013).
Kurd et al., "T-cell selection in the thymus: a spatial and temporal perspective", Immunol Rev., 271:114-126 (2016).
La Motte-Mohs et al., "Induction of T-cell development from human cord blood hematopoietic stem cells by Delta-like 1 in vitro", Blood, 105:1431-1439 (2005).
Lee et al., "T cells expressing CD19 chimeric antigen receptors for acute lymphoblastic leukaemia in children and young adults: a phase 1 dose-escalation trial", Lancet, 15, 385:517-528 (2015).
Lévy et al., "Lentiviral vectors displaying modified measles virus gp overcome pre-existing immunity in in vivo-like transduction of human T and B cells", Mol Ther, 20:1699-1712 (2012).
Lizio et al., "Gateways to the FANTOM5 promoter level mammalian expression atlas", Genome Biology, 16:22 (2015).
Lowe et al., "In vitro generation of human NK cells expressing chimeric antigen receptor through differentiation of gene-modified hematopoietic stem cells", Methods Mol Biol., 1441:241-251 (2016).
Markert et al., "Thymus transplantation", Clin Immunol., 135(2): 236-246 (2010).
Matsuda et al., "ChIP-seq analysis of genomic binding regions of five major transcription factors in mouse epiblast stem cells that highlights a central role for ZIC2", Development, 144:1948-1958 (2017).
Maude et al., "Chimeric antigen receptor T cells for sustained remissions in leukemia", N Engl J Med, 371(16):1507-1517 (2014).
Maude et al., "CD19 targeted chimeric antigen receptor T-cell therapy for acute lymphoblastic leukemia", Blood, 125: 4017-4023 (2015).
Min et al., "Predicting enhancers with deep convolutional neural networks", BMC Bioinformatics, 18:478 (2017).
Papadakis et al., "Promoters and control elements: designing expression cassettes for gene therapy", Current Gene Therapy, 4:89-113 (2004).
Porter et al., "Chimeric antigen receptor T cells persist and induce sustained remissions in relapsed refractory chronic lymphocytic leukemia", Sci Transl Med., 7:303ra139 (2015).
Poulin et al., "Evidence for adequate thymic function but impaired naive T-cell survival following allogeneic hematopoietic stem cell transplantation in the absence of chronic graft-versus-host disease", Blood, 102(13):4600-4607 (2003).
Savoldo et al., "CD28 costimulation improves expansion and persistence of chimeric antigen receptor-modified T cells in lymphoma patients", The Journal of Clinical Investigation, 121(5):1822-1826 (2011).
Sportès et al., "Administration of rhIL-7 in humans increases in vivo TCR repertoire diversity by preferential expansion of naive T cell subsets", J. Exp. Med., 205(7):1701-1714 (2008).
Teachey et al., "Identification of Predictive Biomarkers for Cytokine Release Syndrome after Chimeric Antigen Receptor T-cell Therapy for Acute Lymphoblastic Leukemia", Cancer Discov, 6(6):664-679 (2016).
Vanhille et al., "High-throughput and quantitative assessment of enhancer activity in mammals by CapStarr-seq", Nature Communications, 6:6905 (2015).
Zhan et al., "The identification of hematopoietic-specific regulatory elements for WASp gene expression", Molecular Therapy—Methods & Clinical Development, 3, 16077 (2016).
International Search Report and Written Opinion in respect of PCT/CA2020/050084.
Partial European Search Report in respect of corresponding EP application No. 20745011.5.

* cited by examiner pENTR1a-Tenh-minCMV-GFP−SV40PolyA pENTR1a-minCMV-GFP−SV40PolyA pENTR1a-minCMV-GFP pHRSIN-Tenh-minCMV-GFP –SV40PolyA pHRSIN-DEST pENTR1a-Tenh-minCMV-GFP –SV40PolyA

|  | C1 bs | | C9 bs | | C12 bs | | C13 bs | | C29 bs | | C167 bs | | C158 bs | | C154 bs | | C134 bs | | C113 bs | | C57 bs | |
|---|---|---|---|---|---|---|---|---|---|---|---|---|---|---|---|---|---|---|---|---|---|---|
|  | n | % in pop | n | % in pop | n | % in pop | n | % in pop | n | % in pop | n | % in pop | n | % in pop | n | % in pop | n | % in pop | n | % in pop | n | % in pop |
| NK | 2/11 | 66.7 | 2/25 | 8 | 3/19 | 15.8 | 1/5 | 20 | 0 | 0.00 | 1/4 | 33.3 | 0 | 0 | 1/7 | 33.3 | 0 | 0 | 3/36 | 100 | 3/30 | 100 |
| T | 1/11 | 10 | 6/25 | 24 | 3/19 | 15.8 | 0 | 0 | 2/11 | 18.2 | 0 | 0 | 3/8 | 30 | 0 | 0 | 3/11 | 30 | 7/36 | 70 | 8/30 | 80 |
| NK/T | 7/11 | 33.3 | 13/25 | 52 | 3/19 | 52.6 | 2/5 | 40 | 6/11 | 54.5 | 2/4 | 9.5 | 2/8 | 9.5 | 5/7 | 23.8 | 8/11 | 26.6 | 19/36 | 90.5 | 16/30 | 76.2 |
| B | 1/11 | 16.7 | 3/25 | 12 | 2/19 | 10.5 | 5/5 | 40 | 3/11 | 27.3 | 1/4 | 16.7 | 1/8 | 16.7 | 1/7 | 16.7 | 1/11 | 16.7 | 6/36 | 100 | 4/30 | 66.7 |
| B/NK | 0/11 | 0 | 1/25 | 4 | 1/19 | 5.3 | 0 | 0 | 0 | 0.00 | 0 | 0 | 0 | 0 | 0 | 0 | 1/11 | 0 | 1/36 | 0 | 1/30 | 0.00 |
| TOTAL | 11 | | 25 | | 19 | | 5 | | 11 | | 4 | | 6 | | 7 | | 11 | | 36 | | 30 | | n : column indicates the number of times that this predicted conserved binding site was found within our selected sequences % in population: indicates the percentage of a cell-population specific enhancer that bears this predicted conserved binding site

FIG. 13

CELL SPECIFIC TRANSCRIPTIONAL REGULATORY SEQUENCES AND USES THEREOF

CROSS-REFERENCE TO RELATED APPLICATIONS

The present application is a National Entry Application of PCT application no. PCT/CA2020/050084 filed on Jan. 24, 2020, which claims the benefit of U.S. provisional application Ser. No. 62/796,254 filed on Jan. 24, 2019. All documents above are incorporated herein in their entirety by reference.

TECHNICAL FIELD

The present invention generally relates to the targeted expression of genes in specific cell subtypes, for example immune cells such as T cells, B cells and natural killer (NK) cells, which may be used in hematopoietic stem cell (HSC) engineering and cell-based therapy.

SEQUENCE LISTING

Pursuant to 37 C.F.R. 1.821 (c), a sequence listing is submitted herewith as an ASCII compliant text file named G12810_00800-Seq listing_ST25.txt, created on Jul. 14, 2021 and having a size of ~32 kilobytes. The content of the aforementioned file is hereby incorporated by reference in its entirety.

BACKGROUND ART

The targeted expression of a transduced gene in a given cell subtype or tissue is challenging. With the growing fields of stem cell engineering and inducible pluripotent stem cells (iPS) research, there is a need for the ability to express a given protein only in targeted populations stemming from the parent cell. However, the use of traditional/natural promoter is faced with the technical issue of size and sometimes specificity. For example, currently, gene therapy for hematopoietic-related disorders relies on the transduction of HSC with a transgene under the control of a strong promoter[1,2]. With this type of construct, the cells that originate from the modified stem cells will express the new gene, irrespectively of the cell subtype, which could potentially lead to hazardous consequences.

Chimeric Antigen Receptor (CAR) immune cell therapy has emerged as a promising new therapeutic tool against various cancer. In CAR immune cell therapy, patient's immune cells (e.g., T cells, NK cells) are engineered to express CARs that binds to tumor antigens, which permits the specific killing of tumor cells expressing the antigen. Currently, this strategy, although potent, typically does not last because of T-cell exhaustion and loss of engineered T cells in vivo. Moreover, the infusion of a large number of CAR-T cells may lead to high toxicity due to a massive release of cytokines (cytokine release syndrome). These is thus a need for an approach that permits the continuous and progressive replenishment of CAR-modified cells in the circulation, and which limits the expression of the CAR only to specific cells (e.g., T cells, NK cells).

The present description refers to a number of documents, the content of which is herein incorporated by reference in their entirety.

SUMMARY OF THE INVENTION

The present disclosure provides the following items:
1. A synthetic expression cassette for expressing a nucleic acid of interest in a cell comprising:
   (i) a minimal promoter; and
   (ii) a transcriptional enhancer operatively coupled to the minimal promoter for expression of the nucleic acid of interest in the cell, wherein the transcriptional enhancer comprises a sequence having at least 70% sequence identity with at least 50 consecutive nucleotides from any one of the sequences set forth in SEQ ID NOs: 7-47.
2. The synthetic expression cassette of item 1, wherein the transcriptional enhancer comprises a sequence having at least 70% sequence identity with at least 100 consecutive nucleotides from any one of the sequences set forth in SEQ ID NOs: 7-47.
3. The synthetic expression cassette of item 2, wherein the transcriptional enhancer comprises a sequence having at least 70% sequence identity with any one of the sequences set forth in SEQ ID NOs: 7-47.
4. The synthetic expression cassette of item 1, wherein the transcriptional enhancer comprises a sequence having at least 80% sequence identity with at least 50 consecutive nucleotides from any one of the sequences set forth in SEQ ID NOs: 7-47.
5. The synthetic expression cassette of item 4, wherein the transcriptional enhancer comprises a sequence having at least 80% sequence identity with at least 100 consecutive nucleotides from any one of the sequences set forth in SEQ ID NOs: 7-47.
6. The synthetic expression cassette of item 5, wherein the transcriptional enhancer comprises a sequence having at least 80% sequence identity with any one of the sequences set forth in SEQ ID NOs: 7-47.
7. The synthetic expression cassette of item 1, wherein the transcriptional enhancer comprises a sequence having at least 90% sequence identity with at least 50 consecutive nucleotides from any one of the sequences set forth in SEQ ID NOs: 7-47.
8. The synthetic expression cassette of item 7, wherein the transcriptional enhancer comprises a sequence having at least 90% sequence identity with at least 100 consecutive nucleotides from any one of the sequences set forth in SEQ ID NOs: 7-47.
9. The synthetic expression cassette of item 8, wherein the transcriptional enhancer comprises a sequence having at least 90% sequence identity with any one of the sequences set forth in SEQ ID NOs: 7-47.
10. The synthetic expression cassette of item 1, wherein the transcriptional enhancer comprises a sequence having at least 95% sequence identity with at least 50 consecutive nucleotides from any one of the sequences set forth in SEQ ID NOs: 7-47.
11. The synthetic expression cassette of item 10, wherein the transcriptional enhancer comprises a sequence having at least 95% sequence identity with at least 100 consecutive nucleotides from any one of the sequences set forth in SEQ ID NOs: 7-47.
12. The synthetic expression cassette of item 11, wherein the transcriptional enhancer comprises a sequence having at least 95% sequence identity with any one of the sequences set forth in SEQ ID NOs: 7-47.
13. The synthetic expression cassette of item 1, wherein the transcriptional enhancer comprises or consists of at least 50 consecutive nucleotides from any one of the sequences set forth in SEQ ID NOs: 7-47.
14. The synthetic expression cassette of item 13, wherein the transcriptional enhancer comprises or consists of at least 100 consecutive nucleotides from any one of the sequences set forth in SEQ ID NOs: 7-47.
15. The synthetic expression cassette of item 13, wherein the transcriptional enhancer comprises or consists of any one of the sequences set forth in SEQ ID NOs: 7-47.
16. The synthetic expression cassette of any one of items 1 to 15, wherein the minimal promoter is a human cytomegalovirus CMV minimal promoter (miniCMV).
17. The synthetic expression cassette of item 16, wherein the minimal promoter comprises or consists of the sequence of SEQ ID NO: 6.
18. The synthetic expression cassette of any one of items 1 to 17, wherein the transcriptional enhancer is upstream of the minimal promoter in the synthetic expression cassette.
19. The synthetic expression cassette of any one of items 1 to 18, further comprising a polyadenylation (poly(A)) signal.
20. The synthetic expression cassette of any one of items 1 to 19, further comprising a transcriptional termination signal.
21. The synthetic expression cassette of any one of items 1 to 20, further comprising the nucleic acid of interest operatively coupled to the minimal promoter and transcriptional enhancer.
22. The synthetic expression cassette of any one of items 1 to 21, further comprising a selectable marker.
23. The synthetic expression cassette of any one of items 1 to 22, wherein the cell is a stem cell.
24. The synthetic expression cassette of item 23, wherein the stem cell is a hematopoietic stem cell (HSC), an embryonic stem cell, a totipotent stem cell, a pluripotent stem cell, a multipotent stem cell or an induced pluripotent stem cell (iPSC).
25. The synthetic expression cassette of any one of items 1 to 22, wherein the cell is an immune cell.
26. The synthetic expression cassette of item 25, wherein the immune cell is a T cell, a natural killer (NK) cell, or a B cell.
27. The synthetic expression cassette of any one of items 1 to 26, wherein the nucleic acid of interest encoded a chimeric antigen receptor (CAR).
28. A vector comprising the synthetic expression cassette of any one of items 1 to 27.
29. The vector of item 28, wherein the vector is a viral vector.
30. A host cell comprising the synthetic expression cassette of any one of items 1 to 27 or the vector of item 28 or 29.
31. The host cell of item 30, wherein said cell is a hematopoietic stem cell, a T cell, a natural killer (NK) cell, or a B cell.
32. A composition comprising the host cell of item 30 or 31.
33. A method for inducing the expression of a nucleic acid of interest by a cell, the method comprising introducing the synthetic expression cassette of any one of items 1 to 27 or the vector of item 28 or 29 in the cell.
34. The method of item 33, wherein the nucleic acid of interest encodes a protein that is absent or defective in said cell.
35. The method of item 33 or 34, wherein the nucleic acid of interest encodes a chimeric antigen receptor (CAR).
36. The method of any one of items 33 to 35, wherein said cell is a hematopoietic stem cell, a T cell, a natural killer (NK) cell, or a B cell.
37. A method for treating a disease, condition or disorder in a subject, the method comprising administering an effective amount of the cell of item 30 or 31, or the composition of item 32, to said subject.
38. The method of item 37, wherein the disease, condition or disorder is associated with the absence of expression of a protein or the expression of a defective protein, and wherein the nucleic acid of interest encodes a functional form of the protein.
39. The method of item 37, wherein the disease, condition or disorder is associated with expression of an antigen, and wherein the nucleic acid of interest encodes a recombinant receptor that specifically binds to the antigen.
40. The method of item 39, wherein the recombinant receptor is a chimeric antigen receptor (CAR).
41. The method of item 39 or 40, wherein the disease, condition or disorder is a cancer, an autoimmune or inflammatory disease, or an infectious disease.
42. The method of item 41, wherein the disease, condition or disorder is a cancer.
43. The method of item 42, wherein the cancer is a hematological cancer.
44. The method of any one of items 37 to 43, wherein said cell is a hematopoietic stem cell, a T cell, a natural killer (NK) cell, or a B cell.
45. The method of any one of items 37 to 44, wherein said method comprises administering at least $1 \times 10^2$, $1 \times 10^3$ or $1 \times 10^4$ cells to said subject.
46. The method of item 45, wherein said method comprises administering $1 \times 10^6$ to $1 \times 10^8$ cells to said subject.
47. The method of any one of items 37 to 46, wherein said cells are autologous cells.
48. The method of any one of items 37 to 46, wherein said cells are allogeneic cells.
49. The cell of item 30 or 31, or the composition of item 32, for use in treating a disease, condition or disorder in a subject.
50. The cell or composition for use according to item 50, wherein the disease, condition or disorder is associated with the absence of expression of a protein or the expression of a defective protein, and wherein the nucleic acid of interest encodes a functional form of the protein.
51. The cell or composition for use according to item 50, wherein the disease, condition or disorder is associated with expression of an antigen, and wherein the nucleic acid of interest encodes a recombinant receptor that specifically binds to the antigen.
52. The cell or composition for use according to item 51, wherein the recombinant receptor is a chimeric antigen receptor (CAR).
53. The cell or composition for use according to item 51 or 52, wherein the disease, condition or disorder is a cancer, an autoimmune or inflammatory disease, or an infectious disease.
54. The cell or composition for use according to item 53, wherein the disease, condition or disorder is a cancer.
55. The cell or composition for use according to item 54, wherein the cancer is a hematological cancer.

56. The cell or composition for use according to any one of items 49 to 55, wherein said cell is a hematopoietic stem cell, a T cell, a natural killer (NK) cell, or a B cell.
57. The cell or composition for use according to any one of items 49 to 56, wherein said method comprises administering at least $1\times10^2$, $1\times10^3$ or $1\times10^4$ cells to said subject.
58. The cell or composition for use according to item 57, wherein said method comprises administering $1\times10^6$ to $1\times10^8$ cells to said subject.
59. The cell or composition for use according to any one of items 49 to 58, wherein said cells are autologous cells.
60. The cell or composition for use according to any one of items 49 to 58, wherein said cells are allogeneic cells.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 3 shows the results of in vitro experiments for assessing the expression pattern of GFP under the control of the T cell-specific synthetic promoter Chr16-445-minCMV.

FIG. 8A shows the percentage of human CD45$^+$ cells that express GFP in the blood (left bars), spleen (middle bars) and bone marrow (right bars) (results from 2 humanized mice). FIG. 8B shows the expression of GFP in human CD45$^+$ cells isolated from the bone marrow of 2 humanized mice. Dot plots show that NK cells (CD56$^+$), but not B cells (CD19$^+$CD3$^-$) or T cells (CD3$^+$CD19$^-$), express the GFP when the mice were humanized with CD34$^+$ transduced with the GFP under the control of the NK8-cell specific promoter (SEQ ID NO:14).

FIG. 10A: CAR-CD33 expression measured by flow cytometry following transduction of primary T-cells with the CAR-CD33 construct under the control of the non-specific SFFV promoter or the T-cell specific promoter. FIG. 10B: Cytotoxicity against CD33$^+$ or CD33$^-$ AML cells of T-cells expressing CAR-CD33 under the control of the SFFV (strong) promoter or the T-cell specific promoter (Tspe) at a 2:1 ratio (no significative difference). * $p<0.001$. FIG. 10C: CAR-CD22 expressed under the Tenh Chr16-445 (Tspe) promoter induced a CAR expression strong enough to result in a similar CAR-specific cytotoxicity against RS4; 11 ALL-cell line to that of SFFV (strong) promoter (ratios of 0.5:1/1:1/2:1/4:1). FIG. 10D: Primary T cells transduced with a CAR-GD2 under the control of the T-cell specific promoter (Chr16-445) (squares) induced a cytotoxicity against a GD2$^+$ NB-cell line (SK-N-DZ), at levels similar to those of primary T cell transduced with a non-specific strong promoter (SFFV, circles). In contrast, unmodified primary T-cells (diamonds) did not kill the target cell line. ** $p<0.0001$

11C shows the percentage of expression of the CAR-CD22 in the different sub-populations obtained in the OP9-DL4 and OP9 systems when the CAR-CD22 was expressed under the control of the T-cell specific promoter (Chr16-445, middle bars), or of a strong non-specific promoter (UCOE-SFFV, left bars). Black bars (left) depict the results obtained with untransduced cells as a negative control. DP: Double-positive.

Figure 12:
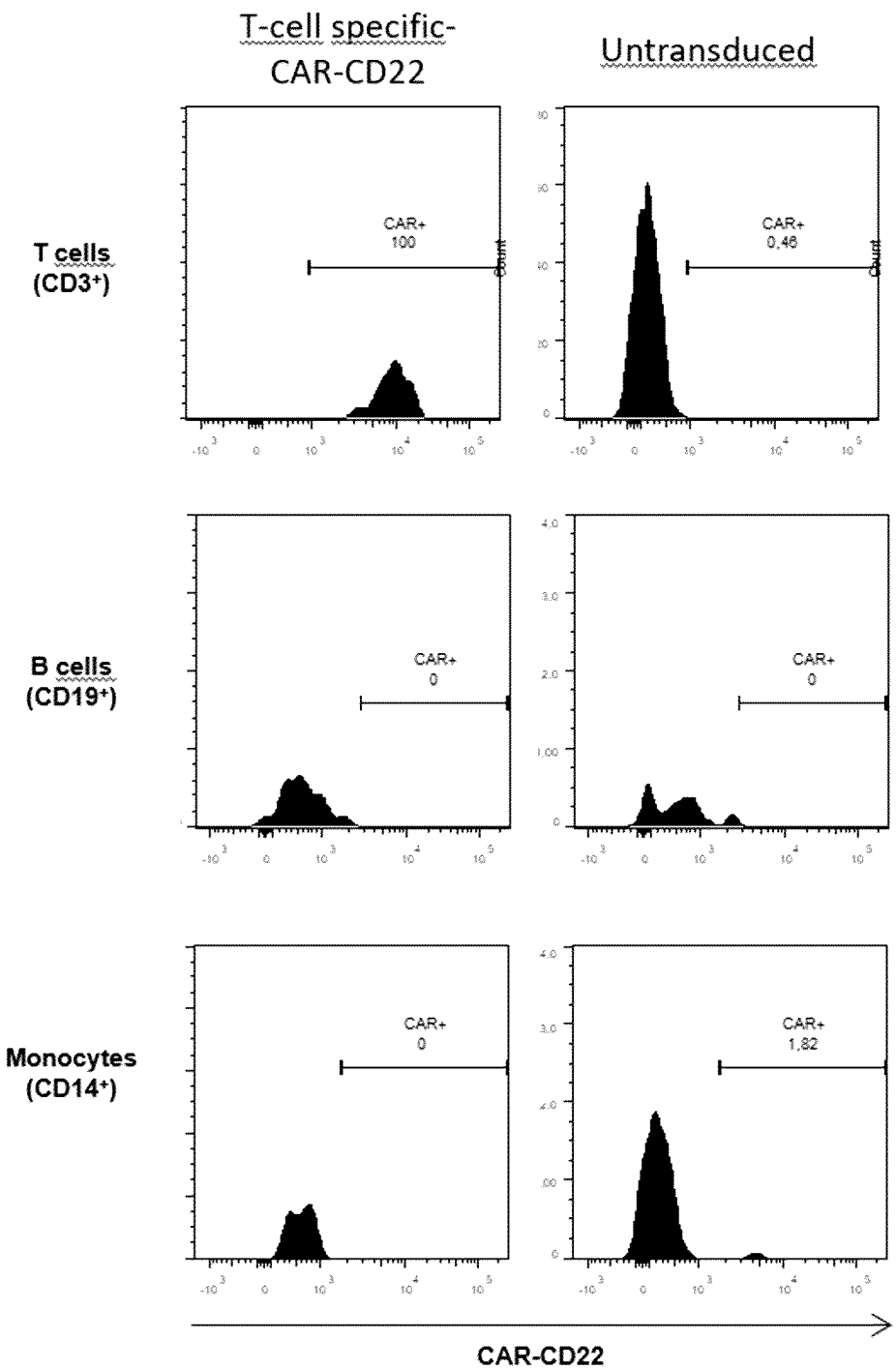

FIG. 12 shows the results of in vivo experiments aiming at testing the differentiation of $CD34^+$ cells transduced with a CAR-CD22 under the control of the T-cell specific promoter (Chr16-445). CAR-CD22 expression was monitored in $hCD45^+$ cells of the blood of BLT mice 30 weeks post-humanization. Histogram plots shows that T cells ($CD3^+$), but not B cells ($CD19^+$) or monocytes ($CD14^+$), express the CAR-CD22 when the mice were humanized with $CD34^+$ modified with the CAR-CD22 under the control of the T-cell specific promoter (Chr16-445) (left column). This expression was not observed when the $CD34^+$ were not transduced (negative control, right column).

DISCLOSURE OF INVENTION

Unless otherwise defined herein, scientific and technical terms used in connection with this disclosure shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the disclosure are generally performed according to conventional methods well-known in the art and as described in various general and more specific references that are cited and discussed throughout the specification unless otherwise indicated. See, e.g.: Sambrook J. & Russell D. Molecular Cloning: A Laboratory Manual, $3^{rd}$ ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual; Cold Spring Harbor Laboratory Press, Cold Spring Harbor, N.Y. (1998); and Coligan et al., Short Protocols in Protein Science, Wiley, John & Sons, Inc. (2003). Any enzymatic reactions or purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art.

The use of the terms "a" and "an" and "the" and similar referents in the context of describing the technology (especially in the context of the claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

The use of any and all examples, or exemplary language ("e.g.", "such as") provided herein, is intended merely to better illustrate the technology and does not pose a limitation on the scope of the claimed invention unless otherwise claimed.

No language in the specification should be construed as indicating any non-claimed element as essential to the practice of the claimed invention.

Herein, the term "about" has its ordinary meaning. The term "about" is used to indicate that a value includes an inherent variation of error for the device or the method being employed to determine the value, or encompass values close to the recited values, for example within 10% of the recited values (or range of values).

The present inventors have developed an alternative strategy to the use of traditional promoters by designing specific synthetic regulatory elements to target the expression of a gene of interest in a cell subtype-specific manner. By engineering the transduced gene to be under the control of this synthetic regulatory element, and by transducing this construct into stem cells, it has been possible to direct gene expression exclusively in a specific and targeted cell subtype (or subtypes) that derive(s) from these genetically-modified stem cells, which is a significant refinement of the actual methods. Several cell-specific transcriptional enhancer candidates have been identified. As a proof-of concept, a first "synthetic regulatory element" comprising a T cell-specific transcriptional enhancer candidate that induced the expression of the transgene specifically in the human T cell population was designed, and the same methodology was successfully applied to design other cell-specific promoters, notably two human NK cell-specific promoters and one B cell-specific promoter. The designed human T/NK/B-cell specific promoters have a reduced size and showed good specificity, and are thus amenable for use in human gene therapy and HSC engineering.

Synthetic Expression Cassette

Accordingly, in a first aspect, the present disclosure provides synthetic expression cassette for expressing a nucleic acid (e.g., gene, gRNA, miRNA, shRNA) of interest in a cell comprising: a minimal promoter; and a transcriptional enhancer operatively coupled to the minimal promoter for expression of the nucleic acid of interest in the cell, wherein the transcriptional enhancer comprises a sequence having at least 70% sequence identity with at least 50 consecutive/contiguous nucleotides, preferably at least 100, 150, 200 or 250 consecutive/contiguous nucleotides, from one of the sequences set forth in SEQ ID NOs: 7-47, preferably SEQ ID NOs: 7-17 and 23.

The term "enhancer" or "transcriptional enhancer" or "transcriptional regulatory element" refers to a cis-acting sequence that comprises one or more binding sites for transcription factors or transcriptional activators and that increases the activity of a promoter (e.g. a minimal promoter) in an orientation- and position-independent manner. The transcriptional enhancer may be located upstream or downstream of the minimal promoter. In an embodiment, the transcriptional enhancer is located upstream of the promoter.

In an embodiment, the transcriptional enhancer is a cell type- or subtype-specific transcriptional enhancer, i.e. the transcriptional enhancer specifically increases the activity of the promoter (and in turn the expression of the peptide/ protein, or nucleic acid (e.g., miRNA, shRNA, gRNA), of interest) in a particular cell type or subtype. The term "specifically increases" as used herein means that the increase in activity of the minimal promoter in the target cell type or subtype is higher than that in the other cell types or subtypes. In embodiment, the transcriptional enhancer is an immune cell-specific transcriptional enhancer, i.e. it specifically increases the activity of the promoter in one or more immune cell type(s), such as T cells, NK cells, B cells, macrophages, dendritic cells, basophils, neutrophils, etc. In an embodiment, the immune cell-specific transcriptional enhancer comprises a sequence having at least 70% sequence identity with at least 50 consecutive/contiguous nucleotides, preferably at least 100, 150, 200 or 250 consecutive/contiguous nucleotides, from one of the sequences set forth in SEQ ID NOs: 7-47, preferably SEQ ID NOs: 7-17 and 23, and maintains transcriptional enhancing activity (i.e. exhibits transcriptional enhancing activity that is similar or better than the native sequence). In an embodiment, the immune cell-specific transcriptional enhancer comprises a sequence having at least 70% sequence identity with one of the sequences set forth in SEQ ID NOs: 7-47, preferably SEQ ID NOs: 7-17 and 23, and maintains transcriptional enhancing activity (i.e. exhibits transcriptional enhancing activity that is similar or better than the native sequence).

In further embodiments, the immune cell-specific transcriptional enhancer comprises or consists of a sequence having at least 75%, 80%, 85%, 90%, 95%, 96%, 97%, 98% or 99% sequence identity with at least 50 consecutive/contiguous nucleotides, preferably at least 100, 150, 200 or 250 consecutive/contiguous nucleotides, from one of the sequences set forth in SEQ ID NOs: 7-47, preferably SEQ ID NOs: 7-17 and 23. In further embodiments, the immune cell-specific transcriptional enhancer comprises or consists of a sequence having at least 75%, 80%, 85%, 90%, 95%, 96%, 97%, 98% or 99% sequence identity with one of the sequences set forth in SEQ ID NOs: 7-47, preferably SEQ ID NOs: 7-17 and 23.

In further embodiments, the immune cell-specific transcriptional enhancer comprises or consists of at least 50 consecutive/contiguous nucleotides, preferably at least 100, 150, 200 or 250 consecutive/contiguous residues, from one of the sequences set forth in SEQ ID NOs: 7-47, preferably SEQ ID NOs: 7-17 and 23.

Some of the sequences set forth in SEQ ID NOs: 7-47 comprise repetitive domains/motifs. For example, the sequence set forth in SEQ ID NO: 7 comprises a repetitive domain/motif of about 50 nucleotides (sequence: GGTGTGGAGGGCCGGGTGGTGACX$^1$CTX$^2$AGTGAC-AGGTGAGGATGTGGCAX$^3$ (SEQ ID NO: 63), wherein X$^1$ is G or A, preferably G; X$^2$ is G or C, preferably G, and X$^3$ is C or T, preferably C. In an embodiment, the cell-specific transcriptional enhancer comprises at least one, preferably at least 2, 3, 4, 5, 6, 7, or 8 repetitive domains/motifs. The list of putative repetitive motifs that are present in each of the sequences set forth in SEQ ID NOs: 7-47 are depicted in Table IV (SEQ ID Nos: 64-82 and AAAC-CACA). Thus, in an embodiment, the transcriptional enhancer sequence comprises one or more of the motif(s) depicted in Table IV (SEQ ID Nos: 64-82 and AAAC-CACA). For example, SEQ ID NO:8 includes one or more of motifs #3 (SEQ ID NO:66), #4 (SEQ ID NO:67), #17 (SEQ ID NO:80), and 20 (AAACCACA) depicted in Table IV. In a further embodiment, the transcriptional enhancer sequence comprises the motif(s) and repeats depicted in Table IV for each of SEQ ID NOs: 7-47.

In an embodiment, the synthetic expression cassette is for expressing the nucleic acid of interest in a T cell, and the transcriptional enhancer comprises or consists of a sequence having at least 75%, 80%, 85%, 90%, 95%, 96%, 97%, 98%, 99% or 100% sequence identity with one of the sequences set forth in SEQ ID NOs: 7-10, 13, 14, 18-22, 24-31, 33-43, 45 and 47, preferably SEQ ID NOs: 7-10, 13, 14. In a further embodiment, the synthetic expression cassette is for expressing the nucleic acid of interest in a T cell, and the transcriptional enhancer comprises or consists of a sequence having at least 75%, 80%, 85%, 90%, 95%, 96%, 97%, 98%, 99% or 100% sequence identity with one of the sequences set forth in SEQ ID NOs: 7, 9, 27, 33, 34, 36, 37, 42, 43 and 45, preferably SEQ ID NOs: 7 and 9. In an embodiment, the cell is a CD4$^+$ cells and the transcriptional enhancer comprises or consists of a sequence having at least 75%, 80%, 85%, 90%, 95%, 96%, 97%, 98%, 99% or 100% sequence identity with one of the sequences set forth in SEQ ID NOs: 22, 34, 37, 38, 43, 45 and 47.

In an embodiment, the synthetic expression cassette is for expressing the nucleic acid of interest in an NK cell, and the transcriptional enhancer comprises or consists of a sequence having at least 75%, 80%, 85%, 90%, 95%, 96%, 97%, 98%, 99% or 100% sequence identity with one of the sequences set forth in SEQ ID NOs: 8, 10-14, 18-22, 24-26, 28-31, 35, 38-41, 44 and 47, preferably SEQ ID NOs: 11, 12 and 14.

In an embodiment, the synthetic expression cassette is for expressing the nucleic acid of interest in NK and T cells, and the transcriptional enhancer comprises or consists of a sequence having at least 75%, 80%, 85%, 90%, 95%, 96%, 97%, 98%, 99% or 100% sequence identity with the sequence set forth in SEQ ID NOs: 8, 10, 13, 14, 18-21, 22, 24-26, 28-31, 35, 38, 39-41 and 47, preferably SEQ ID NOs: 8, 10, 13 and 14.

In an embodiment, the synthetic expression cassette is for expressing the nucleic acid of interest in B cells, and the transcriptional enhancer comprises or consists of a sequence having at least 75%, 80%, 85%, 90%, 95%, 96%, 97%, 98%, 99% or 100% sequence identity with one of the sequences set forth in SEQ ID NOs: 15-17, 23, 32, 44 and 46, preferably SEQ ID NOs: 15-17 and 23, and more preferably SEQ ID NO: 23.

In an embodiment, the synthetic expression cassette is for expressing the nucleic acid of interest in B and NK cells, and the transcriptional enhancer comprises or consists of a sequence having at least 75%, 80%, 85%, 90%, 95%, 96%, 97%, 98%, 99% or 100% sequence identity with one of the sequences set forth in SEQ ID NO: 44.

In an embodiment, the synthetic expression cassette is for expressing the nucleic acid of interest in immune cells, such as NK cells, T cells, basophils and monocytes/macrophages, and the transcriptional enhancer comprises or consists of a sequence having at least 75%, 80%, 85%, 90%, 95%, 96%, 97%, 98%, 99% or 100% sequence identity with the sequence set forth in SEQ ID NO: 14.

In an embodiment, the cell is a CD4$^+$ cells (e.g., a CD4$^+$ T cell) and the transcriptional enhancer comprises or consists of a sequence having at least 75%, 80%, 85%, 90%, 95%, 96%, 97%, 98%, 99% or 100% sequence identity with one of the sequences set forth in SEQ ID NOs: 22, 34, 37, 38, 43, 45 and 47.

In another embodiment, the cell is a CD8$^+$ cells (e.g., a CD8$^+$ T cell) and the transcriptional enhancer comprises or consists of a sequence having at least 75%, 80%, 85%, 90%, 95%, 96%, 97%, 98%, 99% or 100% sequence identity with one of the sequences set forth in SEQ ID NOs: 33, 35 and 39-41.

In an embodiment, the transcriptional enhancer sequence comprises one or more binding sites for transcription factor(s). In an embodiment, the transcriptional enhancer sequence comprises binding sites for at least two transcription factor(s). In an embodiment, the transcriptional enhancer sequence comprises binding sites for at least three transcription factor(s). In an embodiment, the transcriptional enhancer sequence comprises binding sites for at least four transcription factor(s). For example, the sequence set forth in SEQ ID NO:13 comprises binding sites for the transcription factors RUNX3, GATA2, FOS and JUN, and thus in an embodiment the sequence of the cell-specific transcriptional enhancer comprises 1, 2, 3 or all of these binding sites. Putative binding sites for transcription factors in each of the sequences set forth in SEQ ID NOs: 7-47 are depicted in Table V. Thus, in an embodiment, the transcriptional enhancer sequence comprises one or more of the binding sites for transcription factor(s) depicted in Table V.

The term "minimal promoter" refers to a promoter that only comprises the minimal elements of a promoter, namely the TATA box (also called the Goldberg-Hogness box) and a transcription initiation site, and which is inactive (or poorly active) at inducing/driving gene expression in the absence of properly located (usually upstream) one or more regulatory elements that enhance promoter activity (transcriptional enhancers). Any minimal promoter sequence known to those of ordinary skill in the art is contemplated for inclusion in the minimal promoter sequences of the present disclosure. Minimal promoter sequences are often derived from viruses or are truncated eukaryotic promoters, and thus the minimal promoter may be a proopiomelanocortin minimal promoter (POMC), an adenoviral minimal promoter, a baculoviral minimal promoter, a CMV minimal promoter, a parvovirus minimal promoter, a herpesvirus minimal promoter, a poxvirus minimal promoter, an adeno-associated virus minimal promoter, a semiliki forest virus minimal promoter, an SV40 minimal promoter, a vaccinia virus minimal promoter, or a retrovirus minimal promoter. Examples of minimal promoters include the human simplex virus thymidine kinase (HSV TK or miniTK) minimal promoter, the cauliflower mosaic virus (CaMV) 35S minimal promoter, the human cytomegalovirus CMV minimal promoter (miniCMV), CMV53 (minCMV with the addition of an upstream GC box), the minimal simian virus 40 promoter (minSV40), MLP (the −38 to +6 region of the adenovirus major late promoter), the minP (synthetic minimal promoter composed of TATA box and transcription start site—from Promega), pJB42CAT5 (a minimal promoter derived from the human junB gene), YB_TATA, and the super core promoter 1 (SCP1) minimal promoter (see Table I below). Several minimal promoters (also sometimes referred to as "core promoters") are described in Ede et al., *ACS Synth Biol.* 2016 May 20; 5(5): 395-404.

TABLE I

Sequences of representative minimal promoters

| Name | Sequence |
|---|---|
| SCP1 | GTACTTATATAAGGGGGTGGGGGCGCGTTCGTCCTCAGTCGCGATCGAACA CTCGAGCCGAGCAGACGTGCCTACGGACCG (SEQ ID NO: 48) |
| miniCMV | GTAGGCGTGTACGGTGGGAGGTCTATATAAGCAGAGCTCGTTTAGTGAACC GTCAGATC (SEQ ID NO: 6) |
| CMV53 | CAACAAAATGTCGTAACAAGGGCGGTAGGCGTGTACGGTGGGAGGTCTATA TAAGCAGAGCTCGTTTAGT<u>GAACCG</u> (SEQ ID NO: 49) |
| minP | AGAGGGTATATAATGGAAGCTCGACTTCCAG (SEQ ID NO: 50) |
| HSV TK (miniTK) | TTCGCATATTAAGGTGACGCGTGTGGCCTCGAACACCGAGCGACCCTGCAG C GACCCGCTTAA (SEQ ID NO: 51) |
| minSV40 | TGCATCTCAATTAGTCAGCAACCATAGTCCCGCCCCTAACTCCGCCCATCCC GCCCCTAACTCCGCCCAGTTCCGCCCATTCTCCGCCCCATCGCTGACTAATT TTTTTTATTTATGCAGAGGCCGAGGCCGCCTCGGCCTCTGAGCTATTCCAGA AGTAGTGAGGAGGCTTTTTTGGAGGCCTAGGCTTTTGCAAAAAGCTT (SEQ ID NO: 52) |
| MLP | GGGGGGCTATAAAAGGGGGTGGGGGCGTTCGTCCTCACTCT (SEQ ID NO: 53) |
| pJB42CAT5 | CTGACAAATTCAGTATAAAAGCTTGGGGCTGGGGCCGAGCACTGGGGACTTT GAGGGTGGCCAGGCCAGCGTAGGAGGCCAGCGTAGGATCCTGCTGGGAGC GGGGAACTGAGGGAAG*CGACGCC*GAGAAAGCAGGCGTACCACGGAGGGAG AGAAAAGCTCCGGAAGCCCAGCAGCG (SEQ ID NO: 54) |
| YB_TATA | TCTAGAGGGTATATAATGGGGG CCA (SEQ ID NO: 55) |

Bold = TATA box consensus sequence
Underlined = consensus GC box sequence
Italics = additional B-recognition element found in pJB42CAT5

Sequence identity between two nucleotide sequences may be determined by comparing each position in the aligned sequences. A degree of identity between nucleotide sequences is a function of the number of identical nucleotides at positions shared by the sequences. As used herein, a given percentage of identity between sequences denotes the degree of sequence identity in optimally aligned sequences. Optimal alignment of sequences for comparisons of identity may be conducted using a variety of algorithms and sequence alignment tools, such as the local homology algorithm of Smith and Waterman, 1981, *Adv. Appl. Math* 2: 482, the homology alignment algorithm of Needleman and Wunsch, 1970, *J. Mol. Biol.* 48: 443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, WI, U.S.A.). Sequence identity may also be determined using the BLAST algorithm, described in Altschul et al., 1990, *J. Mol. Biol.* 215: 403-10 (using the published default settings). Software/tools for performing BLAST analysis may be available through the National Center for Biotechnology Information. Other sequence alignment tools such as Needle, Stretcher, Clustal Omega and Kalign are available through the European Bioinformatics Institute (EMBL-EBI).

The terms "operatively positioned", "operatively linked" and "operatively coupled" mean that a promoter (and/or enhancer) is in a correct functional location and orientation in relation to a nucleic acid sequence to control transcriptional initiation and expression of that nucleic acid. An enhancer is "operatively coupled" to a promoter (e.g. a minimal promoter) when it is in a correct functional location and orientation for increasing the transcriptional activity of the promoter.

The terms "synthetic" mean that the expression cassette is an artificial or recombinant construct that is not found in nature, i.e. that the combination of the minimal promoter and the transcriptional enhancer is not naturally found in the native genome of a cell. In an embodiment, the minimal promoter is heterologous with the transcriptional enhancer, i.e. it is not normally associated with the transcriptional enhancer in its natural environment, e.g., they do not control the expression of the same genes in the native genome of a cell. In an embodiment, the minimal promoter and the transcriptional enhancer are from different cell types or from different organisms (e.g., virus vs. eukaryotic cell). In an embodiment, the minimal promoter and/or the transcriptional enhancer is/are heterologous with the nucleic acid of interest, i.e. they are not normally associated with the nucleic acid of interest in its natural environment. In an embodiment, the transcriptional enhancer is of human origin. In an embodiment, the minimal promoter is of viral origin.

In an embodiment, the synthetic expression cassette further comprises a polyadenylation (poly(A)) signal. The poly(A) signal effects proper polyadenylation of the nucleic acid of interest (transcript). The nature of the poly(A) signal not believed to be crucial to the successful practice of the invention, and thus any such sequence may be employed. Examples of representative poly(A) signals include the SV40 poly(A) signal and/or the bovine growth hormone poly(A) signal, convenient and/or known to function well in various target cells. In an embodiment, the synthetic expression cassette further comprises a Woodchuck Hepatitis Virus (WHP) Posttranscriptional Regulatory Element (WPRE). Such element is commonly used to increase expression of genes delivered by viral vectors, has been shown to increase mRNA stability and protein yield (see, e.g., Lee, Y B, et al. 2005. Exp Physiol. 90(1): 33-7). In an embodiment, the WPRE is used in combination with the poly(A) signal. In another embodiment, the WPRE replaces the poly(A) signal.

In an embodiment, the synthetic expression cassette further comprises a transcriptional termination signal. A "termination signal" or "terminator" is comprised of the DNA sequences involved in specific termination of an RNA transcript by an RNA polymerase. Thus, in certain embodiments, a termination signal that ends the production of an RNA transcript is contemplated.

In an embodiment, the synthetic expression cassette further comprises a nucleic acid of interest. The term "nucleic acid of interest" or "gene of interest" is used to refer to a nucleic acid that encodes a functional peptide or polypeptide (protein) of interest (native or modified peptides/proteins). In an embodiment, the functional peptide or polypeptide is a therapeutic peptide or polypeptide, i.e. a peptide or polypeptide that can be administered to a subject for the purpose of treating or preventing a disease. Any nucleic acid encoding a peptide or polypeptide of interest known to those of ordinary skill in the art is contemplated for inclusion in the synthetic expression cassette. The peptide or polypeptide of interest may be an enzyme, a signaling molecule (e.g., kinase, phosphatase), a receptor, a growth factor (e.g., cytokines), a chemotactic protein (e.g., chemokines), a structural protein (cytoskeletal proteins), a transcription factor, a cell adhesion protein, an antibody or antigen-binding fragment thereof, etc. The peptide or polypeptide may be a naturally-occurring peptide or polypeptide, a fragment or variant thereof, chimeric versions thereof, etc.

In an embodiment, the nucleic acid of interest encodes a recombinant receptor, such as a chimeric antigen receptor (CAR). Such CAR typically comprises a ligand-binding domain (e.g. antibody or antibody fragment such as a single-chain variable fragment (scFv)) that provides specificity for a desired antigen (e.g., tumor antigen) linked to an activating intracellular domain portion, such as a T cell or NK cell activating domain, providing a primary activation signal, in some aspects via linkers and/or transmembrane domain(s).

In particular embodiments, the recombinant receptor (e.g., CAR) comprises an intracellular signaling domain, which includes an activating cytoplasmic signaling domain (also interchangeably called an intracellular signaling region), such as an activating cytoplasmic (intracellular) domain capable of inducing a primary activation signal in an immune cell (T cell, NK cell, for example), a cytoplasmic signaling domain of a T cell receptor (TCR) component (e.g. a cytoplasmic signaling domain of a CD3-zeta (CD3 chain or a functional variant or signaling portion thereof) and/or that comprises an immunoreceptor tyrosine-based activation motif (ITAM).

In some embodiments, the recombinant receptor (e.g., CAR) further comprises an extracellular ligand-binding domain that specifically binds to a ligand (e.g., antigen) antigen. In some embodiments, the ligand, such as an antigen, is a protein expressed on the surface of cells. In some embodiments, the CAR is a TCR-like CAR and the antigen is a processed peptide antigen, such as a peptide antigen of an intracellular protein, which is recognized on the cell surface in the context of a major histocompatibility complex (MHC) molecule.

Exemplary recombinant receptors, including CARs and recombinant TCRs, as well as methods for engineering and introducing the receptors into cells, include those described, for example, in international patent application publication numbers WO 2000/14257, WO 2013/126726, WO 2012/129514, WO 2014/031687, WO 2013/166321, WO 2013/071154, WO 2013/123061, US patent application publication numbers US 2002/131960, US 2013/287748, US 2013/0149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., *Cancer Discov.* 2013 April; 3(4): 388-398; Davila et al. (2013) *PLoS ONE* 8(4): e61338; Turtle et al., *Curr. Opin. Immunol,* 2012 October;

24(5): 633-39; Wu et al., *Cancer*, 2012 Mar. 18(2): 160-75. In some embodiments, the genetically engineered antigen receptors include a CAR as described in U.S. Pat. No. 7,446,190, and those described in International Patent Application Publication No.: WO 2014/055668.

In some embodiments, the recombinant receptor (e.g. CAR) includes in its extracellular portion an antigen- or ligand-binding domain that binds (specifically binds) to an antigen (or a ligand), such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy ($V_H$) and variable light ($V_L$) chains of a monoclonal antibody (mAb). The term "antibody" herein is used in the broadest sense and includes polyclonal and monoclonal antibodies, including intact antibodies and functional (antigen-binding) antibody fragments, including fragment antigen binding (Fab) fragments, $F(ab')_2$ fragments, Fab' fragments, Fv fragments, recombinant IgG (rIgG) fragments, variable heavy chain ($V_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

In some embodiments, the antigen-binding proteins, antibodies and antigen binding fragments thereof specifically recognize an antigen of a full-length antibody. In some embodiments, the heavy and light chains of an antibody can be full-length or can be an antigen-binding portion (a Fab, $F(ab')_2$, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. *Kuby Immunology*, 6$^{th}$ ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., *J. Immunol.* 150: 880-887 (1993); Clarkson et al., *Nature* 352: 624-628 (1991).

Single-domain antibodies (sdAbs) are antibody fragments comprising all or a portion of the heavy chain variable domain or all or a portion of the light chain variable domain of an antibody. In certain embodiments, the single-domain antibody is a human single-domain antibody.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some embodiments, the antibody fragment is a scFv.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

In some embodiments, the CAR comprises an antibody or an antigen-binding fragment (e.g., scFv) that specifically recognizes an antigen, such as an intact antigen, expressed on the surface of a cell.

In some embodiments, the CAR comprises a TCR-like antibody, such as an antibody or an antigen-binding fragment (e.g., scFv) that specifically recognizes an intracellular antigen, such as a tumor-associated antigen, presented on the cell surface as a MHC-peptide complex. In some embodiments, an antibody or antigen-binding portion thereof that recognizes an MHC-peptide complex can be expressed on cells as part of a recombinant receptor, such as an antigen receptor. Among the antigen receptors are functional non-TCR antigen receptors, such as chimeric antigen receptors (CARs). Generally, a CAR comprising an antibody or antigen-binding fragment that exhibits TCR-like specificity directed against peptide-MHC complexes also may be referred to as a TCR-like CAR.

In some embodiments, the recombinant receptors include recombinant T cell receptors (TCRs) and/or TCRs cloned from naturally occurring T cells. In some embodiments, a T cell receptor (TCR) comprises a variable α and β chains (also known as TCRα and TCRβ, respectively) or a variable γ and δ chains (also known as TCRγ and TCRδ, respectively), or a functional fragment thereof such that the molecule is capable of specifically binding to an antigen peptide bound to a MHC receptor. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to MHC molecules. In some embodiments, a TCR also can comprise a constant domain, a transmembrane domain and/or a short cytoplasmic tail (see, e.g., Janeway et al., *Immunobiology: The Immune System in Health and Disease*, 3$^{rd}$ ed., Current Biology Publications, p. 4:33, 1997). For example, in some embodiments, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR for a target antigen (e.g., a cancer/tumor antigen) is identified and introduced into the cells. In some embodiments, nucleic acid encoding the TCR can be obtained from a variety of sources, such as by polymerase chain reaction (PCR) amplification of publicly available TCR DNA sequences. In some embodiments, the TCR is obtained from a biological source, such as from cells, such as from a T cell (e.g., cytotoxic T cell), T cell hybridomas or other publicly available source. In some embodiments, the T-cells can be obtained from in vivo isolated cells. In some embodiments, a high-affinity T cell clone can be isolated from a patient and the TCR isolated. In some embodiments, the T cells can be a cultured T cell hybridoma or clone. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) *Clin Cancer Res.* 15: 169-180 and Cohen et al. (2005) *J Immunol.* 175:5799-5808. In some embodiments, phage display is used to isolate TCRs against a target antigen (see, e.g., Varela-Rohena et al. (2008) *Nat Med.* 14: 1390-1395 and Li (2005) *Nat Biotechnol.* 23:349-354. In some embodiments, the TCR or antigen-binding portion thereof can be synthetically generated from knowledge of the sequence of the TCR of interest.

In some embodiments, the recombinant receptor (e.g., a CAR such as an antibody or antigen-binding fragment thereof), further includes a spacer, which may be or include at least a portion of an immunoglobulin constant region or variant or modified version thereof, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers include those having at least about 10 to 220 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (2013) *Clin. Cancer Res.*, 19:3153 or PCT patent publication number WO 2014/031687.

The antigen/ligand recognition domain generally is linked to one or more intracellular signaling components, such as signaling components that mimic activation through an antigen receptor complex, such as a TCR or NK receptor complex, in the case of a CAR, and/or signal via another cell surface receptor. Thus, in some embodiments, the antigen-binding component (e.g., antibody) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the TCR, CD28, CD3 epsilon, CD45, CD4, CD5, CD8, CD9, CD16, CD22, CD33, CD37, CD64, CD80, CD86, CD134, CD137, CD154. Alternatively, the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one comprising glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 ζ chain. Thus, in some aspects, the CAR is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. In some aspects, the CAR includes a primary cytoplasmic signaling sequence that regulates primary activation of the TCR complex. Primary cytoplasmic signaling sequences that act in a stimulatory manner may comprise signaling motifs which are known as immunoreceptor tyrosine-based activation motifs or ITAMs. Examples of ITAM comprising primary cytoplasmic signaling sequences include those derived from TCR or CD3 ζ, FcR gamma or FcR beta. In some embodiments, cytoplasmic signaling molecule(s) in the CAR comprise(s) a cytoplasmic signaling domain, portion thereof, or sequence derived from CD3 ζ, in some embodiments, to promote full activation, a component for generating a secondary or co-stimulatory signal is also included in the CAR, such as the signaling domain of a costimulatory receptor such as CD28, 4-1BB, OX40, DAP10, and ICOS. In some aspects, an additional CAR is expressed in the same cell and provides the component for generating the secondary or costimulatory signal. In some cases, CARs are referred to as first, second, and/or third generation CARs. In some aspects, a first-generation CAR is one that solely provides an antigen-receptor (e.g., CD3- chain) induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR in some aspects is one that includes multiple costimulatory domains of different costimulatory receptors.

In some embodiments, the CAR or other antigen receptor may further include a marker or the cell may further express a marker, such as a surrogate marker, which may be used to confirm transduction or engineering of the cell to express the receptor, such as a truncated version of a cell surface receptor, such as truncated EGFR (tEGFR). In some aspects, the marker includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. See WO 2014/031687. In some embodiments, introduction of a construct encoding the CAR and EGFRt separated by a T2A ribosome switch can express two proteins from the same construct, such that the EGFRt can be used as a marker to detect cells expressing such construct. In some embodiments, a marker, and optionally a linker sequence, can be any as disclosed in published patent application No. WO 2014/031687. For example, the marker can be a truncated EGFR (tEGFR) that is, optionally, linked to a linker sequence, such as a T2A cleavable linker sequence.

Among the antigens that may be targeted by the chimeric receptors are those expressed in the context of a disease, condition, or cell type to be targeted via the adoptive cell therapy. Among the diseases and conditions are proliferative, neoplastic, and malignant diseases and disorders, including cancers and tumors, including hematologic cancers, cancers of the immune system, such as lymphomas, leukemias, and/or myelomas (e.g., B cell, T cell, and myeloid leukemias, lymphomas, and multiple myelomas).

In some embodiments, the antigen (or a ligand) is a polypeptide. In some embodiments, it is a carbohydrate or other molecule. In some embodiments, the antigen (or a ligand) is selectively expressed or overexpressed on cells of the disease or condition, e.g., the tumor/cancer or pathogenic cells, as compared to normal or non-targeted cells or tissues. In other embodiments, the antigen is expressed on normal cells and/or is expressed on the engineered cells.

In some embodiments, the antigen (or a ligand) is a tumor antigen or cancer marker. In certain embodiments, the antigen is an integrin (e.g., $\alpha_v\beta_5$ integrin, $\alpha_v\beta_3$ integrin, integrin $\beta_7$), B cell maturation antigen (BCMA), B7-H6, carbonic anhydrase 9 (CA9, also known as CAIX or G250), a cancer-testis antigen, cancer/testis antigen IB (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, fetal acetylcholine receptor, ganglioside GD2, O-acetylated GD2 (OGD2), ganglioside GD3, glycoprotein 100 (gp100), Her2/neu (receptor tyrosine kinase erbB2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Rα), IL-13 receptor alpha 2 (IL-13Rα2), kinase insert domain receptor (kdr), kappa light chain, L1 cell adhesion molecule (L1CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC 16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1), galectins (galectin-1, galectin-7) a pathogen-specific antigen, or an antigen associated with a universal tag, and/or biotinylated molecules, and/or molecules expressed by HIV, HCV, HBV or other pathogens such as bacteria and parasites. Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, lgkappa, Iglambda, CD79a, CD79b or CD30. In an embodiment, a plurality of recombinant receptors targeting a plurality of antigens are used. In a further embodiment, two recombinant receptors targeting two antigens are used.

Vector/Plasmids

In an embodiment, the synthetic expression cassette is comprised in a plasmid or a vector. Thus, the present disclosure also relates to a vector or plasmid comprising the synthetic expression cassette described herein. The term "vector" is used to refer to a carrier into which a nucleic acid (e.g., the synthetic expression cassette defined herein) can be inserted for introduction into a cell where it can be replicated. The term "expression vector" or "nucleic acid vector" refers to a vector containing a nucleic acid or "expression cassette" coding for at least part of a gene product capable of being transcribed and "regulatory" or "control" sequences, which refer to nucleic acid sequences necessary for the transcription and possibly translation of an operably linked coding sequence in a particular host cell. In addition to control sequences that govern transcription and translation, expression vectors may contain nucleic acid sequences that serve other functions as well.

In an embodiment, the vector further comprises a nucleic acid encoding a selectable marker or reporter protein. A selectable marker or reporter is defined herein to refer to a nucleic acid encoding a polypeptide that, when expressed, confers an identifiable characteristic (e.g., a detectable signal, resistance to a selective agent) to the cell permitting easy identification, isolation and/or selection of cells containing the selectable marker from cells without the selectable marker or reporter. Any selectable marker or reporter known to those of ordinary skill in the art is contemplated for inclusion as a selectable marker in the vector of the present disclosure. For example, the selectable marker may be a drug selection marker, an enzyme, or an immunologic marker. Examples of selectable markers or reporters include, but are not limited to, polypeptides conferring drug resistance (e.g., kanamycin/geneticin resistance), enzymes such as alkaline phosphatase and thymidine kinase, bioluminescent and fluorescent proteins such as luciferase, green fluorescent protein (GFP), yellow fluorescent protein (YFP), cyan fluorescent protein (CFP), blue fluorescent protein (BFP), citrine and red fluorescent protein from discosoma (dsRED), membrane bound proteins to which high affinity antibodies or ligands directed thereto exist or can be produced by conventional means, and fusion proteins comprising a membrane-bound protein appropriately fused to an antigen tag domain from, among others, hemagglutinin (HA) or Myc. The nucleic acid encoding the selectable marker or reporter protein may be under the control of the same promoter/enhancer as the nucleic acid of interest, or may be under the control of a distinct promoter/enhancer.

In embodiments, the vector may comprise additional elements, such as one or more origins of replication sites (often termed "ori"), restriction endonuclease recognition sites (multiple cloning sites, MCS) and/or internal ribosome entry site (IRES) elements.

In an embodiment, the vector is a viral vector. The term "viral vector" as used herein refers to a recombinant virus capable of transducing cells and introducing their genetic material into the cells. In an embodiment, the viral vector is suitable for use in gene therapy applications. Examples of viral vectors that may be used in gene therapy include retroviruses (lentiviruses), adenoviruses, adeno-associated viruses (AAV), herpesviruses (herpes simplex viruses), alphaviruses, and vaccinia viruses (Poxviruses). In an embodiment, the viral vector is a lentiviral vector. As will be evident to one of skill in the art, the term "lentiviral vector" is used to refer to a lentiviral particle that mediates nucleic acid transfer. Lentiviral particles will typically include various viral components and sometimes also host cell components in addition to nucleic acid(s). In particular aspects, the terms "lentiviral vector," "lentiviral expression vector" are used to refer to lentiviral transfer plasmids and/or infectious lentiviral particles.

In an embodiment, the lentiviral vector is a pseudotyped lentiviral vector. Pseudotyped lentiviral vectors consist of vector particles bearing enveloped proteins (glycoproteins, GP) derived from other enveloped viruses. Such particles possess the tropism of the virus from which the enveloped proteins are derived. One of the widely used glycoproteins for pseudotyping lentiviral vectors is the vesicular stomatitis virus GP (VSV-G), due to the very broad tropism and stability of the resulting pseudotypes. Pseudotyped lentiviral vectors are well known in the art, and several examples are described, for example, in Cronin et al., Curr. Gene Ther. 5(4):387-398. It includes lentiviral vectors pseudotyped with lyssavirus GPs, lymphocytic choriomeningitis virus (LCMV) GPs, alphavirus GPs (e.g., Ross River virus (RRV), Semliki Forest virus (SFV) and Sindbis virus GPs), Filovirus GPs (e.g., Marburg virus and Ebola Zaire virus GPs), gammaretrovirus GPs (e.g., ecotropic MLV, amphotropic 4070A MLV, 10A1 MLV, xenotropic NZB MLV, mink cell focus-forming virus, gibbon ape leukemia (GALV) virus, RD1 14 GPs), Vesicular Stomatitis Virus type-G (VSV-G), Measles-Virus Lentiviral vector (MV-LV), Baboon envelop (BaEV)-LVs and baculovirus GPs (GP64).

In an embodiment, the vector is an episomally-maintained viral vector or non-integrating vector, such as a Sendai virus or vector. Such vectors are not integrated into the genome, but are maintained episomally with cell division due to scaffold/matrix attachment region presence inside vector (see, e.g., Giannakopoulos A et al., *J Mol Biol.* 2009 Apr. 17; 387(5):1239-49; and Haase et al., *BMC Biotechnol.* 2010; 10: 20).

In another embodiment, the vector is a non-viral vector, for example nude DNA, a liposome, a polymerizer or a molecular conjugate.

Cells

In another aspect, the present disclosure provides a cell (host cell, engineered cell) comprising the synthetic expression cassette or vector/plasmid described herein. In an embodiment, the cell is a primary cell, for example a brain/neuronal cell, a peripheral blood cell (e.g., a B or T lymphocyte, a monocyte, a NK cell), a cord blood cell, a bone marrow cell, a cardiac cell, an endothelial cell, an epidermal cell, an epithelial cell, a fibroblast, hepatic cell or a lung/pulmonary cell. In an embodiment, the cell is a bone marrow cell, peripheral blood cell or cord blood cell. In a further embodiment, the cell is an immune cell, such as a T cell (e.g., a $CD8^+$ T cell), a B cell or a NK cell.

In an embodiment, the cell is a stem cell. The term "stem cell" as used herein refers to a cell that has pluripotency which allows it to differentiate into a functional mature cell. It includes primitive hematopoietic cells, progenitor cells, as well as adult stem cells that are undifferentiated cells found in various tissue within the human body, which can renew themselves and give rise to specialized cell types and tissue from which the cells came (e.g., muscle stem cells, skin stem cells, brain or neural stem cells, mesenchymal stem cell, lung stem cells, liver stem cells).

In an embodiment, the cell is a primitive hematopoietic cell. As used herein, the term "primitive hematopoietic cell" is used to refers to cells having pluripotency which allows them to differentiate into functional mature blood cells of the myeloid and lymphoid lineages such as T cells, B cells, NK cells, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages), and that may or may not the ability to regenerate while maintaining their pluripotency (self-renewal). It encompasses "hematopoietic stem cells" or "HSCs", which are cells having both pluripotency which allows them to differentiate into functional mature cells such as granulocytes, erythrocytes, thrombocytes, and monocytes, and the ability to regenerate while maintaining their pluripotency (self-renewal), as well as pluripotent hematopoietic cells that do not have self-renewal capacity. It also encompasses embryonic stem cells (ESCs), which are pluripotent stem cells derived from the inner cell mass of a blastocyst, an early-stage pre-implantation embryo. In an embodiment, the population of cells comprises ESCs. In another embodiment, the population of cells comprises HSCs. HSCs may be obtained from the body or an organ of the body containing cells of hematopoietic origin. Such sources include un-fractionated bone marrow (from femurs, hip, ribs, sternum, and other bones), umbilical cord blood, peripheral blood, liver, thymus, lymph and spleen. All of the aforementioned crude or un-fractionated blood products can be enriched for cells having HSC characteristics in ways known to those of skill in the art. HSCs are phenotypically identified by their small size, lack of lineage (lin) markers, low staining (side population) with vital dyes such as rhodamine 123 (rhodamine$^{DULL}$, also called rho$^0$) or Hoechst 33342, and presence/absence of various antigenic markers on their surface many of which belongs to the cluster of differentiation series, such as: CD34, CD38, CD90, CD133, CD105, CD45 and c-kit.

In an embodiment, the stem cell is an induced pluripotent stem cell (iPSC). The term iPSC refers to a pluripotent stem cell that can be generated directly from adult cells using appropriate factors to "reprogram" the cells.

In an embodiment, the cell is a mammalian cell, for example a human cell.

The synthetic expression cassette or vector/plasmid described herein may be introduced into the cell using standard techniques for introducing nucleic acids into a cell, e.g., transfection, transduction or transformation. In an embodiment, the vector is a viral vector, and the cell is transduced with the vector. As used herein, the term "transduction" refers to the stable transfer of genetic material from a viral particle (e.g., lentiviral) to a cell genome (e.g., hematopoietic cell genome). It also encompasses the introduction of non-integrating viral vectors into cells, which leads to the transient or episomal expression of the gene of interest present in the viral vector.

Viruses may be used to infect cells in vivo, ex vivo, or in vitro using techniques well known in the art. For example, when cells, for instance $CD34^+$ cells or stem cells are transduced ex vivo, the vector particles may be incubated with the cells using a dose generally in the order of between 1 to 100 or 1 to 50 multiplicities of infection (MOI) which also corresponds to $1 \times 10^5$ to 100 or $50 \times 10^5$ transducing units of the viral vector per $10^5$ cells. This, of course, includes amount of vector corresponding to 1, 2, 3, 4, 5, 6, 7, 8, 9, 10, 15, 20, 25, 30, 35, 40, 45, and 50 MOI. Prior to, during, and/or following transduction, the cells may be cultured in media suitable for the maintenance, growth, or proliferation of the cells. The culture conditions of the population of cells will vary depending on different factors, notably, the starting cell population. Suitable culture media and conditions are well known in the art. The culture may be carried out in natural medium, a semi-synthetic medium or a synthetic medium in terms of composition, and may be a solid medium, a semisolid medium or a liquid medium in terms of shape, and any nutrient medium used for cell culture, such as stem cell culture, which may be supplemented with one or more of growth factors. Such medium typically comprises sodium, potassium, calcium, magnesium, phosphorus, chlorine, amino acids, vitamins, cytokines, hormones, antibiotics, serum, fatty acids, saccharides or the like. In the culture, other chemical components or biological components may be incorporated singly or in combination, as the case requires. Such components to be incorporated in the medium may be fetal calf serum, human serum, horse serum, insulin, transferrin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various growth factors or the like. Examples of such basal medium appropriate for a method of expanding stem cells include, without limitation, StemSpan™ Serum-Free Expansion Medium (SFEM) (StemCell Technologies®, Vancouver, Canada), StemSpan™ H3000-Defined Medium (StemCell Technologies®, Vancouver, Canada), CellGro™, SCGM (CellGenix™, Freiburg Germany), StemPro™-34 SFM (Invitrogen®), Dulbecco's Modified Eagle's Medium (DMEM), Ham's Nutrient Mixture H12 Mixture F12, McCoy's 5A medium, Eagle's Minimum Essential Medium (EMEM), MEM medium (alpha Modified Eagle's Minimum Essential Medium), RPMI 1640 medium, Isocove's Modified Dulbecco's Medium (IMDM), StemPro34™ (Invitrogen®), X-VIVO™ 10 (Cambrex®), X-VIVO™ 15 (Cambrex®) and Stemline™ II (Sigma-Aldrich®).

Following transduction, the transduced cells may be cultured under conditions suitable for their maintenance, growth and/or proliferation. In particular aspects, the transduced cells are cultured for about 1, 2, 3, 4, 5, 6, 7, 8, 9, 10, 11, 12, 13 or 14 days before transplantation. Culture conditions for maintaining and/or expanding stem cells are well known in the art.

Typically, the culturing conditions comprise the use of factors like cytokines and growth factors, generally known in the art for stem cell expansion. Such cytokines and growth factors can be biologics or small molecules and they include without limitation IL-1, IL-3, IL-6, IL-11, G-CSF, GM-CSF, SCF, FIT3-L, thrombopoietin (TPO), erythropoietin, and analogs thereof. As used herein, "analogs" include any structural variants of the cytokines and growth factors having the biological activity as the naturally occurring forms, including without limitation, variants with enhanced or decreased biological activity when compared to the naturally occurring forms or cytokine receptor agonists such as an agonist antibody against the TPO receptor (for example, VB22B sc(Fv)2 as detailed in patent publication WO 2007/145227, and the like). Cytokine and growth factor combinations are chosen to maintain/expand stem cells while limiting the production of terminally differentiated cells. In one specific embodiment, one or more cytokines and growth factors are selected from the group consisting of SCF, Flt3-L and TPO.

Human IL-6 or interleukin-6, also known as B-cell stimulatory factor 2 has been described by (Kishimoto, *Ann. review of Immunol.* 23:1, 2005) and is commercially available. Human SCF or stem cell factor, also known as c-kit ligand, mast cell growth factor or Steel factor has been described (Smith, M A et al., *ACTA Haematologica,* 105(3): 143, 2001) and is commercially available. Flt3-L or FLT-3 Ligand, also referred as FL is a factor that binds to flt3-receptor. It has been described (Hannum C, *Nature* 368 (6472): 643-8) and is commercially available. TPO or thrombopoietin, also known as megakarayocyte growth factor (MGDF) or c-Mpl ligand has been described (Kaushansky K (2006). *N. Engl. J. Med.* 354 (19): 2034-45) and is commercially available.

The chemical components and biological components mentioned above may be used not only by adding them to the medium but also by immobilizing them onto the surface of the substrate or support used for the culture, specifically speaking, by dissolving a component to be used in an appropriate solvent, coating the substrate or support with the resulting solution and then washing away an excess of the component. Such a component to be used may be added to the substrate or support preliminarily coated with a substance which binds to the component.

Stem cells may be cultured in a culture vessel generally used for animal cell culture such as a Petri dish, a flask, a plastic bag, a Teflon™ bag, optionally after preliminary coating with an extracellular matrix or a cell adhesion molecule. The material for such a coating may be collagens I to XIX, fibronectin, vitronectin, laminins 1 to 12, nitrogen, tenascin, thrombospondin, von Willebrand factor, osteoponin, fibrinogen, various elastins, various proteoglycans, various cadherins, desmocolin, desmoglein, various integrins, E-selectin, P-selectin, L-selectin, immunoglobulin superfamily, Matrigel®, poly-D-lysine, poly-L-lysine, chitin, chitosan, Sepharose®, alginic acid gel, hydrogel or a fragment thereof. Such a coating material may be a recombinant material having an artificially modified amino acid sequence. The stem cells may be cultured by using a bioreactor which can mechanically control the medium composition, pH and the like and obtain high density culture (Schwartz R M, *Proc. Natl. Acad. Sci. U.S.A.*, 88:6760, 1991; Koller M R, *Bone Marrow Transplant*, 21: 653, 1998; Koller, M R, *Blood*, 82: 378, 1993; Astori G, *Bone Marrow Transplant*, 35(1) 101, 2005).

The cell population may then be washed to remove the compound or composition of invention and/or any other component of the cell culture and resuspended in an appropriate cell suspension medium for short term use or in a long-term storage medium, for example a medium suitable for cryopreservation, for example DMEM with 40% FCS and 10% DMSO. Other methods for preparing frozen stocks for cultured cells also are available to those skilled in the art.

Compositions

In another aspect, the present disclosure provides a composition comprising the synthetic expression cassette, vector or cell described herein. The composition may comprise one or more carrier or excipient, e.g. a buffer, a saline solution, a preservative, etc. In an embodiment, the composition is a pharmaceutical composition comprising at least one pharmaceutically acceptable carrier or excipient. An "excipient," as used herein, has its normal meaning in the art and is any ingredient that is not an active ingredient (drug) itself. Excipients include for example binders, lubricants, diluents, fillers, thickening agents, disintegrants, plasticizers, coatings, barrier layer formulations, lubricants, stabilizing agent, release-delaying agents and other components. "Pharmaceutically acceptable excipient" as used herein refers to any excipient that does not interfere with effectiveness of the biological activity of the active ingredients and that is not toxic to the subject, i.e., is a type of excipient and/or is for use in an amount which is not toxic to the subject. Excipients are well known in the art (see, e.g., *Remington: The Science and Practice of Pharmacy*, by Loyd V Allen, Jr, 2012, 22$^{nd}$ edition, Pharmaceutical Press; *Handbook of Pharmaceutical Excipients*, by Rowe et al., 2012, 7$^{th}$ edition, Pharmaceutical Press). Pharmaceutical compositions may be prepared using standard methods known in the art by mixing the active ingredient having the desired degree of purity with one or more optional pharmaceutically acceptable carriers, excipients and/or stabilizers. The excipient may be selected for administration of the composition by any routes, for example, for intravenous, parenteral, subcutaneous, intramuscular, intracranial, intraorbital, ophthalmic, intraventricular, intracapsular, intraspinal, intrathecal, epidural, intracisternal, intraperitoneal, intranasal or pulmonary (e.g., aerosol) administration. In an embodiment, the pharmaceutical composition is formulated for injection, e.g. as a solution, suspension, or emulsion, including localized injection, catheter administration, systemic injection, intravenous injection, intraperitoneal injection, subcutaneous injection or parenteral administration.

Pharmaceutical compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium comprising, for example, water, saline, phosphate buffered saline, polyol (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can also be lyophilized. The compositions can comprise auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

Sustained-release preparations may be prepared. Suitable examples of sustained-release preparations include semipermeable matrices of solid hydrophobic polymers comprising the antibody, which matrices are in the form of shaped articles, e.g. films, or microcapsules.

The formulations to be used for in vivo administration are generally sterile. Sterility may be readily accomplished, e.g., by filtration through sterile filtration membranes.

Methods/Uses

The present disclosure also relates to a method for inducing the expression of a gene of interest by a cell, the method comprising introducing the synthetic expression cassette or vector described herein in the cell. The present disclosure also relates to a use of the synthetic expression cassette or vector described herein for inducing the expression of a gene of interest by a cell. In an embodiment, the cell is a primary cell, for example a brain/neuronal cell, a peripheral blood cell (e.g., a B or T lymphocyte, a monocyte, a NK cell), a cord blood cell, a bone marrow cell, a cardiac cell, an endothelial cell, an epidermal cell, an epithelial cell, a fibroblast, hepatic cell or a lung/pulmonary cell. In an embodiment, the cell is a bone marrow cell, peripheral blood cell or cord blood cell. In a further embodiment, the cell is an immune cell, such as a T cell (e.g., a CD8$^+$ T cell), a B cell or a NK cell.

In an embodiment, the gene of interest encodes a protein that is defective or absent in the cell. In an embodiment, the gene of interest encodes a recombinant receptor, such as a chimeric antigen receptor (CAR). In an embodiment, the gene of interest encodes a differentiation factor (for cell reprogramming).

The present disclosure also relates to a method for treating a disease, condition or disorder in a subject, the method comprising administering a cell comprising the synthetic expression cassette or vector described herein. The present disclosure also relates to the use of a cell comprising the synthetic expression cassette or vector described herein method for treating a disease, condition or disorder in a subject. The present disclosure also relates to the use of a cell comprising the synthetic expression cassette or vector described herein method for the manufacture of a medicament for treating a disease, condition or disorder in a subject. In an embodiment, the disease, condition or disorder is associated with the absence of expression of a protein or the expression of a defective (e.g., mutated) protein, and the synthetic expression cassette or vector comprises a nucleic acid encoding a functional (e.g., native) protein (e.g., gene therapy).

Examples of diseases/disorders associated with the absence of expression of a protein, or the expression of a defective (e.g., mutated) protein (e.g., genetic diseases/disorders), include certain hematologic and lysosomal storage diseases such as Wiskott-Aldrich syndrome (WAS) (Aiuti et al., Science 341 (6148)), metachromatic leukodystrophy (MLD) (Biffi et al., Science 341 (6148)), Leukocyte adherence deficiency, X-linked CGD, Fanconi anemia, adrenoleukodystrophy, Mucopolysaccharidosis IIIA, as well as immunodeficiencies such as severe combined immunodeficiency (SCID) and adenosine deaminase (ADA) deficiency.

The disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g., cancer), autoimmune or inflammatory disease (e.g., arthritis, rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant), or an infectious disease, e.g. caused by a bacterial, viral or other pathogen. In particular embodiments, the recombinant receptor, e.g., the CAR, specifically binds to the antigen associated with the disease or condition. In an embodiment, the disease, condition or disorder is cancer or an infectious disease, and the nucleic of interest present in the synthetic expression cassette or vector encodes a recombinant receptor, such as a chimeric antigen receptor (CAR), that recognizes an antigen expressed by the tumor cell or infected cell. The tumor may be a solid tumor or a hematologic (blood) tumor. In an embodiment, the cancer is a hematologic cancer, such as a lymphoma, a leukemias, and/or a myeloma (e.g., B-cell, T-cell, and myeloid leukemias, lymphomas, and multiple myelomas). The infectious disease may be a disease caused by any pathogenic infection, such as a viral, bacterial, parasitic (e.g., protozoal) or fungal infection, for example human immunodeficiency virus (HIV) or cytomegalovirus (CMV) infection.

The cells (engineered cells comprising the synthetic expression cassette or vector described herein) or compositions comprising same may administered to a subject or patient having the particular disease or condition to be treated, e.g., via adoptive cell therapy such as adoptive T cell therapy, or stem cell therapy. Methods for administration of engineered cells for adoptive cell therapy are known and may be used in connection with the provided methods and compositions. For example, adoptive T cell therapy methods are described, e.g., in U.S. Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

In some embodiments, the cell therapy, e.g., adoptive T cell therapy or stem cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy or stem cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or super type as the first subject. The cells can be administered by any suitable means. Dosing and administration may depend in part on whether the administration is brief or chronic. Various dosing schedules include but are not limited to single or multiple administrations over various time-points, bolus administration, and pulse infusion.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Dosages may vary depending on attributes particular to the disease or disorder and/or patient and/or other treatments.

In some embodiments, for example, where the subject is a human, the dose of recombinant receptor (e.g., CAR)-expressing cells, stem cells, T cells, or peripheral blood mononuclear cells (PBMCs), is at least $1\times10^2$, $1\times10^3$, $1\times10^4$ or $1\times10^5$ cells, for example in the range of about $1\times10^6$ to $1\times10^8$ such cells, such as $2\times10^6$, $5\times10^6$, $1\times10^7$, $5\times10^7$, or $1\times10^8$ or total such cells, or the range between any two of the foregoing values.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents include a cytokine, such as IL-2, for example, to enhance persistence. In some embodiments, the methods comprise administration of a chemotherapeutic agent.

The cells may be used in combination with other therapy such as other chemotherapy, immunotherapy, radiotherapy, or surgery, according to the disease to be treated.

In some embodiments, the synthetic expression cassette is used as a research tool, for example as reporter tool or in a commercial detection method (assay development). For example, the synthetic expression cassette may be operably linked to a nucleic acid encoding a reporter protein, which may be used for the detection of the expression of a gene of interest in a specific cell type, e.g., to confirm that the gene of interest has been taken up by and is expressed by the cell. The term "reporter protein" refers to a protein that may be easily identified and measured such as fluorescent and luminescent proteins (e.g., GFP, YFP), as well as enzymes that are able to generate a detectable product from a substrate (e.g., luciferase). The synthetic expression cassette may also be used for the cell-specific expression of a gene of interest in vitro, e.g., to assess the effect of the expression of the gene of interest in the targeted cells.

MODE(S) FOR CARRYING OUT THE INVENTION

The present invention is illustrated in further details by the following non-limiting examples.

Example 1: Material and Methods

Experimental design. The experimental strategy to generate synthetic specific promoter (enhancer+minimal CMV promoter) was to first select specific enhancer sequences in silico, amplify the sequence(s) by PCR and then clone the endogenous enhancer sequences upstream of a minimal promoter, namely the CMV minimal promoter (minCMV)[5]. To validate the specificity of the synthetic promoter (enhancer+minCMV) through expression pattern assays, it was cloned upstream of a GFP reporter gene. As proof-of-concept of functional uses, it was cloned upstream of a chimeric antigen receptor (CAR).

Design of specific promoter sequences. Enhancer sequences that are specific for a particular cell type, and that are located upstream of a transcription start site, were selected in silico. To do so, the in silico method of selection was based on the "Functional ANnotation Of The Mammalian genome" FANTOM5 database (generated by RIKEN)[3,4]. The FANTOM5 database has systematically investigated exactly what are the sets of genes that are active in virtually all cell types across the human body, and the genomic regions, which determine where the genes are read from. Therefore, this database includes a large number of active enhancer sequences of different subtypes. In order to browse this data and to select enhancers, the PrESSTo (Promoter Enhancer Slider Selector Tool) for human enhancer was used (http://enhancer.binf.ku.dk/enhancers.php). PrESSTo allows for the selection of enhancers expressed in one of many cells or tissues based on sliders.

The first step to select specific enhancer sequences was based on the Cap Analysis of Gene Expression (CAGE) score reported in FANTOM5 database. A percentage for the cell type of interest (T or NK cell) was chosen, namely 60% for T cells 30% for NK cells. The percentage number for each cell type refers to the proportion of CAGE tag in the given cell population relatively to CAGE tag counts from all cells. The percentage number is a "lowest bound" value: only the enhancers that have higher or equal percentage of expression than the set value for the cell type were returned. The percentage was selected according to the number of hits in the results box. In average, the percentage was set to have less than 20 hits.

The enhancer sequence candidates identified were then selected based on the following criteria:
- a high score (over 0.15 tags per million) in samples representing the cellular population of interest (e.g., T cells or NK cells);
- a low score for all other populations (less than 0.15 tags per million);
- significantly overrepresented only in the given population(s), as defined by PreSSTo.

The selected enhancer sequence candidates were then validated based on ChIP-Seq data, available through the UCSC genome browser tool (Kent W J, et al. The human genome browser at UCSC. *Genome Res.* 2002 June; 12 (6): 996-1006-link available specifically for the selected sequence via the tab "View in UCSC" in the PrESSTo tool. The presence of transcription factor fixation sites that are related to the lineage of interest (e.g., POU2F2 in hematopoietic lineage, GATA3 for T cells) or that are indicative of active regions (ex.: POLR2A) were analyzed. The presence of such sites in the vicinity (within 2000-3000 bp) of the selected enhancer was considered to be indicative of a transcriptionally active region[7].

Additional bioinformatic analysis was used to impose upon the remaining candidate regulatory regions more stringent selection criteria using cell-specific epigenetic characteristics (ENCODE database): (1) chromatin accessibility (i.e DNase-seq, FAIRE-Seq) and (2) histone modifications differentiating active from inactive enhancer regions (ChIP-Seq for H3K27ac). For purposes of illustration, the following strategy was used for selecting the B cell-specific enhancer candidates. After using the PrESSTo tool to select B-cell-specific regulatory regions (i.e specific CAGE signal in genomic regions of B cells and much less in others), the genomic coordinates of those candidate regulatory regions were submitted to the Galaxy bioinformatic web portal (Enis Afgan et al., *Nucleic Acids Research*, Volume 46, Issue W1, 2 Jul. 2018, Pages W537-W544). The same procedure was followed in order to upload into the Galaxy portal the epigenomic data obtained from ENCODE for chromatin accessibility (FAIRE-Seq or/and DNase-Seq) and H3K27ac modifications (ChIP-Seq) for the human cell types of interest, that is B cells, T cells, CD4 cells, CD8 cells, NK cells, monocytes and/or neutrophils and/or CD34+ cells. The next step was to intersect the ensemble of B cell regulatory regions discovered by PrESSTo for presence of B cell-specific H3K27Ac enrichment peaks, which restricts the list to CAGE regions that show an active H3K27Ac signature. The latter regions were then queried for presence of an open chromatin (occurrence of DNA-seq peeks) in B cells, which restrict the CAGE B cell enhancers to those that show evidence of an open chromatin state in B cells along with accompanying H3K27Ac modification (epigenetic signature of transcriptional activity; strongly associated with active enhancers). Further purging of the latter list was performed to successively eliminate the regions that show evidence of chromatin opening and H3K27 acetylation in non-desired cell types, such as T cells, NK cells, monocytes and CD34$^+$ cells. The resulting final list was manually curated in the CAGE database for tag signal intensity and cell specificity, including further analysis of transcription factor binding, occurrence of over-represented DNA motifs (MEME tool) and proximity of known cell-specific genes.

Enhancer amplification for cloning. Once selected using the methodology described above, the enhancer sequence candidates were amplified by PCR from genomic DNA of cell lines (Jurkat T cell line or NK92 cells) and were then inserted in a cloning plasmid. To design PCR primers, a pair of primers of 18 to 22 nucleotides that have similar melting temperatures and that are spaced from the enhancer sequence of at least 10 nucleotides, in an effort to minimize the PCR amplicon size. PCR primers specificity was verified using UCSC genome browser tool. The primers were designed to add a restriction enzyme site and 6 bp randomly selected to allow an efficient cleavage (lowercase in Table II).

Table II lists all PCR primers (capital letters) designed to amplify the enhancer sequences from Jurkat T cell genomic DNA extracts, their apposed restriction site (in lowercase), and their PCR amplification conditions. The PCR was performed using the Q5 polymerase, according to the manufacturer's instructions (New England Biolabs, MA). The amplification conditions were the following:

denaturation: 98° C. for 30 sec;

amplification (35 cycles): 98° C. for 10 sec/Tm° C.* for 30 sec/72° C. for 30 sec; and extension: 2 min at 72° C.

*appropriate Tm for each reaction are indicated in Table I).

TABLE II

PCR amplification of enhancers sequences selected in sifico

| Enhancer name | PCR Primer sequences | Restriction sites | PCR conditions (Tm) |
|---|---|---|---|
| Tenh (Chr16-445) | atcatcgcggccgcGGGTCTGACGTGCTCTGT (SEQ ID NO: 1) tattcagcggccgcaCCTGGGTCAGTGCGTCA (SEQ ID NO: 56) | NotI NotI | 72° C. |
| NKspe-promoter (NK6) | attcggtaccGTGGGACACCAGTCATCTTA (SEQ ID NO: 2) gtacgaattcGAGAGCACCACACAGTCA (SEQ ID NO: 57) | KpnI EcoRI | 63° C. |
| NKspe-candidate (NK20) | atatgcggccgcGACCAGGTTTGGCCAATAGA (SEQ ID NO: 3) gcgactagtTGCCAGCACCCTGATTAAA (SEQ ID NO: 58) | NotI SpeI | 68° C. |
| T-NK spe candidate (Chr14-591) | atcaggatccGACACTTGTTCTGGGACCTA (SEQ ID NO: 4) cgcgcgaattcACCATACTGGTATATTCATTCTCTC (SEQ ID NO: 59) | BamHI EcoRI | 63° C. |
| NKspe-candidate (NK8) | cagggaattcGCTTACTTGTTAGCATCCCTCTCatacgc (SEQ ID NO: 5) ggccgcTGACTTAGTCCTAAAGCATATCTTGG (SEQ ID NO: 60) | EcoRI NotI | 66° C. |
| B-cell specific candidate | acggcaatcttggtaccCTCCAGTGCCAGATTTTTCAGG G (SEQ ID NO: 61) catgcgggtaccagtacgactagtGAACTGGCTGGGCTAT TTTGTGC (SEQ ID NO: 62) | KpnI SpeI | 60° C. |

The PCR product length was verified on agarose gel and purified using the QIAquick™ PCR Purification Kit (Qiagen, Germany). The PCR product was then digested with the corresponding restriction enzymes (see Table I) for cloning.

Cloning strategy to create a synthetic promoter from the in silico selected enhancer. To generate a specific promoter from the selected and PCR-amplified enhancer, the endogenous enhancer sequences were cloned upstream of a minimal promoter, namely the CMV minimal promoter (minCMV: GTAGGCGTGTACGGTGGGAGG TCTATATAAGCAGAGC TCGTTTAGTGAACCGTCA-GATC, SEQ ID NO:6)[5]. To validate the specificity of the synthetic promoter (enhancer+minCMV) through expression pattern assays, it was cloned upstream of a GFP reporter gene. To perform these tests, the backbone of the pENTR1a vector (Addgene, #11813-011) digested with the appropriate restriction enzymes was used and treated with recombinant shrimp alkaline phosphatase (rSAP, New England Biolabs, MA) to prevent self-ligation of the pENTR1a vector. A ligation reaction using T3 Ligase enzyme (New England Biolabs, MA) was performed to create the final plasmids.

Figure 1A:
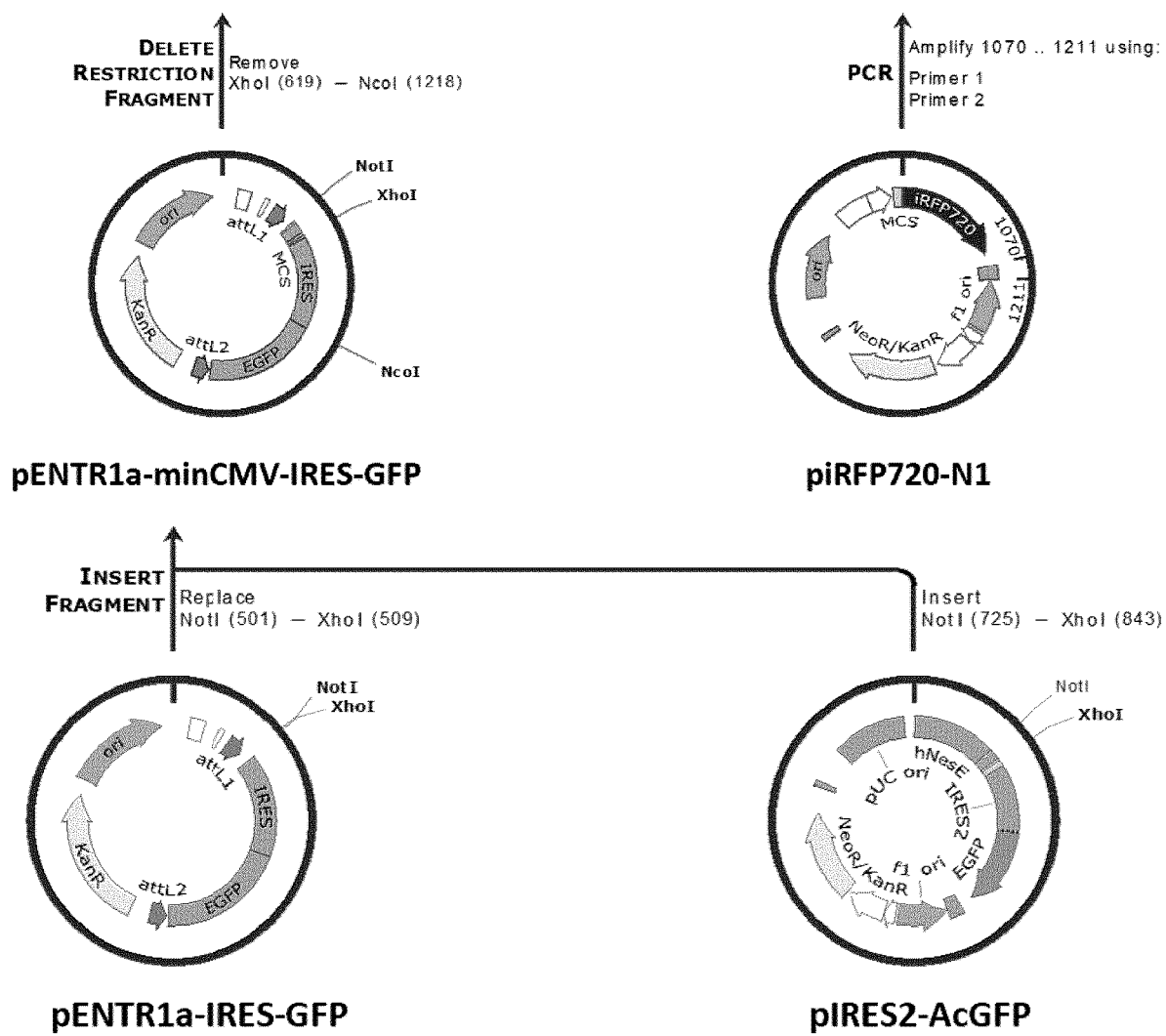
FIGS. 1A and 1B depict the cloning strategy used to create the T-cell specific-(Tspe)-promoter from Chr16-445. History is depicted from the bottom-up.
Figure 1B:
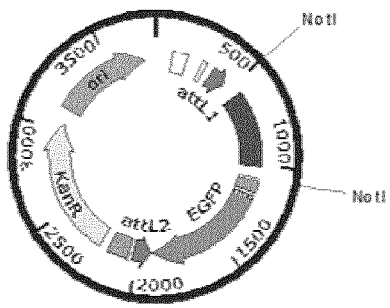
Figure 1B:
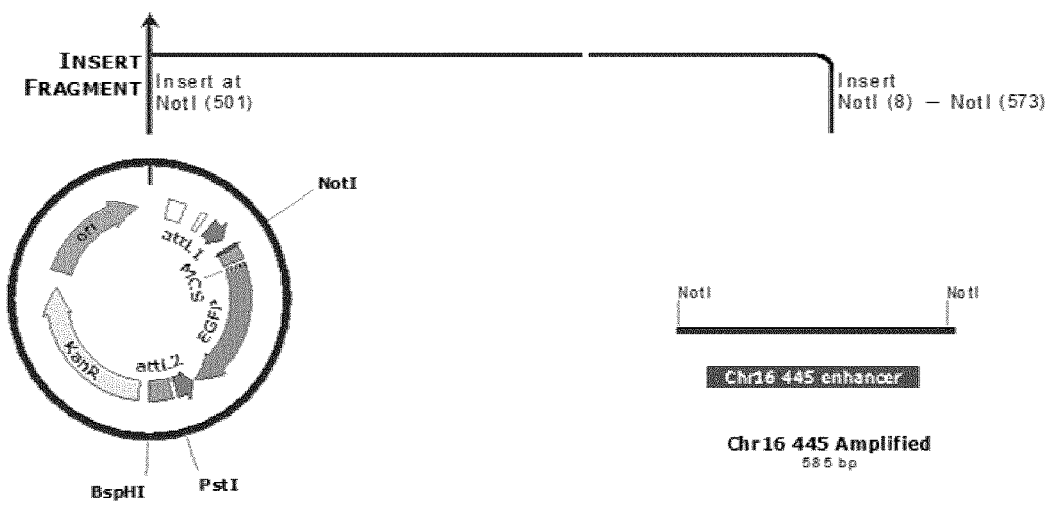
Figure 1B:
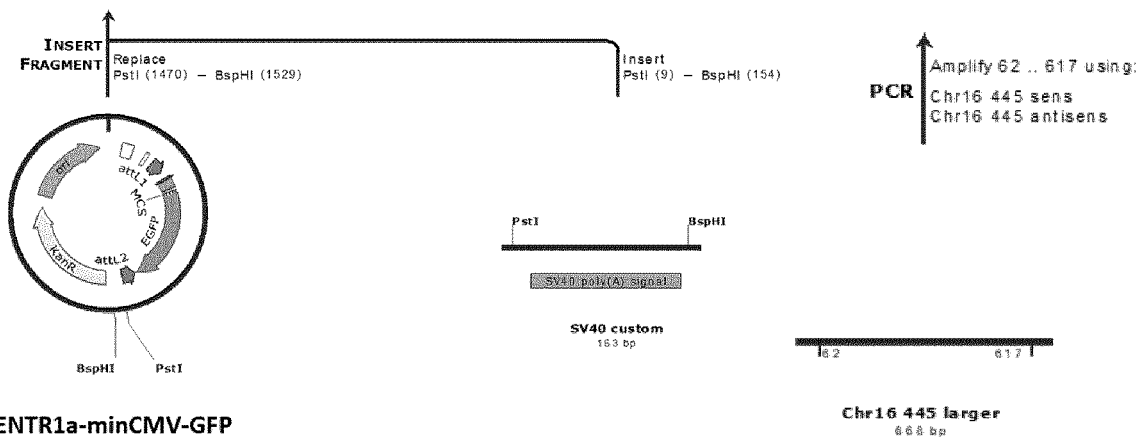

The detailed cloning strategy for the Tenh (Chr16-445) is illustrated in FIGS. 1A-B (history is depicted from the bottom-up). Briefly, pENTR1a-IRES-GFP was obtained by inserting the IRES-GFP sequence from pIRES2-AcGFP (ClonTech/Takara) in the pENTR1a gateway plasmid (Addgene, #11813-011). The minCMV was also excised from (ClonTech/Takara) and inserted in using NotI and XhoI enzyme to obtain the pENTR1a-minCMV-IRES-GFP. The IRES sequence was then removed by a digestion XhoI-NcoI, creating the pENTR1a-minCMV-GFP, in order to prevent this sequence to interfere with the synthetic promoter function and specificity. The SV40 poly(A) signal was inserted downstream of the GFP to stabilize the mRNA to create the pENTR1a-minCMV-GFP-SV40polyA. SV40 poly(A) sequence was amplified by PCR using the plasmid (Addgene #45461) as template. This pENTR1a-minCMV-GFP-SV40polyA plasmid was the plasmid used to clone all the enhancer sequences to perform the in vitro expression pattern analysis experiments. As described above, the PCR amplicon of the selected enhancer was digested using the appropriate restriction enzymes (listed in Table II) and inserted upstream of the minCMV sequence in pENTR1a-minCMV-GFP-SV40polyA. Plasmids were sequenced to ensure that the constructs correspond to the designed sequences.

Figure 2:
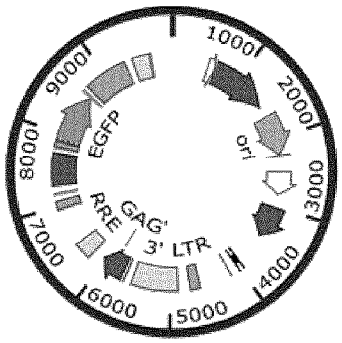
FIG. 2 depicts the cloning strategy used to create a plasmid to produce lentiviral particles for Tenh (Chr16-445). History is depicted from the bottom-up.
Figure 2:
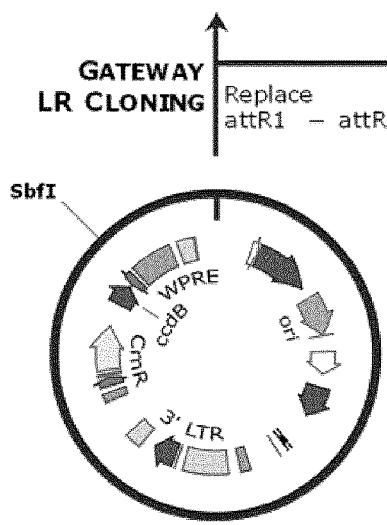
Figure 2:
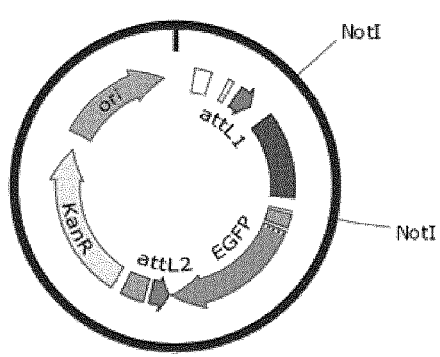

Lentiviral particles were then produced in order to perform expression pattern tests in vivo and/or in NK cells. To produce the particles, a pHR-SIN vector backbone was first used. The cloning strategy is depicted in FIG. 2. Briefly, a pHR-SIN-Dest vector, that is devoid of the spleen focus-forming virus (SFFV)-GFP sequence originally comprised within the pHR-SIN-SFFV-GFP vector (kindly given by Els Veroheyen, France), was generated by introducing a LR cloning sites (attB1/attB2) amplified from the pLenti CMV/TO Puro DEST (Addgene, #17293) to replace the SFFV-GFP fragment. This plasmid was used to insert the "ENH-minCMV-GFP-SV40polyA" sequence from the pENTR1a (described above) using the Gateway LR clonase kit (Invitrogen, CA), using manufacturer's instructions. To produce viral particles, this vector was co-transfected in HEK293T cells (ATCC, CRL-3216) along with 3 others, the p8.91 that provides packaging enzymes and 2 vectors, pHδ30 and pFδ24, coding for measles virus proteins that optimize CD34+ transduction[8,9]. For NK cells transfection, lentiviral particles with a baboon retroviral envelope glycoprotein (pBaEV vector, kindly given by Els Veroheyen) were produced[10].

In vitro Validation of Tenh (Chr16-445), NKspe (NK6) and Benh (B1, SEQ ID NO:23). To assess the specificity of the constructs, the vectors were transfected into human cell lines of various hematopoietic origin. First, for Tenh (Chr16-445), Jurkat T cells (T cell line, ATCC IB-152) and K-562 cells (erythroid myeloid cell line, CCL-243) were transfected. pENTR1a-Tenh-minCMV-GFP-SV40polyA was transfected using Lipofectamine™ 3000 (Invitrogen, CA) according to manufacturer's instructions. GFP signal was analyzed by flow cytometry (BD LSRII-Fortessa). It was observed that GFP was expressed only in Jurkat cells. These observations were then validated in primary human cells. Peripheral blood mononuclear cells (PBMC) (obtained from healthy controls with written consent, (REB #3527)) were nucleofected by electroporation using human monocyte nucleofector kit from Lonza, and the subpopulation expressing GFP was identified by flow cytometry. An anti-CD19 antibody was used to identify B cells (anti-CD19 PE clone H1B19 Biolegend), an anti-CD3 antibody was used to identify T cells (anti-CD3 PE clone HIT3a BD Pharmingen) and an anti-CD14 antibody was used to identify monocytes (anti-CD14 APC-Cy7, clone HCD14 Biolegend).

To test the specificity of the NKspe enhancer (NK6), a similar strategy was used. The vectors were transfected into cell lines of different hematopoietic origin with the pENTR1a-NK6-minCMV-GFP-SV40polyA. For this experiment, NK-92 (NK cell line, ATCC, CRL-2407), Jurkat (T cell line, ATCC IB-152), 697 (B-cell line, DSMZ ACC42) and K-562 (myeloid cell line, CCL-243) cells were transfected.

The B-cell specific enhancer (Benh, SEQ ID NO:23) capacity to induce the expression of a protein in a B cell line was tested by transducing Nalm6 cell line (B cell line, ATCC, CRL-3273) with BaEV-lentivirus particles coding for Benh-minCMV-GFP-SV40polyA. The GFP expression pattern was analyzed by flow cytometry, using an anti-CD19 antibody co-staining B cells (anti-CD19 PE clone HIB19 Biolegend).

In vivo validation of the T cell-specific (T-specific/Chr16-445), NK cell-specific (NK8) and B cell-specific promoter constructs. To assess if the GFP expression pattern was similar in vivo, human HSC isolated from cord blood (CD34 MicroBead Kit UtlraPure, Miltenyl Biotec, Germany) were transduced with measles or BaEV lentiviral particles coding either for the Tenh-minCMV-GFP-SV40polyA, Tenh-minCMV-CAR-CD22-SV40polyA, NK8-minCMV-GFP-SV40polyA or Benh-minCMV-GFP-SV40polyA. Cord bloods were obtained at the CHU Sainte-Justine Biobank of Cord Blood for research with the written consent of the mothers. Briefly, 200 µL of concentrated measles lentiviral particles were coated in 12-well plates containing RetroNectin (Takara Bio USA) for 4 hours at 37° C. 250,000 purified CD34+ HSC in 150 µL of StemSpan (StemCell, Canada) containing 5 nM Rapamycin and 3 µM CIHR99021 were added to maintain stemness[12]. The plate were then centrifuged for 1 hour at 1,000 g; after which 700 µL of StemSpan/Rapamycin/CIHR99021 media was added. Cells were cultured for 3 days and then injected in mice. NOD-scid IL2Rγ$^{null}$ (NSG mice) were acquired from Jackson laboratory (#005557), bred and maintained under specific pathogen-free conditions. Mice were preconditioned using gamma radiation with 2 Gy. $10^5$ of CD34+ cells that were in contact with the lentiviral particles were injected intravenously (IV) into 7-11 weeks old NSG mice.

To study the activity of the T-cell specific promoter in a more physiological context where the maturation of engineered T-progeny is taking place in a human thymus, a group of mice was also engrafted with 3 pieces of pre-cultured human thymus in the quadricep muscle[13]. Thymus pieces were harvested from cardiac surgery procedures (where the thymus is removed for the sake of the surgery) following approval of a research protocol by Sainte-Justine Hospital institutional review board (and written informed consent from donors). Pieces of thymus (2-5 mm$^3$) were cultured for 10 days on a GelFoam Sponge and an isopore membrane of 0.8-µm[13,14] in Ham's F-12 nutrient mix 1× medium (F12) supplemented with 0.025 M HEPES pH 7.5 and 10% fetal bovine serum (FBS) (Life Technologies).

Mice were bled regularly to monitor human cell reconstitution. Reconstitution and GFP expression were analyzed by flow cytometry using anti-mouse CD45-PerCP-Cy5.5 (clone 30F11), anti-human CD45-PE-Cy7 (clone H131), anti-human CD19-PE (clone HIB19), anti-human CD14-APC-Cy7 (clone HCD14), and anti-human CD3-APC (clone HIT3a) (all from Biolegend). Mice were maintained either in the animal facility of CHU Sainte-Justine Research Center.

Functional Validation of the T-specific promoter construct (T-specific/Chr16-445). To assess the potential therapeutic use of the Tenh-promoter, the eGFP sequence was replaced by a sequence coding for a CAR-CD33 or a CAR-CD22. CAR-CD33 was generated by synthesizing the ScFv sequence of gemtuzumab ozogamicin monoclonal antibody[15] (IDT Technologies) and cloning this sequence in a second-generation CAR construct (CD28-CD3ζ). The CAR-CD22 construct was based on the m971 ScFv sequence fused to 28z and BBz (Naso W et al. Blood. 2013; 121(7): 1165-1174). The CAR-GD2 construct was based on the 14g2a ScFv sequence (Louis C U et al., Blood. 2011; 118:6050-6) cloned in a second-generation CAR construct (CD28-CD3ζ). To produce VSVg lentiviral particles, the construct was cloned in a pHRSIN vector and particles were produced in HEK293 as described above.

Primary T cells were isolated from a 10-ml blood sample of a healthy donor. PBMCs were isolated by Ficoll™ and T cells were purified using the T cell enrichment kit (#19051, StemCell Technologies, Canada). Five hundred thousand (500,000) T cells were then put in culture in 900 μL of RPMI/10% FBS supplemented with 30 U/mL of human recombinant IL-2 and with Dynabeads in a 1:1 ratio (12.5 μL/well; Life Technologies). On the second day, 100 μL of concentrated lentiviral particles were added along with 8 μg/mL of protamin sulfate and culture for the next 6 following days. Recombinant human IL-2 (30 U/mL) was added every odder day. Expression of the CAR-CD33 on the surface of T cells was validated using a soluble CD33-Fc chimera protein (Siglec3/CD33 Fc R&D Systems, MI) and detected by a secondary staining using polyclonal anti-IgG PE (Jackson Immunoresearch) by flow cytometry. Similarly, the detection of CAR-CD22 expression was performed by incubating cells with 2 μl Siglec2(CD22)-Fc chimera (50 mg/ml, R&D) for 30 minutes at 4° C., washed and stained with anti-Fc-PE (Jackson Immune), anti-CD56-APC and anti-CD3-FITC (Biolegend). The detection of the CAR-GD2 was performed using anti-mouse Fab (Jackson Immune 115-065-006) for 30 minutes at 4° C., washed and then stained with a streptavidin-PE (Biolegend).

Functionality of CAR-CD33-transduced T cells was then evaluated in a cytotoxic assay against native CD33+ (ATCC #CCL-240) or CD33⁻ HL-60 cell line (generated using CRISP technology). Similarly, functionality of CAR-CD22-transduced T cells was tested in cytotoxic assay against RS4; 11 (B-ALL cell line expressing CD22, ATCC #CRL-1873), and functionality of CAR-GD2-transduced T cells was assessed against the GD2-expressing SK-N-DZ neuroblastoma cell line (ATCC, CRL-2149). Briefly, HL-60 (for CAR-CD33), RS4; 11 (for CAR-CD22) or SK-N-DZ (for CAR-GD2) target cells were stained with PKH26, a membrane labeling dye with long aliphatic tails which stably stains cell membrane. Following coincubation with effector T cells, the absolute count of living targets was calculated using CountBright™ Absolute Counting Beads (ThermoFisher) as well as the use of a viability dye (7-AAD). Briefly, 2×10⁶ target cells were washed twice in RPMI 1640 or D-PBS and resuspended in 100 μL of diluent C, then 100 μL of PKH26 (8 μM in diluent C) was added and cells were incubated 5 min at room temperature. The staining was stopped by adding FBS. Cells were then plated in different effector:target ratios (1:8, 1:4, 1:2, 1:1, 2:1, 4:1) and incubated for 24 hrs. After 24 hours, cells were harvested, stained with 7-AAD (BD Biosciences) and analyzed by flow cytometry. Cytotoxicity was calculated as follow: % Specific lysis=100−[(absolute count of PKH26⁺ 7-AAD⁻ targets after incubation with effector cells)/(absolute count of PKH26⁺ 7-AAD⁻ targets after incubation alone)×100].

Kinetic of expression during in vitro T-cell differentiation of a CAR under the T-specific promoter construct (T-specific/Chr16-445). First, human HSC isolated from cord blood (CD34 MicroBead Kit UtlraPure™, Miltenyl Biotec, Germany) were transduced with BaEV lentiviral particles coding for the Tenh-minCMV-CAR-CD22-SV40polyA as described above. To test the expression of CAR by CD34⁺ cells progeny, engineered-CD34⁺ cells have been co-cultured with OP9-DL4 cells or OP9 (without DL4) to induce the differentiation of CD34⁺ into T and B cells, respectively (La Motte-Mohs R N et al., Blood. 2005; 105(4):1431-9. Epub 2004 Oct. 19). Cells were co-cultured in a medium containing: alpha MEM (Gibco), 20% HyClone™ Characterized FBS GE Healthcare), GlutaMAX-I™, PenStrep, 5 ng/mL IL-7 (Perpotech), 5 ng/mL FLT-3L (Peprotech) and 800 uM L-Ascorbic acid 2-phosphate (Sigma). Cells were co-cultured for 2 weeks and medium was changed twice a week, and feeder cells (OP9 or OP9-DL4) were change each week. CAR expression on different sub-population was evaluated by flow cytometry using two antibody panels: 1) anti-CD1a-BV421 (clone H149, Biolegend), anti-CD7-FITC (clone M-T701, BD Biosciences), anti-CD45-PeCy7 (clone H130, Biolegend), anti-CD34-APC (clone 581, Biolegend), anti-CD19-APC-Cy7 (clone H1819, Biolegend); and 2) anti-CD4-APC-Cy7 (clone RPA-T4, Biolegend), anti-CD8-APC (RPA-T8, BD Biosciences), anti-CD3-FITC (clone UCHT1, Biolegend), anti-CD45-PeCy7 (clone H130, Biolegend). In both panels, the detection of CAR-CD22 expression was performed by incubating cells with 2 μl Siglec2(CD22)-Fc chimera (50 mg/ml, R&D) for 30 minutes at 4° C., washed and stained with anti-Fc-PE (Jackson Immune), and DAPI was used as a viability staining.

Assessment of the specificity of the NK8 promoter. The specificity of the NK8 promoter was also assessed in the OP9 co-culture system, in conditions favoring NK cell differentiation (Beck R C et al., Biol Blood Marrow Transplant. 2009, 15(9):1026-37). Human HSC isolated from cord blood (CD34 MicroBead Kit UtlraPure™, Miltenyl Biotec, Germany) were transduced with BaEV lentiviral particles coding for the NK8-minCMV-GFP-SV40polyA as described above. Transduced cells were co-cultured with OP9 cells was performed as described above with the addition of IL-15 (10 ng/mL) for the differentiation of NK cells. GFP expression was evaluated by flow cytometry. Co-staining of anti-CD56, anti-CD45, anti-CD4 and anti-CD8 (Biolegend) was performed to identify cell subpopulations.

Example 2: Promoter Sequences Tested and Validated

The first step was to identify a specific enhancer to create a synthetic promoter for T cells. 5 enhancers sequence candidates that fulfilled the above-described criteria were identified (Chr16-445 (SEQ ID NO:7); Chr 14-591 (SEQ ID NO:13); Chr 8-438 (SEQ ID NO:8); Chr 8-230 (SEQ ID NO:9); Chr 12-199 (SEQ ID NO:10). Of those, the Chr16-445 sequence was thoroughly studied as each validation step was conclusive. This sequence, detailed in Table III, contains highly-repeated motifs, and is only significantly overexpressed in T cells (with a tags/million score of 0.511 in T cells). It is located in Chromosome 16 (position 88536883-88537327) and is 445-nucleotide long. Within 2.5 kb upstream of the enhancer sequence, 23 putative binding sites for transcription factors such as Gata1, POLR2A, POU2F2 and MYC were identified, providing compelling evidence that it is located in a transcriptionally active region.

Similarly, 2 potentially NK-specific enhancer sequences were selected (NK6 and NK20—see Table IIIa), of which one (NK6) has resulted in a coherent pattern of expression in preliminary data. This sequence is located in Chromosome 6, is 379-nucleotide long and also contains highly repeated motifs. It was only significantly over-expressed in NK cells (tag score of 0.719 in NK cells). This sequence has 19 transcription factor binding site within less than 2 kb of the sequence. A second NK-specific candidate (NK20) located on Chromosome 20 has a tag score of 1.823 in NK cells.

An enhancer sequence that would induce the expression of a transgene in both T and NK cells could be interesting in the context of gene therapy of cytotoxic cells. A putative T and NK cell-specific promoter sequence was identified on Chromosome 14, position 61804524 to 61805115 (591 nucleotides). Its tags/million score is high in T cells (6.629) and in NK cells (3.327), with a significative expression only in these 2 cell subtypes. Four transcription binding sites—RUNX3, GATA2, FOS and JUN—are located within the enhancer sequence itself.

Also, 4 putative specific enhancers for B cells located on chromosomes 1, 3, 10 and 13 that matched the selection criteria were identified (B-spe candidates #1, 2, 3 and 4—see Table IIIa).

Finally, several other candidate enhancers for different cell type(s) were also identified (Table IIIb).

TABLE IIIa

Characteristics of candidate enhancer sequences for T cells, NK cells, T/NK cells and B cells identified herein

| Name | Position (hg38) | Sequence | Validation/ Characteristics |
|---|---|---|---|
| T enh (T-spe promoter/ Chr16-445) | chr16: 88536883-88537327 | CTGGTGGTGTGGAGGGCCGGGTGGTGA CACTCAGTGACAGGTGAGGATGTGGCAC GGTGTGGAGGGCCGGGTGGTGACGCTG AGTGACAGGTGAGGATGTGGCACGGTGT GGAGGGCCGGGTGGTGACGCTGAGTGA CAGGTGAGGATGTGGCACGGTGTGGAG GGCCGGGTGGTGACGCTGAGTGACAGG TGAGGATGTGGCACGGTGTGGAGGGCC GGGTGGTGACGCTGAGTGACAGGTGAG GATGTGGCACGGTGTGGAGGGCCGGGT GGTGACGCTGAGTGACACGTGAGGATGT GGCACGGTGTGGAGGGCCGGGTGGTGA CGCTGAGTGACAGGTGAGGATGTGGCA CGGTGTGGAGGGCCGGGTGGTGACGCT GAGTGACAGGTGAGGATGTGGCATAGG GAAACACATCCTCGCCGAGCGCACAGTG GGAGCTCCG (SEQ ID NO: 7) | T-specificity confirmed in vitro and in vivo Highly repeated motifs Tags/million = 0.511 in T cells Only significantly overexpressed in T cells |
| T-NK spe candidate (Chr8-438) | chr8: 101819182-101819619 | CTGAGGACTTCTAGCTCTTCCTGGATCCT TATATGCCCATTTGCTATTGTAAATAGCT ATATGACGTTGTGATACTATTCCAAACCC TAGTCATAGCAACCACATACCTAATAGCC AAGGGATAACCATACTATCTTCCCTTTCT GAAGAACCTTTCAGCAAAAGATTTCAGG GAATTTTACCAAGAAAACCATCCCATCCC CTCCTCCTTCCATTTGACAGGTGGAGAA GTGAGGCACAGTGAAGCCAGAGGAGCC TGGTCAGACGGTGAGTCAGAAGTAGAGC AGGGCTGCACCTGGTGACACCTATTTCC TCCCTTGTGGTTTGGCCCCTGCCTCATA GGCTTCCTGGAAAGGTGTAGCTTCTTCA TGGCTTACTTGTTGAGTAAACACTGCTAT GAGCTTTCAAATATTTCCCTAGGTTGCAG GAGGTTGTGTC (SEQ ID NO: 8) | Significantly over-expressed only in T and NK cells Tags/million = 3.082 in T cells Tags/million = 2.195 in NK cells |
| T-spe candidate (Chr8-230) | chr8: 2153112-2153543 | CTAAAAACAAACAAAGCCAAAAAACCATA GCACTTTATTTTAAGGATATTTCTACTTTA ATCCATAAATGGTTTCTAGTTCTTGTATTA ATGGCGACATCATGTTCCATGTTTTCATG AACTGTGATTTATCAGAGAAGCCCTTGCA ACGGTGATCTAGGTTGTGTCATCGCTTCT GCGTAACAGCAAGGCAAAGCTGCGGATT TATCGCCGTTCTACCCAGGTTTCCTGTTG ATTACGGCAGGGTTTGAGGTGCGGTCCC TGGTGTTTCATCATGACAAGTGGAGGTTT GCAGGAGAACTTCATAACCATCTGCAGA AAAGGTGAAGTCACATCTTGAGACCAGC TCTAGATATGTTACCGATGGGCTAATGGT TTTGATGTAAAATAAGTAAAAACATTAAA GGGCTAGAAGAAGCCAGAGGAAAAGTCA (SEQ ID NO: 9) | Significantly over-expressed only in T cells Tags/million = 1.348 in T cells |
| T-NK spe candidate (Chr12-199) | chr12: 9106762-9106960 | GTGAAATAAGACACACACAGAAAGAAAA ATATGATATGATATCGGTTGTATGTGGAG TCTTGAAAAAAATCACCATAGAAACAGTG TAGGAAGATGGTTACCAGGGGCGGGGT AGGGGAAATGGGAAGATGTAGGTCAAAA GGTACGAAGTTGCGGTTAGATTCTAATGT | Significantly over-expressed only in T and NK cells Tags/million = 1.294 in T cells Tags/million = 1.551 |

TABLE IIIa-continued

Characteristics of candidate enhancer sequences for T cells, NK cells, T/NK cells and B cells identified herein

| Name | Position (hg38) | Sequence | Validation/ Characteristics |
|---|---|---|---|
| | | TCTAGTGTGTAACATAAGGACTATAGTTA (SEQ ID NO: 10) | in NK cells |
| NKspe-promoter (NK6) | chr6: 168682215-168682594 | GCACATTCATCTCTCTGAGAAACACCTCC CTATGCTGGGAAATGTGAAAGCAGGTGG GACACCAGTCATCTTAGTACATCACATTG TCACTGCCGCGAATGTGTGGGACACCCA TCATCTTACCACATCACATCGTCACTGCC GCGAACGTGTGGGACACCCATCATCTTA CCACATCACATCGTCACTGCCACGAACG TGTGGGACACCCATCATCTTACCACATCA CATCGTCACTGCCGCGAACGTGTGGGAC ACCCATCATCTTACCACATCACATCGTCA CTGCCGCGAACGTGTGGGACACCCATCA TCTTACCACATCACATCGTCACTGCCGC GAACGTGTGGGACACCCATCATCTTACC ACATCACATCGTCACTGCGTGAATGTTTT TCTGAATACATCACACATTTGGCTCCATA AAATCTGTTTTCTAATCTACTTTTTAACTT AGTATGTTGGCCTCAACTTTGCACTTTAT TTTTCTTCGTGACTGTGTGGTGCTCTCCT CTCTGGAGGTGCCTTCACTGAGGCTGCA TTGAAGGGCTGTGTGGGCCAGCGAGTG CTGTGGTCGG (SEQ ID NO: 11) | Evidences of NK specificity in vitro Highly repeated motifs Tags/million: 0.719 in NK cells Significantly over-expressed only in NK cells |
| NKspe-candidate (NK20) | chr20: 24013863-24014201 | CTCTTCATTGACCCTGAGTTTGACCAGGT TTGGCCAATAGAAGTCAGAGGAAGTGAC AGGTGCCAGTTACAAGAAGTTCCACAAC CCCTTTTAGAAATCAACTAAACCACTGTG TGAATAAAGCCAGGTTAGCCTGCTGGAG AATGAGGCCCAATTGCTCCCATCATCTCA CATGACAGCCAACCAACCACCAGTCATG TGACTGAGGTCATCTTGGACCAGCCAAA TTCCAACCAACCTTTTCAGTAGACCTCAG ACACATGAACAAACCCAACTAAGATCAAC CAACCCTAGACAGTTCTGCAGAGTTGCC CAGTAACACACAGAATCATGACCAATAAT AAATGTGTACTGTTTGAAGTTGCCACATT GTTAAGTGGTTTGTTATGCCACAAAAACT AACTGACACATCAACTCTGAAACCTCCTT GGTTTAATCAGGGTGCTGGCAGGTACGG AGCAACTGTGCCCAGGGTAACATTACTT AGTCTCAGAATCATAATTAATTAAATTGC AAGTGACAGAAATATAATAAAATCT (SEQ ID NO: 12) | Tags/million: 1.823 in NK cells Significantly over-expressed only in NK cells |
| T-NK spe candidate (Chr14-591) | chr14: 61804524-61805115 | TGATTTTAAGTGAAAGGTTTCTGAACTGT ATATATACAATATTTCAGAACAGTAATTTC CTTTGCTTCATAGTACGGCACAACAGTGT TTGCACTTGATGTTTAGCGTAGCCTTGGT TTTGGTTGTTCAGAAGCCTTTGTTAGCTC TTTGGTTGTGCCAAGAATATATTGTTTTT GAGTCTCCTTGCCGGGCCTCCTCGCCTT CTTGTCATGCACATCCTGTACCTGGGTT GTGGTTGTATTGATTTGCTGGGGCGCTG CTGTTGCAAATGTCTGGAGTGAATGAGA ATGTGTTTGTGGGTGTCTGCCCTCACCTT GGCCACTGATCTGCTTTCAGCCCTGAAG TACTGCCATCTGCATGAACATTAGGGAC CCCCAGCCTCCCCCACCACTTAGTAAAG TACCCTGCACATGTTTGGGATTCAGGAA ATGTTTGTAGAAAGGAAAAATTCCTTATC ATTCCTTACCATTCTCTGTCTTGAGTCTG AGTCATGATTCAAACACTTTTGCTAAAAG GTTTTCGCTTGAAAAATTCATATTCAGGT ACAGATTTACTTTTTTTTGGTGTGTGTGA GTTAAGAGCTGCCTCAG (SEQ ID NO: 13) | Tags/millions: 6.629 in Tcells; 3.327 in NK cells Significantly over-expressed only in T and NK cells |
| NKspe-candidate (NK8) | chr8: 103109879-103110286 | ATCAGAAGTTGCGTGGGTCATGAAGCC CAAGGCCAGCAGTTCTGGATGCCTCCA TGAAGCTGGATATTGCTTACTTGTTAGC ATCCCTCTCTGGCAATCATCAATAACCT CTTTTCAAAAGTACCTCCTTATACAAGA | Tags/million: 31.336 in NK cells; 2.013 in basophil; 1.503 in T cells; 0.835 in monocytes |

TABLE IIIa-continued

Characteristics of candidate enhancer sequences for T cells, NK cells, T/NK cells and B cells identified herein

| Name | Position (hg38) | Sequence | Validation/ Characteristics |
|---|---|---|---|
| | | CTCTTATCAACTGATTTCATCATTTTTAG CACTGAAACCTTGGTCTTCCTGCTCTCT GCTCTGACAGCATCTCTCTGATAACCTG AGAAATCAGAGTTTCACCCCTGAAACTA AACAGGCCATTATTTCCTAATTTTAAATG ATGACATGACAAGCCTTCACCCTATCTG TTTCTTATTTCCTTGAACTCTCCCACCCT CACCAGCAGCCAACACAAATCACAACG CAATGCAAAGGCCAGGCCACAGAACAC GCTGTGAATCGACAGTTTCAGAAGACGT CATTCACACAATGTGCAAGGCACTTCCT GCACAGCCATCTCTGTGCCCCTGCAAA GGGCATGTGGCATGAGGCAGTAAAATA AGTATAGTCTGTGTTTGGGTATGAAAGG TGGTGGGTGGGCGTGAATACATCCAA GATATGCTTTAGGACTAAGTCAAAAGAG AACTGAGAGTGAGAAAGAAGATTG (SEQ ID NO: 14) | Significantly over-expressed in NK, basophils, T cells and monocytes |
| B-spe candidate #1 (B1) | chr1: 220219915-220220218 | CTGACAAGATGCAAGCTCATCATTTTGT TTTGTGTCATAAGGGCATTTGCCTACTA ATTAGCGTTTTGGAAAACTTCCCCAATA ATGGGGCCCACAGTCTCTAACACTGCC CCTTTGAAGCTAGTGATCCAAAAATAAT ATCATTTGACAAGGTAATTTCCCAAGCC ACGCCTGAAATGTAAAACAAAAAAAGCA CCTCACTGCTTAAAGGTGCTCCACCAG GGACCTTGGGTTTTCCACCAAAACTTGC CTCCCCCACCCTGTTACTAAAGTTGACA CTGAATTTGCCTGCAGTCTCCCCCA (SEQ ID NO: 23) | RAB3GAP2 Tags/million: 5.001 in B cells Negligible tags in other primary blood cell types |
| B-spe candidate #2 (B3) | chr3: 112216852-112217043 | TGGGCATGGTGGCTCATACCTGTAATC CTAGCACTTTGGGAGGCTGAGGCAGGT GGATCACTTGAGGTCAGGAGCTCCAGA CCAGCCTGCCCAACATGCATTGCATCC ATAGCTTGGCTGACTTTCTTAAAAAACA GGTTGATGGCAAGAAAAGAGAACTGAG TAGATGTTATAAATAGTTAAGTACAAATC TATCACTACTTCTTGCGAAAATGCTCAG GCTGCCACACTGATGATGAATAGATAGC TCGTTCTTCCCAAACTGAGTGCAGTAGA GTGTTGCAGTGCTCAGTTGGGTAGGAC AGATGTTGGATAATTGGGGTTATCCAAC ATCTCTACTAAAAATACAAAAATTAGCTG TGCGTGGTGGAAGGTGCCTGTAATCCC AGCTA (SEQ ID NO: 15) | Tags/million: 2.541 in B cells Significantly overrepresented in B cells |
| B-spe candidate #3 (B10) | chr10: 49879351-49879455 | AAGGAGGAATTGCTGTCTGAGAGGGTA TTTTGTTCCCCAGTGACTGAGGGCAGG GCAGGGGCAGGGAAGGCTTCCCCTCTC TTCTGGCCCTAGAGGCCCTGTAAATGC ACTGTGCAGTCACTGACGTGCCCTCAG GCAGGGCCCTGGCGGGAAGGGGGCTG TTCCAGGTCTACCAGCTTCACACCCTTA TTCTATTGAATTCTCATGAAAACAAAATC TGTGAAACAGCTGTGATCTTCATTTTCT GATGAGGGAACAGAGCCTCCGTGCCCC CGAGATCACTGGTATGACTCCAAAGATT TTCC (SEQ ID NO: 16) | Tags/million: 1.993 in B cells Significantly overrepresented in B cells |
| B-spe candidate #4 (B13) | chr14: 74868763-74868996 | GACTCACACCTTTGGCCACTGACCCCT GCCCCACCTTCTGAGTGGGGTTCAGGG ACTGTGCTGAGTCTGTCTCTGGGAAGC AGCAGGGTGCAGGGGCACACTGATGAG TGGTGCATGTGCCCAGGGGCAACATCA GAGCCGTTTAGCCACCAGGGCAGTCAG GCATGGACAGACGCATTTGGGAGGGGG CGGGGCCCTGTGTCAGCTGTTAACACT TCAGTTCCTGAAGCAGAAGAGTCTGGA GTTCTGGGGAGGGGCCAGGGAGGCAG GAGAGGGAAACACTGGGAGGGTTTAGG GCTTGGCCTGTTTATCAACTACTGTGGA AGTATTTTCACTGTTCTGACAATCCCTG | Tags/million: 2.534 in B cells Significantly overrepresented in B cells |

TABLE IIIa-continued

Characteristics of candidate enhancer sequences for T cells, NK cells, T/NK cells and B cells identified herein

| Name | Position (hg38) | Sequence | Validation/ Characteristics |
|---|---|---|---|
| | | CAACTATGTCCATGGACCTGCTGTCTAT CCGCCCTGTTCATCGGGAGGAAGAGAT GGAGAAGGCTGCCGGGGTTCTGGGAG T (SEQ ID NO: 17) | |

TABLE IIIb

Characteristics of candidate enhancer sequences for various cell types identified herein

| Cell Specificity | Coordinates (hg38) | Sequence | Genome Location |
|---|---|---|---|
| T/NK | chr1: 167489187-167489883 | CCAACCCCCCTTCCCCACCCCAAACTCTGCTTATA GGTTCTTATATGATAATTTAAACTATATATGATATTA AATTAGCACTCCAATAGCAAAAATAAAGTGTTCCC ACATCACCTTCTTTGAAAATATTTATTTAAATAGGA TGAAATGTTATTGAGGGCTTTTGTGTCTAGAAACA GGGTTAATTAAAGATTTCCTGCCTGCTTTGTGGGT AGGTGACACTCTCATTGAGATAGCAGCAATGCCCT ATTTAGTGGTCTCTCAGCTTTCTTTCTATTCATCTG GTTTGGTAGTGGAATTCCATGGGAAGTTTGACCCT ATTCAGTGATGAGAGAAGCAAAATACTGTTGTTCA CCTAGAGGCTGTTTGCTCAGAAAAACAGGGTGTCA GAGACATGGGACGCAAACCCAGAGTGACATAGCG CAGGGACTTGGCTCACTTTTCTGAGATCTGTAAAA TGTGATGTGACTGGCTCTCAGAAAGGAGGCTGAA GGGTTCCTGCCCGATTGGTTTTCAAAGGGCAAGA GCCCCGCTGCTGAGGAGCTGCGGCTTTGTTAGAC AAAAGCCCAGGGCAGCCCCCTCCTGGGCTCAGCG TTTTCCCCACCTCCCCCTTTCTCACAGGCGGTTTC CCTGAAATGAAAGAACTGTGATGCATTTGCGCCTT CAAAAGCAGTTTTTAAAATGCATTAAACCCA (SEQ ID NO: 18) | CD247 |
| T/NK | chr1: 167492555-167492938 | TAGCAGGGAGGGGAATTTTCCTTTCTGGTCACGTA GGCTGCTGTCTTCGGCTTCGATTCGTAAGCCACCT CCCAAGCCCCCATTAGCCCCAGGTAGGGGACATC CCATCCCCCTAAACCTCCTTCTTGAACTGACAGTT CACCCCTAGAAGGAGGTGGGAAACCACTCAGATC CATCTCAAAGGGATGCCTACCAGGGTAGGTGTGT GGGAGGAAGGCTGAGCCCATGCTGTGTTCAGGG GCCCCCCCAGAAGGTGTCAGCCTGGAGGAACATG CCCCACAGTTATAAAAGGCATCATTCCAGGAGCTA TCATGGCGTCTGCTAGGGGCAGAGAGGAAGGGG AGGCAGGAAAGGGGCTGAGTATTTTGGGGCTGTA TGCTTAT (SEQ ID NO: 19) | CD247 |
| T/NK | chr1: 167516527-167516891 | GGCCTTTCCTCCGGGGAGACTGTGGAGGTGTCCC CTCAGGCAGCAAAAGCACCATCGCAGCCCTCGGT GTCAAGGCCTCTCTGAGTCGCGCTTTGCCTTACC GTACCTCGTTTCTGGGCTAGGATATTTTGAAACAC TTTTGTCTATTAGCTTTATCTAAAATAGCTAAAATAT CAGTCTCCATAGAGGCAAAGTAAGTGGCACTGAG AAGCAAAAAATCCAGCCAATGTGCAGTTTTCTCCT CCTGCCCCCTATTTGTGGAAATGAGGCACGGCCC CCATCTTGTCTGCTGGGTGGGGTTCTGTTTACCAC GCTTGGCAGCCACCGCCACCCAACAATCTTTCATT TTTCTTTCTAACTTCAC (SEQ ID NO: 20) | CD247 |
| T/NK | chr1: 167516973-167517468 | GAGCTCCCTGGTGTGGTGTCTCAAGCCTGAAGCT CAGAGGCTGGAGCTATTGCCCCTGGCTGTCTCCC CTGAAGTCACTAAATTCCAGCGTTCTGGGTCCCCT TGTCCCCAGCACACAAGGATGGGCTGCTCTGAGC AAGCTCAGGCACCCTCACTCTGCCACACTGTGTGT GTGACTTAGACCCCACAAGGCTTTTCTGAGAAAAC AGCTGTGACCTGACAGAAACCCCTGCAGCTGCAC GGGCCTCAGAATCCCCCGAGGCGCTGGCCCGGG CTGTGCCTGGCTCCCTGGTGGGAGCAGAAGTGCC CATGGCCTCTCCTGCCCTCCCAACAGGGCCCCTA AACAAATTCCCACACCCAGGTGAGTTACCAGGAG | CD247 |

TABLE IIIb-continued

Characteristics of candidate enhancer sequences for various cell types identified herein

| Cell Specificity | Coordinates (hg38) | Sequence | Genome Location |
|---|---|---|---|
| | | CGATCAGGTGGGCCGAGGACATTTGCTTGCTTCA CCTTCCCTGTTTCTTTAGATTGAAATTCAGCCTGCC CCACTTCTCAGGAAGATGCCACGAGGCTGATCCC CCTGAGCAGTTTGTC (SEQ ID NO: 21) | |
| CD4/NK | chr1: 193458645-193459063 | TGGCTGGCAATCCTTTTTAGCCATCATATATAATAG CTATCTAACTCTTGATTTTTGTGTAACATAAAGCGG TGTTTCATAATGAATCATTTTGTCTGTTCGTGTTCA AGTGCCCTATCTATTCTATCATTTGAAAAGCTAGTT ATGATAGTATGGTTTCAATTGTCAGACATTCTCTTT ATTCTAAAAAAATAGGTTGACCCACATTTAGATGTT TTCCTACTCAAAGGACTTTGAAAGAACTTTTTATGT AACACTTAGTCATTGCCCTTTTCACAGTCCCTCTTC CGCTGCTTCTAATTAGGCTCTTTGGTAGCTGGAAT CGTCATTTCCCTGGCATGAAGGCACATGGTACCAA CTTGTTGGTTGCTTGATTTGGAGGGTCAAATATGG ACTTGCTTCTTTTGGTCTACCTTGC (SEQ ID NO: 22) | intergenic |
| B-cell | chr1: 220219915-220220218 | CTGACAAGATGCAAGCTCATCATTTTGTTTTGTGTC ATAAGGGCATTTGCCTACTAATTAGCGTTTTGGAA AACTTCCCCAATAATGGGGCCCACAGTCTCTAACA CTGCCCCTTTGAAGCTAGTGATCCAAAAATAATAT CATTTGACAAGGTAATTTCCCAAGCCACGCCTGAA ATGTAAAACAAAAAAAGCACCTCACTGCTTAAAGG TGCTCCACCAGGGACCTTGGGTTTTCCACCAAAAC TTGCCTCCCCCACCCTGTTACTAAAGTTGACACTG AATTTGCCTGCAGTCTCCCCCA (SEQ ID NO: 23) | RAB3GAP2 |
| T/NK | chr10: 6530291-6530474 | TGAGCTGTCGCCCTTGGGTACACCAGTAGCAAAA ACACTCCTGTCCTCCTATGCTGCTGTGACACCACA CCCCACTTCCTCCCGCGGGCGTGTGACACTTTTC AAAGAAAATACAGTATTTGGTAGTATCAATACAGCA AGCGGAAGCAGCAGTGCTCAGTCCGCAGTGAGCT AACAGTTTTA (SEQ ID NO: 24) | PRKCQ |
| T/NK | chr10: 6558358-6558616 | CAGACATACAGTACTATTTTGTTTTTTTTAAAAAAG GCTTAGTAAACACAAAGAGGAGTTACATACTGAAA CCCACAGCTGATTTAATTTGCAAAACCACAGCGTT AGCTTGACTAAAGTAAAGATGACACAGATAAAATG CAACCAGAAAACTGAGATAAAAGATACAGGATAAA TAACTTAAGCTGATGGTTTAGCAAGCAAACATCAT GGGTGTAACATGAAGATCTGAGAAGTGACTTCGGT CCAGGAAACTCA (SEQ ID NO: 25) | PRKCQ |
| T/NK | chr10: 6592128-6592406 | CTAAAAATTACACCTTCTGCTCACTCTAATTTATTG CTGTAGAAGAAAGAATAAGTGAGATATTTCCATTTC TAGTGACAGGTGGCTGGCACTTTGAAACCTTCCAT TTCATTACTCACCTTAATGTTTTCACTAAAACACAT GTGGTTTTCAAACACAGGAAGGAAAACATGGTAAC CTGTGGTTACAATTTCCACTAGAAAATAGAAAAGG TGTAGGTCAGAAAGAATGTTTGTGGGGTGTTCCTT TTTTACTTTAAACATGAAAACCCATGTCAG (SEQ ID NO: 26) | PRKCQ |
| T | chr14: 99250860-99251000 | TTAAGAGAAAAAAAAAACACCCATTTATGTGACCA GTATTGTCTGTCTTTTTTTTAATCCAATAAAACTTTC AACTACAATCGGTGCTGATGTCACCATGTTAGCGG CACACACTCTTGACTCTGGTTTGCACAGTTCAC (SEQ ID NO: 27) | BCL11B |
| T/NK | chr14: 99253442-99253634 | CGGCGGAGGAGGGAAAGCCGAGCGCCAGGAAAA GCTCCTATTTGCAGCACACCTACCCCCACCGTGTG CCAGGCACTCATCATAAATGTCACAATGACAGATG AGGAAACCGCGGCTCAGAAGGTCAAGTGGCTGCC GGAGGCTGGCAGGGAGCAGGGTGGGGCTCTGAC TCGGGCTGTGTTCTTTCCCACA (SEQ ID NO: 28) | BCL11B |
| T/NK | chr14: 99259222-99259750 | TGAAAACCACAGAGGAACGGCGAGAAGGAATGGG AGGGAGGAAAATACATTCCGTGGCAGTGAAGTTAT TGAAGTGCCAGAGCCAAAGAACAGATAATTTAAGG AAAAAATTCTGTGGCATCTCCCATCCTACACATAAA TCACTGTTCTCTATTTTCTGAACACGAGCCTATGCA GGGCCTAGGAGAGTCCATGTGTGAAACTGAATAC | BCL11B |

TABLE IIIb-continued

Characteristics of candidate enhancer sequences for various cell types identified herein

| Cell Specificity | Coordinates (hg38) | Sequence | Genome Location |
|---|---|---|---|
| | | AGAATATACGACGATGTAAGACGTACAACGCGCAC GTATGAACTATGTGTGAATAGGTAGCGACGTAGGT ATCGCTGAGAAGAGAAACTACAATTTGAGATCCCA CCTGTGGTTACAGAAAAGCAGACAGAGCCCTCGA TGAATTAAATGCAGAATGCATCAGAAATGTGGCAG TACAGAAACGCCCCGCAGACGAGGAAATCCTAAA TCTGTTGTCTGCATCTCTCTAAGAAAAAGAACCTA CAAGGTAAAGAAACAGTCCTCACAAAGCCGGTCC CAGAAACCATTAATTACACTTTAGAAAGAAATAGGA GTTTA (SEQ ID NO: 29) | |
| T/NK | chr14: 99260500-99261397 | AATTTCAAACTCATTTTCTAATTCAAAAGAAACACA GATGAATTTAAAAATTAGCAGAGGTCACACGTGCC TGTTCGCAAGCACCCCTCCTCCTCAGCTTCGTCTT TTGCCAAGACTATGTACCAGCACTTTTTCCTTTCTC TCCTCTTTTTTTTATTTTTTTATTTTTGGTAACATCT GGTATTCTTTCCTTTTTTTGGCAGTCTCTGCCTTTT CACTTTCCTCATGCAGCAGCCCTGCGAGCCCCCG TAATTGAGTTTGAAGGTGTCCAAAGCCGTTTGCTG TGCTGCAGCTCTGATTTCTGCGTCAAGTCCTAACA GCCAACCAACCTGGGAGCCAGGCCCTGTTGGCGT CCCCGAGACAGCCCCGGGATTATCCAGGCCTCCA GGGCTCAGTTCTGAGCTGGGATCTCCACGTCCCA GACCAGAGATCCAACTCACTGCCTCTAAGGGAGT CTGGGAGGAAAAGAAACAAACAAAAAATATCTCCT TCCCCTCCCACTTTCAGCGTTGAAAGTTAAACCCC TGAGATGACAGGGTGTTCACCCGATTCCAAAGAAC GGGGTTTCCTCTCCCCACCACCCAGGCTGTGGCG CTGTGCCTTGGCCTGCTGTGTGCGACACTTCCCA GGAAGGTAGCAAGGTCACCCTCAACATCAGGCAG CAGAGTCACCCCCAGCCCCAAATTTCTGGGTCAG AGTAAGTGGACCAAGTGGGCCTGAAAGCTCACGT TCAAGGCCTTTGTAGACACCCCCAAAGACTGTGGT TTCACTTCCGCTGGCAGGCAGATACCAAGCTAGG CGTGTAGGGTGCCTGCATATGTGTGCATGTGTCC CTCCTTAGAACTGTATCGATAATGGAAGAAATAAA AGGAGAAAGCCAAGCCCTGGGAAGGGCAA (SEQ ID NO: 30) | BCL11B |
| T/NK | chr14: 99269613-99270139 | TGGCTCCTATGCTGGGTTTTCAGGGGAGGGGAGA ACCACTTTATATATTTATTTATTTATTTAAATTTTTTA AAATATAACATAAATATTCGGCTCTCGGCCGCCCG GCAGCCAGTCCTCTGCGGTGACTGGGCGCGCAG CCCTCTCGAGCTCCGCGCGGGCAGCCCGGCCCC AGCCCGGCGAGGTGCGCGGCGGATTGCAAGCAT ATAACCTGCCCGCGGTCTCGATGGCACCCAGAGG ATGTTTTATTTCTATTGCAGTTAAAAAAAAAAAAAAA AAAAAAAAAAAAAAAAAAGGAACGGCGACCCAG GCACCGCGAGAGAAAGAACGGCGGGGAAATGTTC GCGCGCAGCGAAGAAGCCGCCCCGCGGGCTGCG GCGGGCGGGGAGCGCCGCAAAGCCACCTTCCCG GTGCAAGTGTGCGGGGACTCGGGGCGGGTTCCC CTGCAAACACCGTACCTGGCCCGCTCGCGCTCGC TTTTCCCCTCTGCTAAATAAACCCAACAGGGACGG TGGAAGCTGCTG (SEQ ID NO: 31) | BCL11B |
| B-cell | chr15: 70319616-70319805 | CAGCTAGTGGGTGGTGGATCCGTGCTCTTGACCA CCCCACTCTGTTGCCTTTCTGTTAGACAACACCTT GTCTACTTTCTCTTCCCCATTTCACAGATGAGGAG ACAGGACCGGAACTGTGAGGACAATCTGTCTATA GTTAGGCAGTGAGCTGACTGCAGACTCAGGCTCT CCTGGGACCCTCTTCAG (SEQ ID NO: 32) | intergenic |
| CD8 | chr16: 56708539-56708977 | GCAAAAAGGCAGGGGCTGCAGGGGACTTTATAAA GTTGTGCTGTCTGGGCTGAAGGCTTGCAGACAGG AAGCTTGGGTGCAGGTGGGCTGTGAGCTGAATGC TTGCAACAGGATGTTTGGGTGCTAGTGAGCTGTTT GCTGTTGACCCTATTTCTCAGAACATTCACTCCCC TCTACCCCTGTGTCTGTTCTTGCCAGCTAAGCTCA TTTCCAATTTTCTTTTAGCTCCTTAGGGCTCCACAT GCGTGACTTATTAGAGGAGCAAAAGAAGCCGAATA TGGAAGGGGAAAGCCTTGGCCTGATCCAGGGTGC TCTAGAACAAATTCCTCCCCACTGAACTGTCCTGCT GTGGGGCAAGCAGGTGAGCACTTGTTCTGTTGTC | intergenic |

TABLE IIIb-continued

Characteristics of candidate enhancer sequences for various cell types identified herein

| Cell Specificity | Coordinates (hg38) | Sequence | Genome Location |
|---|---|---|---|
| | | AGTCACCATTTGCCCCCGGGGTGGGGTGTAACCT GCCAGGCATCCTCAAGGGATGCA (SEQ ID NO: 33) | |
| CD4 | chr16: 84766016-84766317 | CCCCCAGGCTGGTATTTCAGTGACACTCTTAGTCT GTTGTTGTCCCAAATGCTGCGTACCTGAAAGAAAG AGCACCCCTTTTGAGGCATCAAGACTTGATTCAGT CTCAGTTCTGAGACTGAATCAACAACTTTCAACAG GTGAATAATAAGAACCTCAGAAACCTGCGCTGACG CCCTCAGAAGCTGGTTTCCCGTCCTCTGTGGAAGT GGATTTAGAAGCCAGTTGAGCAGCCATGTGACCTT GAACAAGTCACTTCTGTGTTCTGCACTGTGAGCTC TATTCCACTGGCCCCTTTCTA (SEQ ID NO: 34) | USP10 |
| CD8/NK | chr17: 35890611-35890953 | TGAACCCAAGACTCTACAACATCCTGGCCTCGATT TTTGGTCCAGCTCTGGTTGGTTCTTTCTGTGTTATT CTGTTCTGCTCCTCAATTCCTCTCCCCTCCCCTCC CCCTCCTCTCCCACCCCTTCCCCCACCCCCTCC CCCTCCCCTCTTCTGTCACCTTGCACTGTGCACTT TAATGCACATTGCACTATGTCAAGGTACTAACTTTG ACAACTGCTCTCATAATTCCAACCACATTCAGGCT GAGGGTTGCAGCTTGGCTCCCCCTCACTCTTCTCA CCTTCACCACACAGGACATTGGCTGTGCACAGCC ACTTGTTTATTGCAGCTGGAGACCACA (SEQ ID NO: 35) | intergenic |
| T | chr18: 13274085-13274184 | CTTGCTGGCTCTCCTCGGTGGCTTCCTCTTGAATG AACCTTTCTTCTGAAGGCTTGATTTCCTTCCGGGA GGCTTAGTGTTTCTGCTCAGCCTTCTTTC (SEQ ID NO: 36) | LDLRAD4 |
| CD4 | chr18: 13276705-13277363 | TCTGTCACTCCCTCGTTGCGGACTCCTATGTAGGT CGCCTGGTGTGGGGAGAAGCATTCTTTGTGGTATT CGGTTGGGTAGAAGCCAATCACAGCTTCCACCTA CACTCAAGGGGAGGGAGTTGTACAGGGTGTAAGC AATTTGGGGAGTCACCTTAGAATTCTGCCCACCAC AGTACCTTTCTGGTTATTTCATGGACTTCCGTTCCC AAGAAATCTGAGCGTTTGCGTCCTAGGAAGACTG GTGAGAGCAGCCCCAGTGGAGGAATAAAAACTAA GATCTGGAAAATCAGCAGTGGGTTGTTTTCATCTC TCAGCAGGCAGGAAACAGGAGGAGAAAGGAATGT CTGTAGGCTCCCAACACTGATGGGAAGGAGGTGT TTGGCTGGGGTAGAGCTCCGCAGGAATCTCCCAG GCTCCTCTAGCTAGGTGCAGCCGTGTTTTATCCGG CTGTCTTTACATGGGCTGATCACTCAGGAGTGGCA TATGCAGGAGCACGCTTTGGGGTACGAGCCTCC TGGAGAATGAACTGCAGCACACAAGCCAGACAGA TGGTGGCTTAGTCCCCCTTGGACAAGAGTGTGTC CTGCACACTGGAGGGCGGGGTGCTGAGAGGCGC TTGTGGTGTCTGAGGCCGAGCTTTGCTGAGTTCAC CTGA (SEQ ID NO: 37) | LDLRAD4 |
| CD4/NK | chr2: 147449478-147449829 | TGAAAGAAAGAGAATAAAGCACTGGGCTTTGCAAA CTAGGCTAAGGCCCCAAACCACAAGATTATCTTGA TGCATGTGATTGGGAAGGAGGACTAATTAGAAGA GAGGATGTCATTTTATTTTCTAACCAGCCCTCTCTG ATCTGAAGCCATGACACCCCCTCACTTGTTACCTA GCAACCCTTCTTTGTATATGTAAGGTTACTTCATTC CTGCATTGTTATTCAATTTATTTGCCATTTTAAGTG TCTTGATCCTCTCTAGGATCACCCTGGTGTGATTG GCTGGCATTAGTCTCTAAAATACCGGAGGGCAGT CTATTAAGTGGATCCAAATGTCATTGTACAGCTCA (SEQ ID NO: 38) | intergenic |
| CD8/NK | chr2: 181142700-181142853 | CTGAGATGTTCGTAGTATTGTCATCTACATTTCATA GAAGAAGAAACTGAAACAGGTTAGGTAACTTACTC GTGGTCACAGAGGTAATTGGTGGATTTGAGGATTC ACAGGATTCTAAAATCGAGTTGCTGCACTGCCTTC TTTAAAAAATTA (SEQ ID NO: 39) | intergenic |
| CD8/NK | chr2: 86793857-86794067 | TGTCAGCCAGTGGGGTGGCAGCCCCTTTGTACAG AGCACCATGGGGGTTGGGTGGGGAGGATAAGG CAACATGTCAAACCCATCAAGGAGGCTTTGTGACC CCAGTGATATTTTTTGCAGAACGTGGTGGATTTTC GATGTGACCACAATGACATCCGCCTTGCAGTGGC | CD8a |

TABLE IIIb-continued

Characteristics of candidate enhancer sequences for various cell types identified herein

| Cell Specificity | Coordinates (hg38) | Sequence | Genome Location |
|---|---|---|---|
| | | AGAACAGATGCAATTGCACAAGTTCTGGAGAAACT TTCT (SEQ ID NO: 40) | |
| CD8/NK | chr2: 86794937-86795091 | TGCTCTCTGCTTACCAAACTCCTCTCCCTTAAGAC CCAGCTCAAGCATCTCCTTCCTGTGGGGTTTAGCT CCTTCCCCCTCCCACTCCCAGACAGTACAGACCA CATCCTTCTCTTCTCTGTGTCACCCGGACCTTGGG TATCTGCAGACTGGA (SEQ ID NO: 41) | CD8a |
| T | chr20: 21548472-21548637 | TAACTTAAGCGTGTTGGTATCTCTGTTAGTGGTGA AGTCGGCTGCAAACCACAAAACACCTGACTGCTAC GGAAGATATTAACAGGGACTTTTTTCCTTCTGCATA ACAGGAAGTCTTGAGTAGGTAGTCGAGGTTGGGT AGAGGACACTTCTGTTTCAATTCTA (SEQ ID NO: 42) | intergenic |
| CD4 | chr20: 52975358-52975749 | GCATTGCTCAGAATTGCTCGACTTTGATTATAATTA TCCTACGATCGATAAGGATCCAGGTGTACGTAACA TAACACTGTATCACATTATTTAAATCAGGTCCTTTT CATTAAGCTGTGTCTGTTGGTGCTGGCTAGTTTAT TGGTGTGTGTGGGTGTGTGGGGGTGTGTGTGTGT GTGTGTTAGAAACTTGTAACTATAGTTTCAGTTTTC TGGCCTATTATATTCCTACTGTCTTTGTATGTTTGT TTTGTATGATTCTTATTATTTTCACCAGAAGCGGAA ACCCTTTTTAAGCTGAAAAAGGATGATTCATTTCGT ACACAGTGAGGGCCCTCTTACCTTATTTATTTGCT CACATATTAATAGAGGAGACAGTTTTTCATGCAGT G (SEQ ID NO: 43) | intergenic |
| B-cell/NK | chr20: 57682799-57683080 | TTCTGCATGAGCAGGCCCCGCTGAAAAGGAAGGC GGCTCGCCAGATTTGTTTCGAATTATGAAAATAGA TGTTGTCTCCCCACCACATCTGTTTTGCCTGACAA ATGAGCAGCAGCTCGCCTCCTAAATAAGGCAGCA CACCAAGACGGTCTTGAAACTCCGGCTTCTCCAAC TCTTCAGAAAAGGAGAAGAAGAAGAAAAAAGAGTC CAAGCCTCCCAGGTTTGAGCTCTAAAAGCCAGAC CTTTTTCAATGTCATCTCTCACGCCGCAGTCTCCG GGGG (SEQ ID NO: 44) | PMEPA1 |
| CD4 | chr22: 42183675-42183793 | TATTAACAAGTTTGTGGTAAGGTGTTATGACAATGA TAGAAAACTAATACACGGGGATTTCCCAAGACTCT CAAGTGATTGTTCATTTTCCTTTTAGGTTCTTTTTTT TTTTTTTGA (SEQ ID NO: 45) | TCF20 |
| B-cell | chr7: 1022952-1023453 | GCCGGCTCTGTCGTCGAGGCGCTCACAGGCAGG CACACGTGAGCTCCTGGAGGACAGGGAGAGCGG CCGCCCCGCCCCTGCGGAGCACAGGACGCTTCCT GCCACCCCTGCAGAGCATGGGACGCTTCCTGCCA TGGTGCCGTGGCAATGGGTGGCACCTGCCTGTGG CCCCTTCTCAGAAGGACGTTTTAAACGCGTGAGGT CTGATGCACAGCCACAGGGAGACACAGACGAGCA GATGTGGGCATCCGAGTATTTACAAGGTCTGGTG GCTCCTGCAGCCGCGACACGGGCTGAGCGCAAG TGATGTGTGAGGTGTCCCCAACAGATGGCACGGG GAGCGCCCACACCCGCCACCGCGGGGTCTGCGG AAGCTCGTGTCAGCTGGAGGTTAGGGAAGACGCA CAGGGGCTCATTCTCCACCCAGGTTCAAACTCCCT GAACTCACGAGACCCAGGCTGAAGACATGGACAG ACTCCCAGCCCCAGCGCCCCTCTGAC (SEQ ID NO: 46) | C7ORF50 |
| CD4/NK | chr7: 70788396-70788551 | CTGACTGATAAAAGAAAAACAAATTTTCCTTCAAGG CAGTATGATAACAATCTCTTAACCACTGGGAGGAA TGTTTATGACATTCATCTCTGAGCTGTGAACTGCC AAAATGAGGCACGCCTAGCAACATAACCTGGCCG ACCCTAGGCCGCGAG (SEQ ID NO: 47) | AUTS2 |

Repeated motifs/domains in the sequences are underlined

Bioinformatics analyses were performed to further characterize the enhancer candidates listed in Tables IIIa and IIIB. First, the sequences were analyzed using the Multiple Em for Motif Elicitation (MEME) tool (Timothy L. Bailey and Charles Elkan, Proceedings of the Second International Conference on Intelligent Systems for Molecular Biology, pp. 28-36, AAAI Press, Menlo Park, California, 1994) to identify repeated motifs in the sequences of the enhancer candidates. The results are depicted in Table IV.

TABLE IV

| SEQ. ID NO: | Motif ID (see sequences below) | # of repeats |
|---|---|---|
| SEQ ID NO: 7 | 1 | 8 |
| SEQ ID NO: 8 | 3 | 2 |
| | 4 | 1 |
| | 17 | 1 |
| | 20 | 2 |
| SEQ ID NO: 9 | 4 | 2 |
| | 12 | 1 |
| SEQ ID NO: 10 | 3 | 1 |
| | 4 | 1 |
| | 12 | 1 |
| SEQ ID NO: 11 | 2 | 1 |
| | 4 | 7 |
| | 5 | 1 |
| | 7 | 2 |
| SEQ ID NO: 12 | 8 | 1 |
| | 18 | 1 |
| | 20 | 2 |
| SEQ ID NO: 13 | 3 | 3 |
| | 4 | 1 |
| | 7 | 2 |
| | 12 | 1 |
| | 13 | 1 |
| | 20 | 1 |
| SEQ ID NO: 14 | 3 | 1 |
| | 4 | 2 |
| | 7 | 3 |
| | 14 | 1 |
| SEQ ID NO: 15 | 4 | 1 |
| | 5 | 1 |
| | 7 | 1 |
| | 8 | 1 |
| SEQ ID NO: 16 | 5 | 2 |
| | 11 | 1 |
| | 14 | 1 |
| SEQ ID NO: 17 | 3 | 3 |
| | 5 | 2 |
| | 7 | 1 |
| | 11 | 1 |
| | 18 | 1 |
| SEQ ID NO: 18 | 3 | 2 |
| | 4 | 1 |
| | 7 | 3 |
| | 9 | 1 |
| | 11 | 1 |
| | 12 | 2 |
| | 13 | 1 |
| SEQ ID NO: 19 | 3 | 3 |
| | 13 | 1 |
| | 14 | 1 |
| | 20 | 1 |
| SEQ ID NO: 20 | 3 | 1 |
| | 4 | 1 |
| | 5 | 2 |
| | 16 | 1 |
| | 19 | 1 |
| SEQ ID NO: 21 | 3 | 1 |
| | 5 | 1 |
| | 6 | 1 |
| | 7 | 2 |
| | 11 | 1 |
| | 13 | 1 |
| | 16 | 1 |
| SEQ ID NO: 22 | 4 | 1 |
| | 12 | 2 |
| SEQ ID NO: 23 | 4 | 1 |
| | 11 | 1 |
| | 12 | 1 |
| SEQ ID NO: 24 | 4 | 1 |
| | 5 | 1 |
| SEQ ID NO: 25 | 4 | 2 |
| | 7 | 2 |
| | 12 | 1 |
| | 20 | 1 |
| SEQ ID NO: 26 | 3 | 1 |
| | 4 | 2 |
| | 8 | 1 |
| | 14 | 1 |
| | 20 | 1 |
| SEQ ID NO: 27 | 4 | 2 |
| SEQ ID NO: 28 | 9 | 1 |
| | 11 | 1 |
| | 13 | 1 |
| SEQ ID NO: 29 | 3 | 1 |
| | 7 | 4 |
| | 11 | 1 |
| | 12 | 1 |
| | 20 | 1 |
| SEQ ID NO: 30 | 3 | 4 |
| | 4 | 4 |
| | 6 | 1 |
| | 7 | 3 |
| | 8 | 2 |
| | 9 | 1 |
| | 16 | 2 |
| | 20 | 1 |
| SEQ ID NO: 31 | 3 | 1 |
| | 4 | 4 |
| | 5 | 1 |
| | 6 | 2 |
| | 9 | 1 |
| | 15 | 1 |
| SEQ ID NO: 32 | 3 | 1 |
| | 9 | 1 |
| | 12 | 1 |
| SEQ ID NO: 33 | 3 | 1 |
| | 4 | 1 |
| | 5 | 4 |
| | 8 | 1 |
| | 12 | 1 |
| SEQ ID NO: 34 | 7 | 2 |
| SEQ ID NO: 35 | 3 | 3 |
| | 20 | 1 |
| SEQ ID NO: 36 | 14 | 1 |

TABLE IV-continued

| SEQ. ID NO: | Motif ID (see sequences below) | # of repeats |
|---|---|---|
| SEQ ID NO: 37 | 3 | 1 |
| | 5 | 1 |
| | 6 | 2 |
| | 7 | 1 |
| | 17 | 1 |
| SEQ ID NO: 38 | 4 | 1 |
| | 7 | 1 |
| | 20 | 1 |
| SEQ ID NO: 39 | 14 | 1 |
| SEQ ID NO: 40 | 3 | 1 |
| | 9 | 1 |
| SEQ ID NO: 41 | 3 | 1 |
| | 7 | 1 |
| SEQ ID NO: 42 | 3 | 1 |
| | 12 | 1 |
| | 20 | 1 |
| SEQ ID NO: 43 | 4 | 2 |
| | 5 | 1 |
| | 7 | 1 |
| SEQ ID NO: 44 | 3 | 1 |
| | 7 | 2 |
| | 11 | 1 |
| | 12 | 1 |
| | 17 | 1 |
| SEQ ID NO: 45 | 4 | 2 |
| SEQ ID NO: 46 | 3 | 1 |
| | 8 | 1 |
| | 9 | 2 |
| | 10 | 2 |
| | 13 | 2 |
| | 15 | 1 |
| | 19 | 1 |
| SEQ ID NO: 47 | 4 | 1 |
| | 7 | 1 |

Sequences of motif ID
1. CGGTGTGGAGGGCCGGGTGGTGACGCTGAGTGACAGGTGAGGATGTGGCA (SEQ ID NO: 64)
2. GTGGGACACCCATCATCTTACCACATCACATCGTCACTGCC (SEQ ID NO: 65)
3. YSCCTYCCCCWCCYCYTYCCH (SEQ ID NO: 66)
4. AAAADAAANAAARWA (SEQ ID NO: 67)
5. YTGGKGGSHRGGSGKSTGTG (SEQ ID NO: 68)
6. CTCVGVSCDGGNDGCCHGGCHMANVCCGGGCCWGBBBCGCGGVSG (SEQ ID NO: 69)
7. TCWSTKTTCTG (SEQ ID NO: 70)
8. GTGDMASGTGCCTG (SEQ ID NO: 71)
9. GCAGCCRCCYCRCKGKCTGAG (SEQ ID NO: 72)
10. CCCCTGCRGAGCAYRGGACGCTTCCTGCC (SEQ ID NO: 73)
11. TGKCCTCTMCCCACM (SEQ ID NO: 74)
12. GCCYTBHTGTYASRCAMAASM (SEQ ID NO: 75)
13. SWMTGACACMCTGTGKGTGTGMSYYWGMMSYCASYWG (SEQ ID NO: 76)
14. ACYTKCTGCWCWGCCTTMTTT (SEQ ID NO: 77)
15. CGGGGAGCGCC (SEQ ID NO: 78)
16. AGGHAGCAVAGKCACCCTC (SEQ ID NO: 79)
17. TBTGGCGAGBCDCCTTNGNHTTCWGYGBGCCHCACT (SEQ ID NO: 80)
18. TGTGCCCAGGG (SEQ ID NO: 81)
19. GAGGTGTCCCC (SEQ ID NO: 82)
20. AAACCACA

* motifs 1 and 2 are highly repeated in SEQ. ID No. 7 and SEQ ID No 11, respectively (in bold in the table)

Second, the sequences were analyzed using the oPOS-SUM tool (Kwon A T, Arenillas D J, Worsley Hunt R, Wasserman W W. G3. 2012 September;2 (9): 987-1002. Epub 2012 Sep. 1) that permits the detection of over-represented conserved transcription factor binding sites and binding site combinations in sets of sequences. The results are depicted in Tables V and FIG. 13.

TABLE V

Predicted conserved transcription factor binding site (bs)

| SEQ ID NO | Cell Specificity | Conserved binding site |
|---|---|---|
| 7 | Tspecific (Chr16-445) | none |
| 8 | T/NK | Zipper-type-Leucine Zipper-C9 binding site (bs): 2 times |
| | | Winged Helix-Turn-Helix-Forkhead-C12 bs: 1 time |
| | | Beta-Hairpin-Ribbon-E2F T-C13 bs: 1 time |
| | | Helix-Turn-Helix-RFX-C154 bs: 1 time |
| | | Helix-Turn-Helix-Homeo-C113 bs: 3 times |
| | | Winged Helix-Turn-Helix-Forkhead-C57 bs: 2 times |
| 9 | T | Zipper-type-Leucine Zipper-C9 bs: 3 times |
| | | Winged Helix-Turn-Helix-Forkhead-C12 bs: 1 time |
| | | Other Alpha-Helix-Sand-C158: 1 time |
| | | Helix-Turn-Helix-Homeo-C113 bs: 7 times |
| | | Winged Helix-Turn-Helix-Forkhead-C57 bs: 4 times |
| 10 | T/NK | Zipper-type-Leucine Zipper-C9 bs: 1 time |
| | | Zinc-coordinating-BetaBetaAlpha-zinc finger-C29: 1 time |
| | | Helix-Turn-Helix-RFX-C154 bs: 1 time |
| | | Helix-Turn-Helix-Homeo-C113 bs: 2 times |
| | | Winged Helix-Turn-Helix-Forkhead-C57 bs: 1 time |
| 11 | NK (NK6) | Winged Helix-Turn-Helix-Forkhead-C12 bs: 6 times |
| | | Beta-Hairpin-Ribbon-E2F T-C13 bs: 1 time |
| | | Helix-Turn-Helix-Homeo-C113 bs: 3 times |
| | | Winged Helix-Turn-Helix-Forkhead-C57 bs: 2 times |
| 12 | NK (NK20) | Beta-sheet-TATA-binding-C1 bs: 2 times |
| | | Zipper-type-Leucine Zipper-C9 bs: 4 times |
| | | Winged Helix-Turn-Helix-Forkhead-C12 bs: 2 times |
| | | Helix-Turn-Helix-Homeo-C167: 1 time |
| | | Helix-Turn-Helix-RFX-C154 bs: 1 time |
| | | Helix-Turn-Helix-Homeo-C113 bs: 8 times |
| | | Winged Helix-Turn-Helix-Forkhead-C57 bs: 2 times |

TABLE V-continued

Predicted conserved transcription factor binding site (bs)

| SEQ ID NO | Cell Specificity | Conserved binding site |
|---|---|---|
| 13 | T/NK | Beta-sheet-TATA-binding-C1 bs: 1 time<br>Zipper-type-Leucine Zipper-C9 bs: 2 times<br>Winged Helix-Turn-Helix-Forkhead-bs: 3 times<br>Winged Helix-Turn-Helix-IRF-C134 bs: 1 time<br>Helix-Turn-Helix-Homeo-C113 bs: 7 times<br>Winged Helix-Turn-Helix-Forkhead-C57 bs: 5 times |
| 14 | NK (NK8) | Beta-sheet-TATA-binding-C1 bs: 1 time<br>Zipper-type-Leucine Zipper-C9 bs: 1 time<br>Winged Helix-Turn-Helix-Forkhead-C12 bs: 2 times<br>Helix-Turn-Helix-Homeo-C113 bs: 6 times<br>Winged Helix-Turn-Helix-Forkhead-C57 bs: 3 times |
| 15 | B | Beta-sheet-TATA-binding-C1 bs: 1 time<br>Zipper-type-Leucine Zipper-C9 bs: 3 times<br>Helix-Turn-Helix-Homeo-C113 bs: 8 times |
| 16 | B | Winged Helix-Turn-Helix-Forkhead-C12 bs: 1 time<br>Other Alpha-Helix-Sand-C158: 1 time<br>Helix-Turn-Helix-RFX-C154 bs: 1 time<br>Helix-Turn-Helix-Homeo-C113 bs: 2 times<br>Winged Helix-Turn-Helix-Forkhead-C57 bs: 2 times |
| 17 | B | Zinc-coordinating-BetaBetaAlpha-zinc finger-C29: 1 time<br>Helix-Turn-Helix-Homeo-C113 bs: 2 times<br>Winged Helix-Turn-Helix-Forkhead-C57 bs: 4 times |
| 18 | T/NK | Beta-sheet-TATA-binding-C1 bs: 1 time<br>Winged Helix-Turn-Helix-Forkhead-C12 bs: 1 time<br>Helix-Turn-Helix-Homeo-C167: 1 time<br>Helix-Turn-Helix-Homeo-C113 bs: 8 times<br>Winged Helix-Turn-Helix-Forkhead-C57 bs: 3 times |
| 19 | T/NK | Winged Helix-Turn-Helix-IRF-C134 bs: 2 times<br>Helix-Turn-Helix-Homeo-C113 bs: 2 times<br>Winged Helix-Turn-Helix-Forkhead-C57 bs: 2 times |
| 20 | T/NK | Zipper-type-Leucine Zipper-C9 bs: 1 time<br>Beta-Hairpin-Ribbon-E2F T-C13 bs: 1 time<br>Zinc-coordinating-BetaBetaAlpha-zinc finger-C29: 1 time<br>Helix-Turn-Helix-Homeo-C113 bs: 4 times<br>Winged Helix-Turn-Helix-Forkhead-C57 bs: 2 times |
| 21 | T/NK | Helix-Turn-Helix-Homeo-C113 bs: 4 times<br>Winged Helix-Turn-Helix-Forkhead-C57 bs: 3 times |
| 22 | CD4/NK | Beta-sheet-TATA-binding-C1 bs: 1 time<br>Zipper-type-Leucine Zipper-C9 bs: 3 times<br>Helix-Turn-Helix-Homeo-C167: 1 time<br>Winged Helix-Turn-Helix-IRF-C134 bs: 1 time<br>Helix-Turn-Helix-Homeo-C113 bs: 6 times<br>Winged Helix-Turn-Helix-Forkhead-C57 bs: 2 times |
| 23 | B (b-enh-1) | Zipper-type-Leucine Zipper-C9 bs: 2 times<br>Winged Helix-Turn-Helix-Forkhead-C12 bs: 2 times<br>Zinc-coordinating-BetaBetaAlpha-zinc finger-C29: 1 time<br>Helix-Turn-Helix-Homeo-C167: 1 time<br>Helix-Turn-Helix-Homeo-C113 bs: 5 times<br>Winged Helix-Turn-Helix-Forkhead-C57 bs: 1 time |
| 24 | T/NK | Zinc-coordinating-BetaBetaAlpha-zinc finger-C29: 1 time<br>Winged Helix-Turn-Helix-Forkhead-C57 bs: 2 times |
| 25 | T/NK | Beta-sheet-TATA-binding-C1 bs: 1 time<br>Zipper-type-Leucine Zipper-C9 bs: 3 times<br>Winged Helix-Turn-Helix-Forkhead-C12 bs: 2 times<br>Winged Helix-Turn-Helix-IRF-C134 bs: 1 time<br>Helix-Turn-Helix-Homeo-C113 bs: 3 times<br>Winged Helix-Turn-Helix-Forkhead-C57 bs: 6 times |
| 26 | T/NK | Winged Helix-Turn-Helix-Forkhead-C12 bs: 1 time<br>Helix-Turn-Helix-RFX-C154 bs: 1 time<br>Helix-Turn-Helix-Homeo-C113 bs: 6 times<br>Winged Helix-Turn-Helix-Forkhead-C57 bs: 5 times |
| 27 | T | Zipper-type-Leucine Zipper-C9 bs: 1 time<br>Winged Helix-Turn-Helix-Forkhead-C57 bs: 3 times |
| 28 | T/NK | Zipper-type-Leucine Zipper-C9 bs: 1 time<br>Zinc-coordinating-BetaBetaAlpha-zinc finger-C29: 1 time<br>Helix-Turn-Helix-Homeo-C113 bs: 2 times |
| 29 | T/NK | Zipper-type-Leucine Zipper-C9 bs: 1 time<br>Winged Helix-Turn-Helix-Forkhead-C12 bs: 1 time<br>Other Alpha-Helix-Sand-C158: 1 time<br>Winged Helix-Turn-Helix-IRE-C134 bs: 1 time<br>Helix-Turn-Helix-Homeo-C113 bs: 7 times<br>Winged Helix-Turn-Helix-Forkhead-C57 bs: 4 times |
| 30 | T/NK | Beta-sheet-TATA-binding-C1 bs: 2 times<br>Winged Helix-Turn-Helix-Forkhead-C12 bs: 2 times<br>Winged Helix-Turn-Helix-IRF-C134 bs: 3 times |

TABLE V-continued

Predicted conserved transcription factor binding site (bs)

| SEQ ID NO | Cell Specificity | Conserved binding site |
|---|---|---|
| 31 | T/NK | Helix-Turn-Helix-Homeo-C113 bs: 11 times<br>Winged Helix-Turn-Helix-Forkhead-C57 bs: 4 times<br>Beta-sheet-TATA-binding-C1 bs: 2 times<br>Zipper-type-Leucine Zipper-C9 bs: 1 time<br>Winged Helix-Turn-Helix-Forkhead-C12 bs: 1 time<br>Zinc-coordinating-BetaBetaAlpha-zinc finger-C29: 1 time<br>Helix-Turn-Helix-Homeo-C113 bs: 1 time |
| 32 | B | Winged Helix-Turn-Helix-Forkhead-C57 bs: 6 times<br>Zipper-type-Leucine Zipper-C9 bs: 1 time<br>Beta-Hairpin-Ribbon-E2F T-C13 bs: 1 time<br>Winged Helix-Turn-Helix-IRF-C134 bs: 2 times<br>Helix-Turn-Helix-Homeo-C113 bs: 1 time |
| 33 | CD8 | Winged Helix-Turn-Helix-Forkhead-C57 bs: 1 time<br>Zipper-type-Leucine Zipper-C9 bs: 1 time<br>Zinc-coordinating-BetaBetaAlpha-zinc finger-C29: 1 time<br>Helix-Turn-Helix-Homeo-C113 bs: 3 times<br>Winged Helix-Turn-Helix-Forkhead-C57 bs: 2 times |
| 34 | CD4 | none |
| 35 | CC8/NK | Zipper-type-Leucine Zipper-C9 bs: 2 times<br>Helix-Turn-Helix-Homeo-C113 bs: 3 times<br>Winged Helix-Turn-Helix-Forkhead-C57 bs: 1 time |
| 36 | T | Helix-Turn-Helix-Homeo-C113 bs: 1 time |
| 37 | CD4 | Zinc-coordinating-BetaBetaAlpha-zinc finger-C29: 1 time<br>Other Alpha-Helix-Sand-C158: 1 time<br>Helix-Turn-Helix-Homeo-C113 bs: 2 times<br>Winged Helix-Turn-Helix-Forkhead-C57 bs: 4 times |
| 38 | CD4-NK | Zipper-type-Leucine Zipper-C9 bs: 1 time<br>Winged Helix-Turn-Helix-Forkhead-C12 bs: 2 times<br>Helix-Turn-Helix-Homeo-C167: 1 time<br>Helix-Turn-Helix-REX-C154 bs: 1 time<br>Helix-Turn-Helix-Homeo-C113 bs: 8 times |
| 39 | CD8/NK | Beta-sheet-TATA-binding-C1 bs: 1 time<br>Zipper-type-Leucine Zipper-C9 bs: 1 time<br>Helix-Turn-Helix-Homeo-C113 bs: 2 times |
| 40 | CC8/NK | Zipper-type-Leucine Zipper-C9 bs: 1 time<br>Helix-Turn-Helix-Homeo-C113 bs: 1 time |
| 41 | CD8/NK | Winged Helix-Turn-Helix-Forkhead-C57 bs: 1 time |
| 42 | T | Zipper-type-Leucine Zipper-C9 bs): 1 time<br>Winged Helix-Turn-Helix-Forkhead-C12 bs: 1 time<br>Winged Helix-Turn-Helix-IRF-C134 bs: 1 time<br>Helix-Turn-Helix-Homeo-C113 bs: 4 times |
| 43 | CD4 | Beta-sheet-TATA-binding-C1 bs: 2 times<br>Zipper-type-Leucine Zipper-C9 bs: 1 time<br>Winged Helix-Turn-Helix-Forkhead-C12 bs: 2 times<br>Other Alpha-Helix-Sand-C158: 1 time<br>Winged Helix-Turn-Helix-IRF-C134 bs: 1 time<br>Helix-Turn-Helix-Homeo-C113 bs: 6 times<br>Winged Helix-Turn-Helix-Forkhead-C57 bs: 4 times |
| 44 | BINK | Zipper-type-Leucine Zipper-C9 bs: 2 times<br>Winged Helix-Turn-Helix-Forkhead-C12 bs: 1 time<br>Winged Helix-Turn-Helix-IRF-C134 bs: 1 time<br>Helix-Turn-Helix-Homeo-C113 bs: 1 time<br>Winged Helix-Turn-Helix-Forkhead-C57 bs: 3 times |
| 45 | CD4 | Zipper-type-Leucine Zipper-C9 bs: 1 time<br>Winged Helix-Turn-Helix-IRF-C134 bs: 1 time<br>Helix-Turn-Helix-Homeo-C113 bs: 2 times<br>Winged Helix-Turn-Helix-Forkhead-C57 bs: 3 times |
| 46 | B | Beta-Hairpin-Ribbon-E2F T-C13 bs: 1 time<br>Zinc-coordinating-BetaBetaAlpha-zinc finger-C29: 1 time<br>Helix-Turn-Helix-Homeo-C113 bs: 1 time<br>Winged Helix-Turn-Helix-Forkhead-C57 bs: 2 times |
| 47 | CC4/NK | Winged Helix-Turn-Helix-Forkhead-C12 bs: 1 time<br>Zinc-coordinating-BetaBetaAlpha-zinc finger-C29: 1 time<br>Helix-Turn-Helix-RFX-C154 bs: 1 time<br>Helix-Turn-Helix-Homeo-C113 bs: 2 times |

Example 3: In Vitro Validation of a T Cell-Specific Promoter Construct (Chr16-445, SEQ ID NO:7)

Figure 3A:
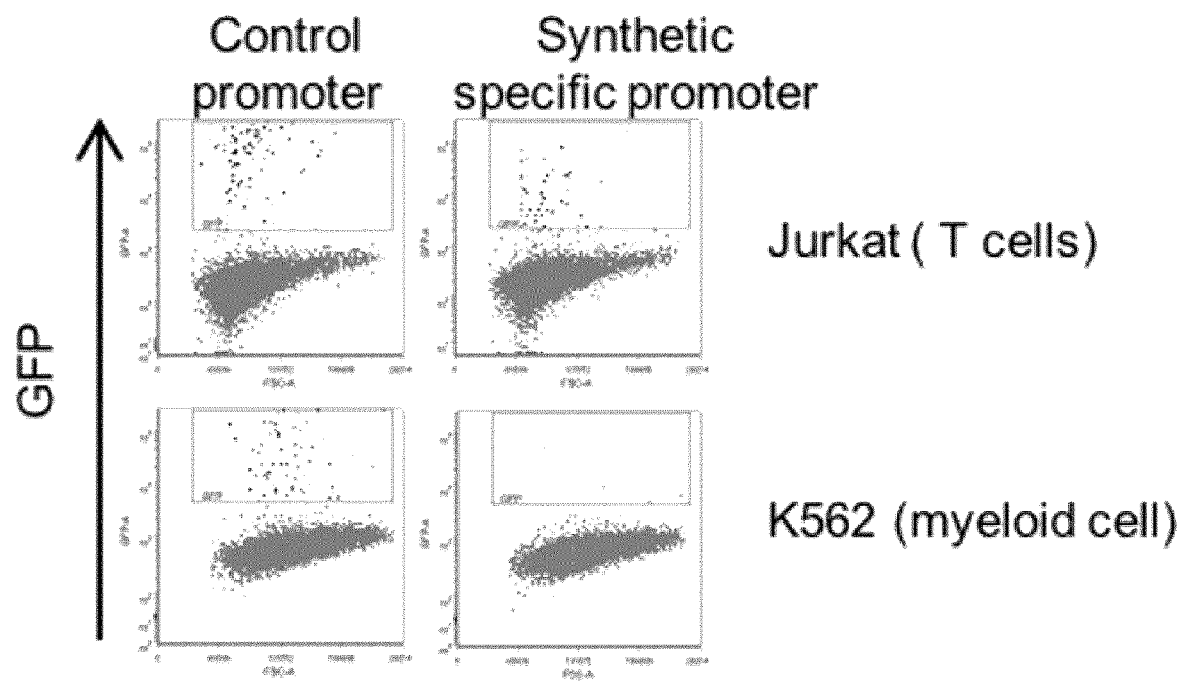
FIG. 3A: Jurkat (T-cell) and K562 (myeloid) cell lines were transfected with a vector coding for the GFP under a control promoter versus the synthetic T-cell specific promoter.
Figure 3B:
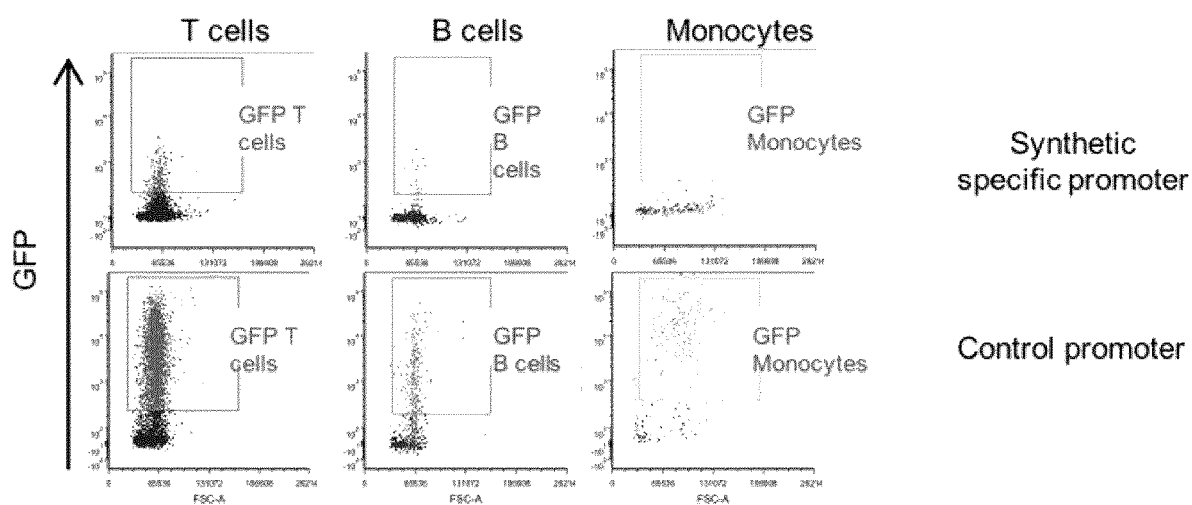
FIG. 3B: PBMC transfected with a vector coding for the GFP under a control spleen focus forming virus (SFFV) promoter versus the synthetic T-cell specific promoter.

A T cell-specific synthetic promoter was created by the juxtaposition of a selected enhancer sequence identified above and a minimal promoter such as CMV. The pENTR1a-Chr16-445-minCMV-GFP-SV40polyA vector was transfected in a T cell line (Jurkat) and myeloid cell line (K562), and GFP expression was only detected in the Jurkat T cell line by flow cytometry. In opposition, when transfected with a vector coding for a non-specific strong promoter (spleen focus-forming virus (SFFV) promoter) instead of the Chr16-445-minCMV promoter, both cell lines expressed GFP (FIG. 3A). Then, human PBMCs were transfected with the T cell-specific synthetic promoter and it was observed that GFP protein was only expressed in T cells, but not in monocytes or B cells (FIG. 3B), whereas all cell types expressed GFP when the PBMCs were transfected with a non-specific promoter.

Example 4: In Vitro Validation of a NK-Specific Promoter Construct (NK6, SEQ ID NO:11)

Figure 4:
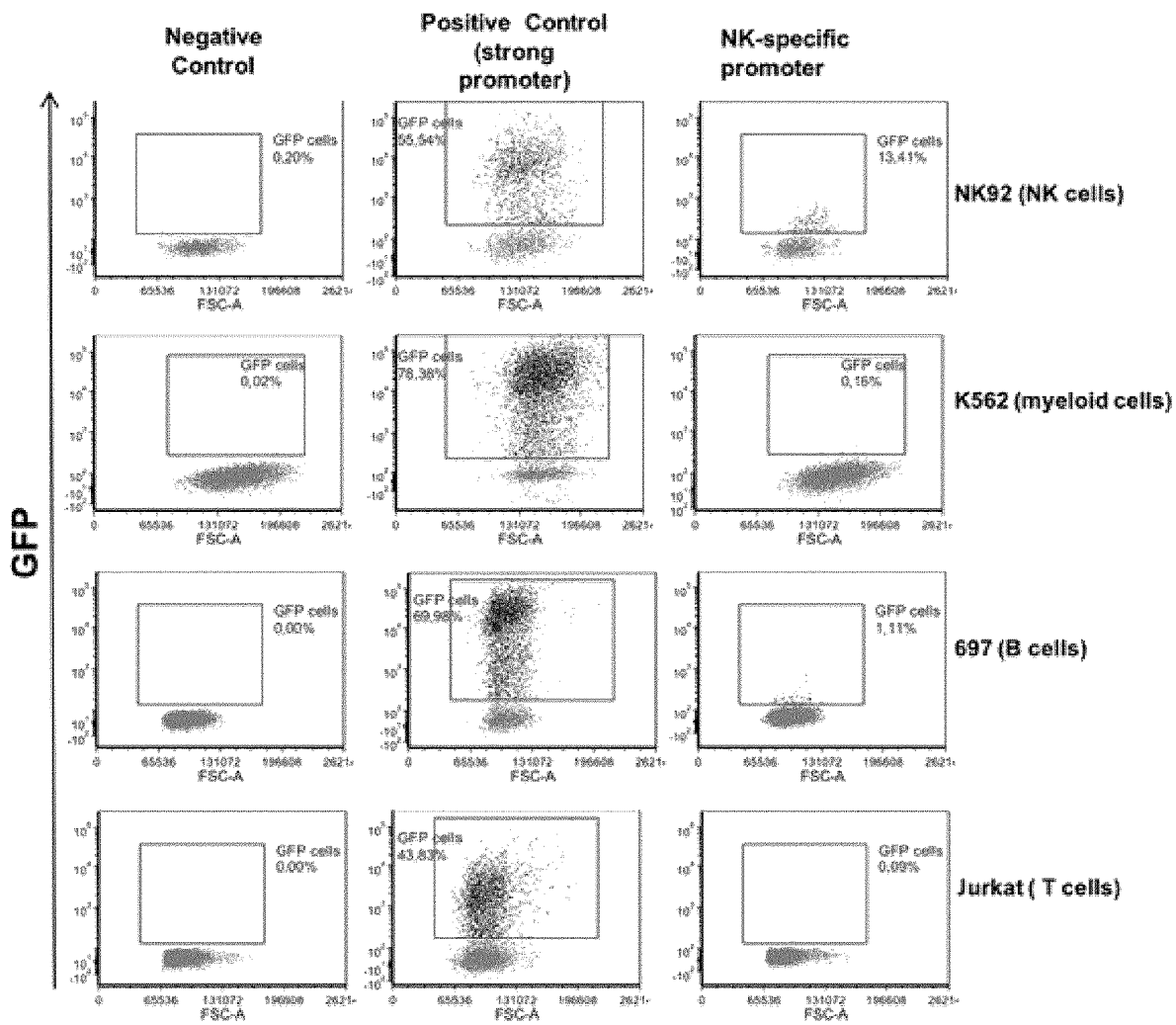
FIG. 4 shows the results of in vitro experiments for assessing the expression pattern of GFP under the control of the NK cell-specific synthetic promoter (NK6, SEQ ID NO:11). Various cell lines were transfected with a vector coding for the GFP under a control promoter versus the synthetic NK-cell specific promoter.

A NK cell line (NK92), myeloid cell line (K562), B cell line (697) and T cell line (Jurkat) were transfected with the pENTR1a-NK6-minCMV-GFP-SV40polyA vector. The NK6 synthetic promoter induced the expression of the GFP only in NK92 cells, whereas the SFFV strong promoter resulted in GFP expression in all cell lines (FIG. 4), confirming the specificity of the NK6 promoter.

Example 5: In Vitro Validation of Another NK-Specific Promoter Construct (NK8, SEQ ID NO:14)

Figure 5:
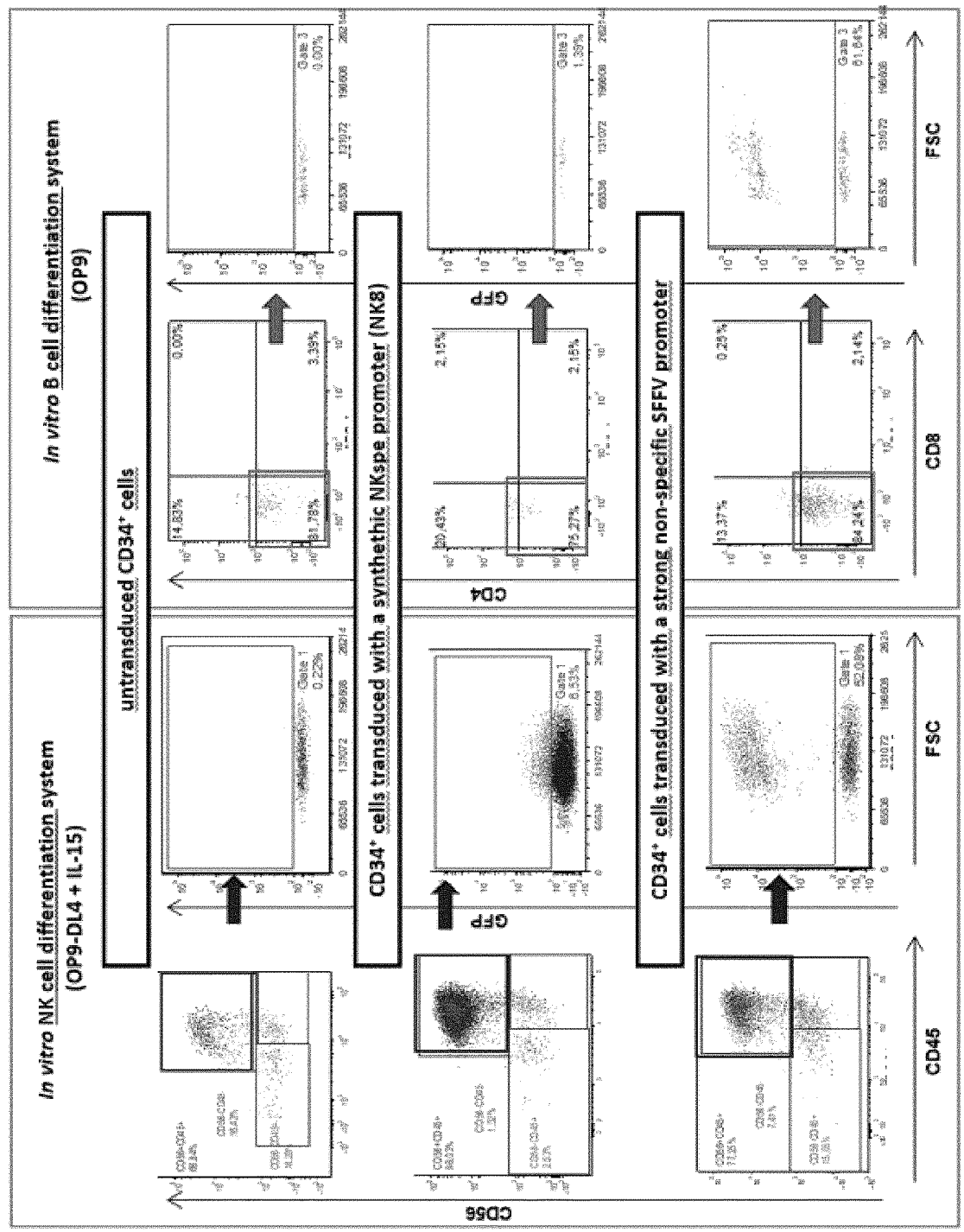
FIG. 5 shows the results of in vitro experiments aiming at determining the timing and functional expression of GFP under a synthetic NK cell-specific (NKspe-NK8, SEQ ID NO:14) promoter. In vitro differentiation system allowing for maturation of CD34$^+$ cells into NK cells (OP9-DL4 with NK-specific media, box on the left) or B cells (OP9, box on the right) shows that the GFP is expressed early in NK cells progeny but not in B cells, showing its NK cell specificity.

The NK8 sequence specificity was tested in an OP9 co-culture system with $CD34^+$ cells transduced or not with the NK8-minCMV-GFP-SV40polyA or the SFFV-GFP-SV40polyA. GFP expression was observed in the NK cells, but not in the B cells, harvested after co-culture in the well containing the NK8-transduced cells (FIG. 5). Cells transduced with the strong unspecific promoter (SFFV) led to both NK and B cells expressing GFP, while untransduced cells were not GFP positive. These results provide compelling evidence that the NK8-based synthetic promoter is specific to NK cells.

Example 6: In Vitro Validation of a B Cell-Specific Promoter Construct (SEQ ID NO:23)

Figure 6:
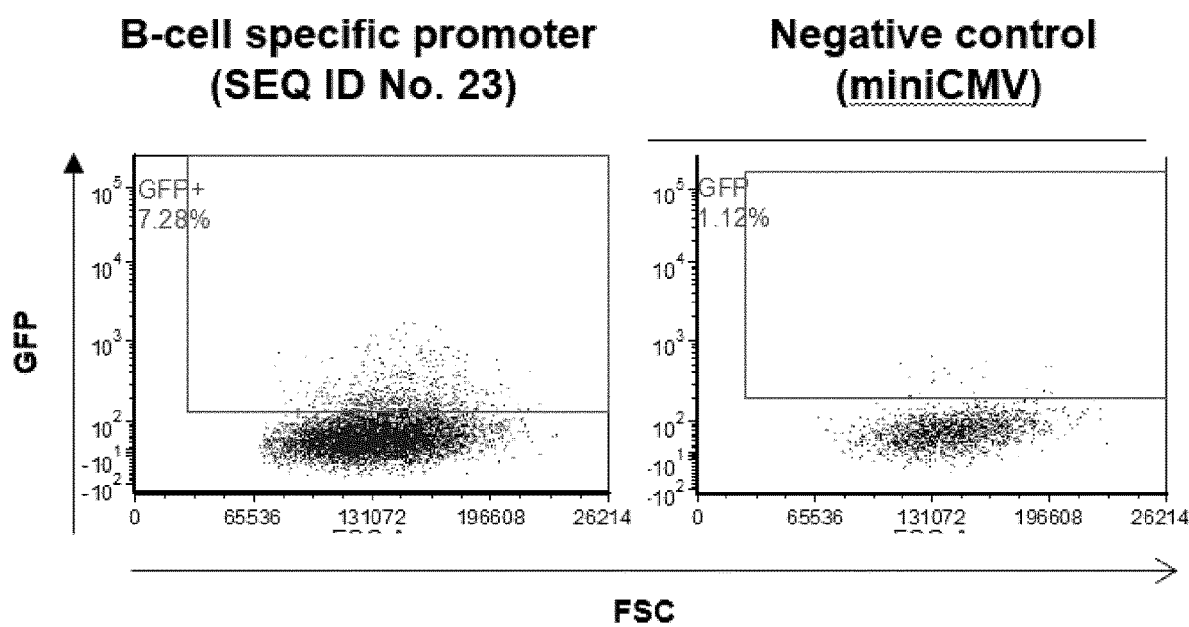
FIG. 6 shows the expression of GFP in Nalm6 cell line (B cell line) when transduced with a lentivirus coding for the GFP under the control of a B-cell specific promoter (B-enh-1, SEQ ID NO: 23, left panel), or the minimal CMV promoter sequence as a negative control (SEQ ID NO: 6, right panel).

A B cell line (Nalm6) was transduced with a BaEV-LV particles coding for the Benh-minCMV-GFP-SV40polyA. The B cell-specific synthetic promoter was shown to induce the expression of the GFP in the B cells (FIG. 6) suggesting that this promoter can induce the expression of a protein of interest in a B cell-specific manner.

Example 7: In Vivo Validation of the T-Specific Promoter Construct (Chr16-445)

Figure 7A:
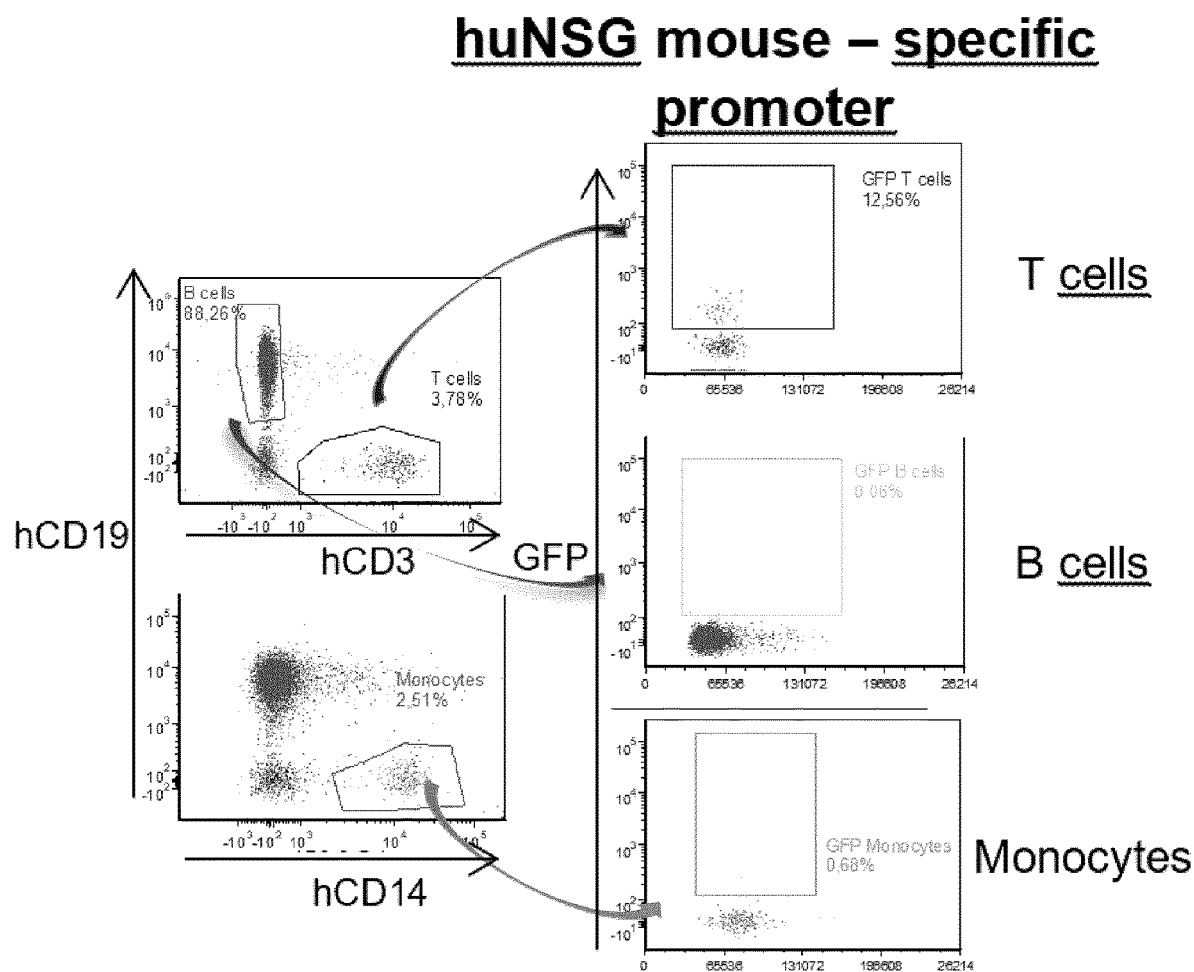
FIG. 7 shows the results of in vivo experiments for assessing the expression pattern of GFP under the control of the Chr16-445 T cell-specific synthetic promoter. In vivo validation of the synthetic promoter was assessed by injecting human CD34$^+$ cells transduced with GFP under the control of the synthetic promoter in a sublethally irradiated NSG mouse without (FIG. 7A) or with the engraftment of a human thymus (BLT model) (FIG. 7B). Blood analysis show that engineered-HSC can give rise to different immune populations and that only T cells express the GFP protein, validating the specificity of our promoter.
FIG. 7C: GFP expression in various cell types in BLT mice engrafted with CD34$^+$ cells transduced with GFP under the control of a strong non-specific promoter.
Figure 7B:
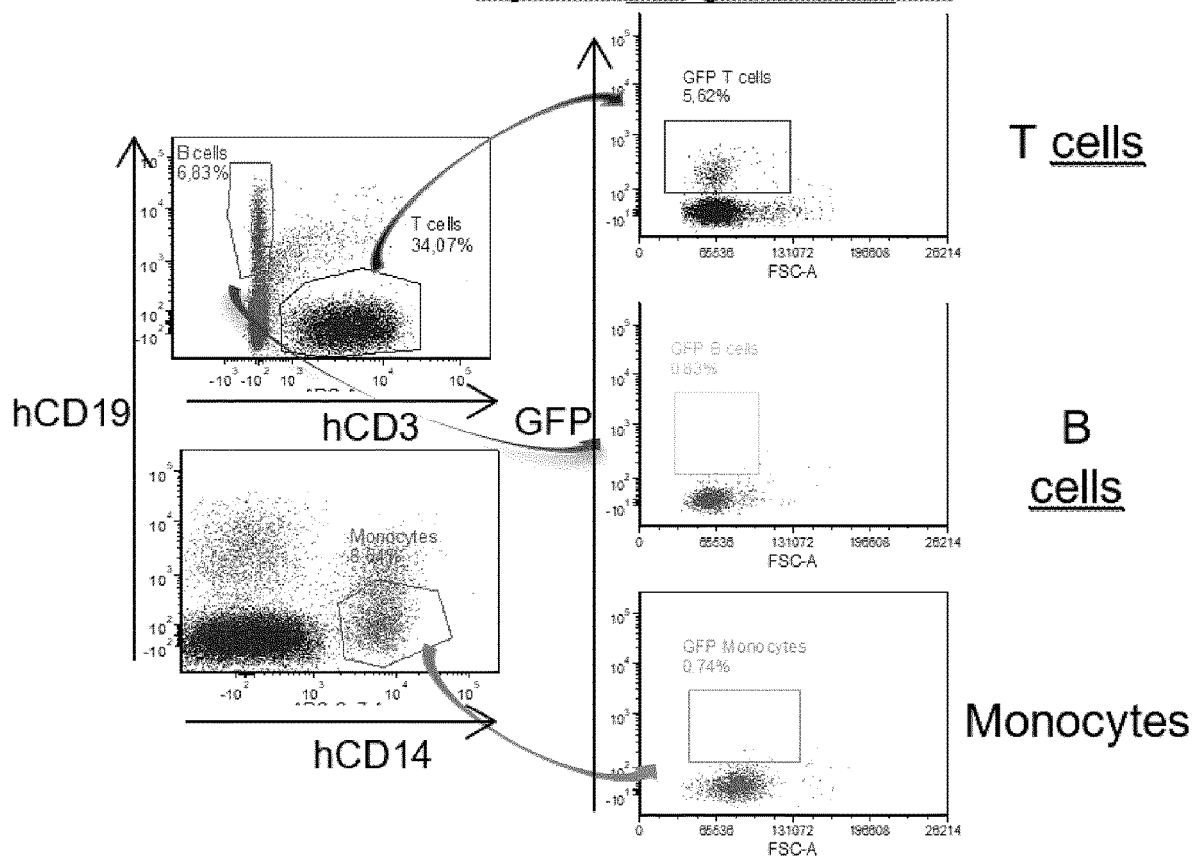
Figure 7C:
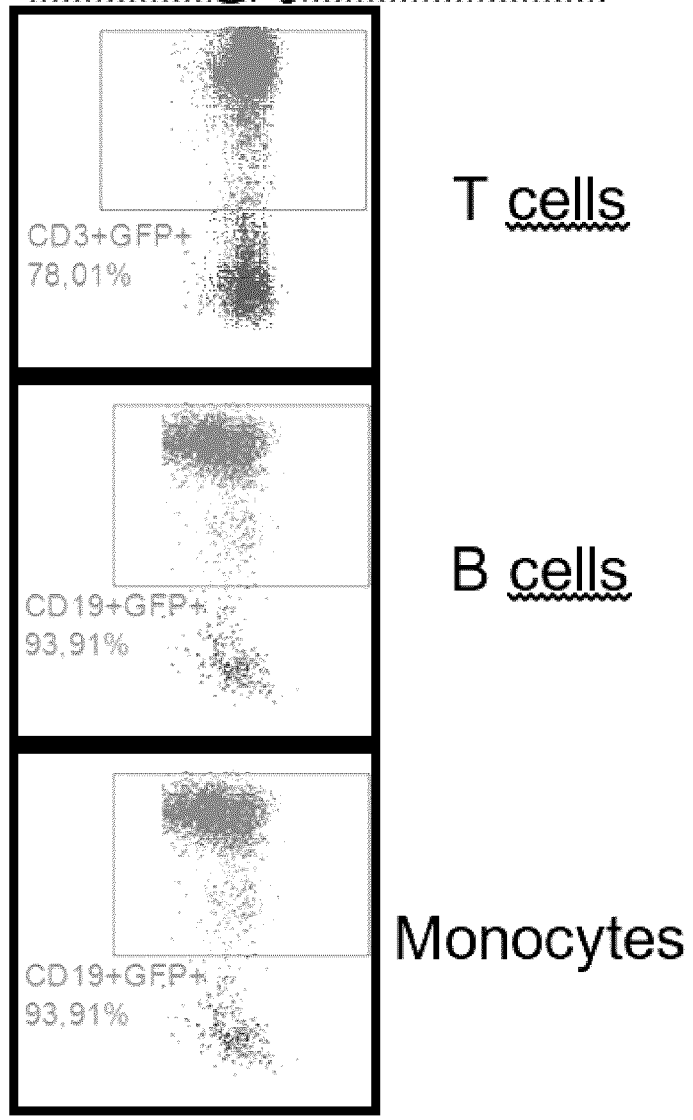

Human $CD34^+$ cells were transduced with the Chr16-445-minCMV T cell specific promoter or the non-specific SFFV promoter and engrafted in NSG mice with or without the co-engraftment of human thymus (huNSG and BLT models, see methods). In both models, the development of $GFP^+$ T cells was observed, while no other human cells expressed GFP (FIGS. 7A, B) when $CD34^+$ cells were transduced with our Chr16-445-minCMV T cell specific promoter. In contrast, all lineages expressed GFP when $CD34^+$ were transduced with the non-specific strong promoter SFFV (FIG. 7C). These results also show that engineered HSC are able to differentiate into various lineages both myeloid (monocytes) and lymphoid (T and B cells).

Example 8: In Vivo Validation of a NK-Specific Promoter Construct (NK8)

Figure 8A:
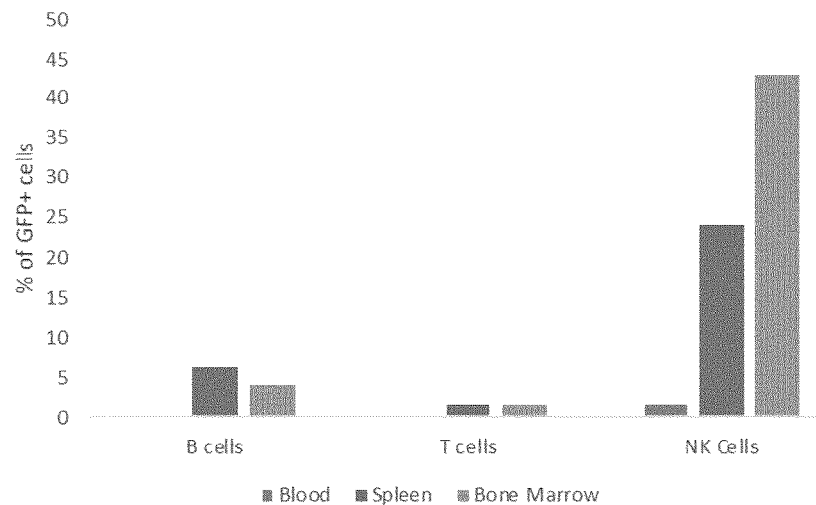
FIGS. 8A-B show the results of in vivo experiments aiming at testing the differentiation of CD34$^+$ cells modified with a GFP under the control of a NK-cell specific promoter (NK8, SEQ ID NO:14).
Figure 8B:
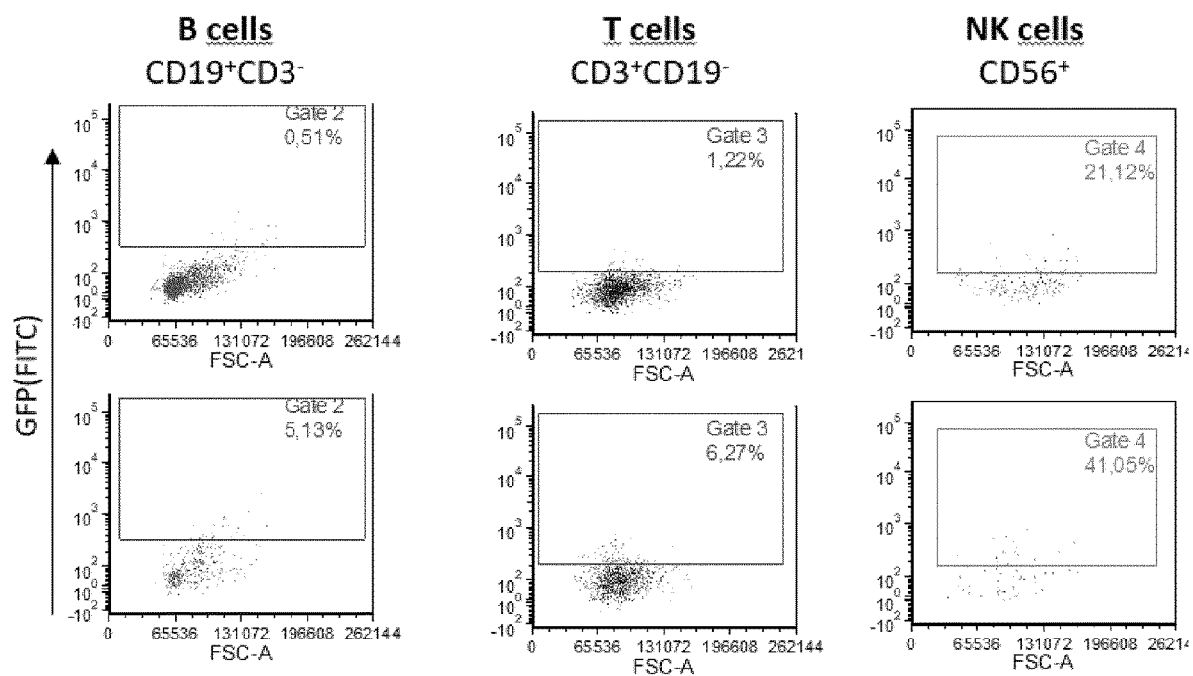

Human $CD34^+$ cells were transduced with the NK8-minCMV driving the GFP expression to test the specificity of NK cell specific promoter in vivo. Human NK cells expressing the GFP were found in blood, spleen and bone marrow of mice (FIGS. 8A, B). In contrast, very few human B and T cells harvested from the same mice expressed the GFP, witnessing the specificity of the NK8 synthetic specific promoter.

Example 9: In Vivo Validation of a B Cell Specific Promoter Construct (SEQ ID NO:23)

Figure 9:
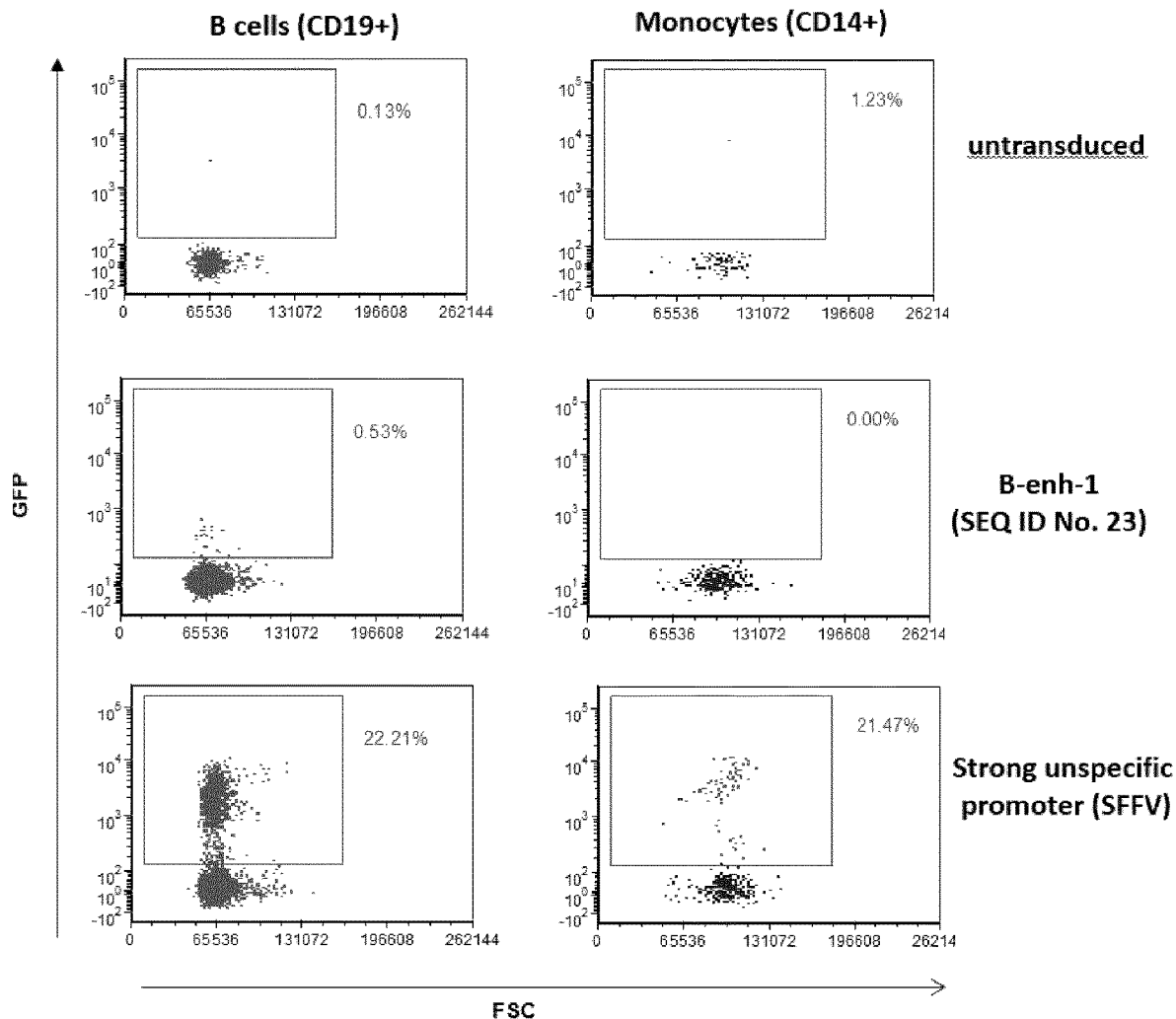
FIG. 9 shows the results of in vivo experiments aiming at testing the differentiation of CD34$^+$ cells modified with a GFP under the control of a B-cell specific promoter (B-enh-1, SEQ ID NO: 23). GFP expression was monitored in the blood of a humanized mice 4 weeks post-humanization. Cells were gated based on the expression of hCD45$^+$. Dot plots show that B cells (CD19$^+$), but not monocytes (CD14$^+$), express the GFP when the mice were humanized with CD34$^+$ transduced with the GFP under the control of the B-cell specific promoter (SEQ ID NO: 23, middle line). Mice humanized with CD34$^+$ expressing the GFP under the control of a strong and unspecific promoter (SFFV, bottom panels) show expression of GFP in all human subpopulations (hCD45$^+$), while no GFP expression is observed in untransduced CD34$^+$ (negative control). At this time post-humanization (week 4), no T-cell are found in the blood of mice.

Human $CD34^+$ cells were transduced with the Benh-minCMV driving the GFP expression to test the specificity of B cell specific promoter in vivo. Four weeks after humanization, human cells circulating in the blood were analyzed by flow cytometry. At this timepoint, only B cells ($CD19^+$) and monocytes ($CD14^+$) are developed in the humanized mice. While the strong unspecific promoter (SFFV) induced the GFP expression in all cell subtypes, GFP positive cells were only found in the B cell population (FIG. 9). These results suggest that the B cell synthetic specific promoter is induced specifically in the B cell population.

Example 10: Functional Validation of the T-Specific Promoter Construct (Chr16-445)

Figure 10A:
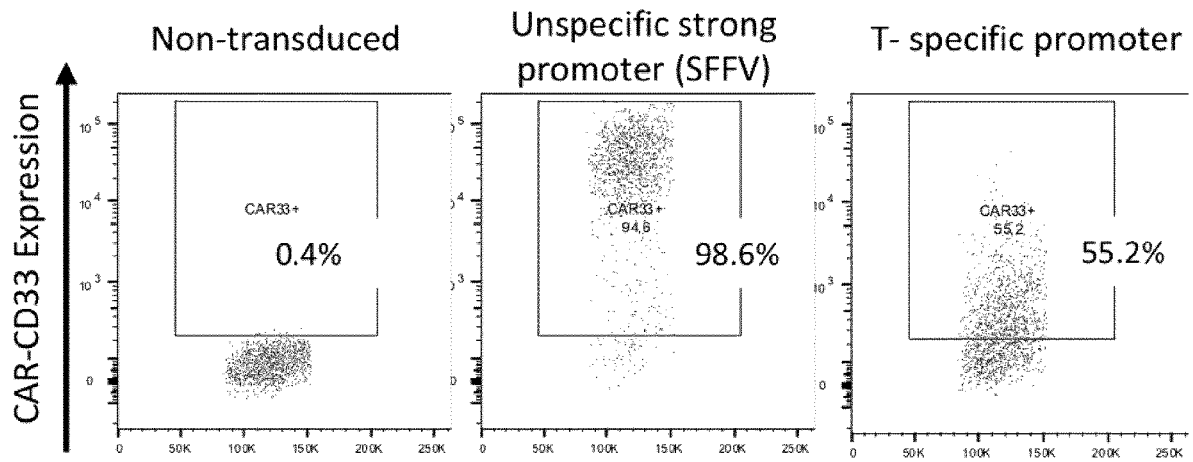
FIGS. 10A-D show the results of experiments for assessing the ability of the T-cell specific promoter for expressing a functional CAR.
Figure 10B:
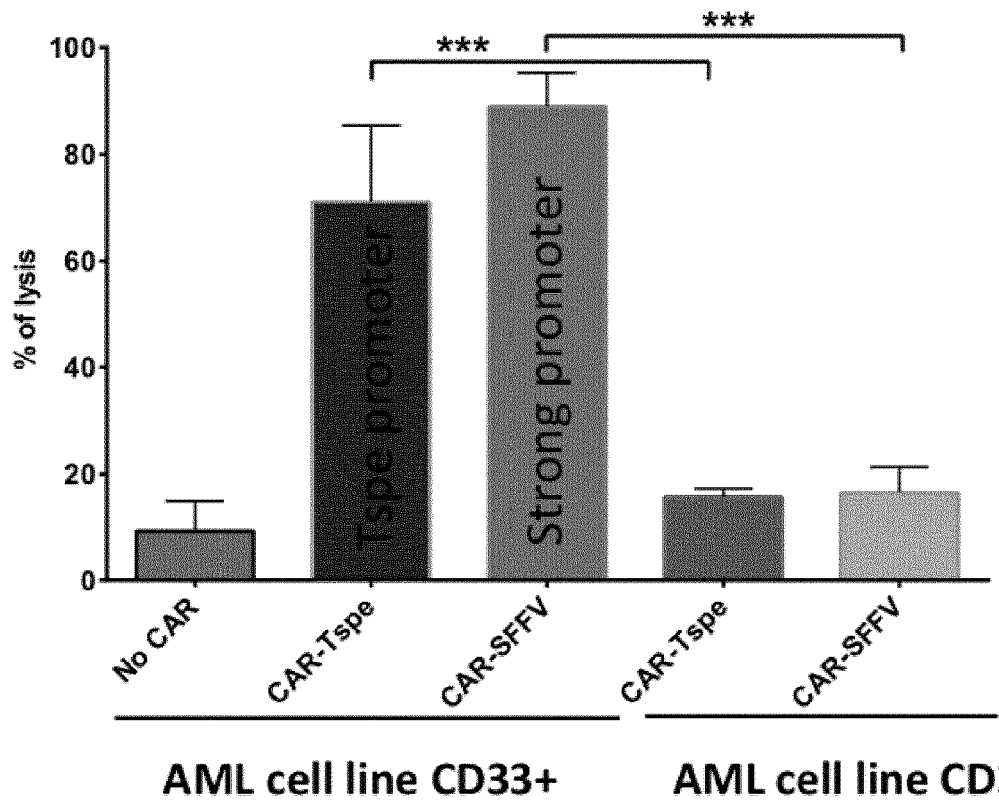
Figure 10C:
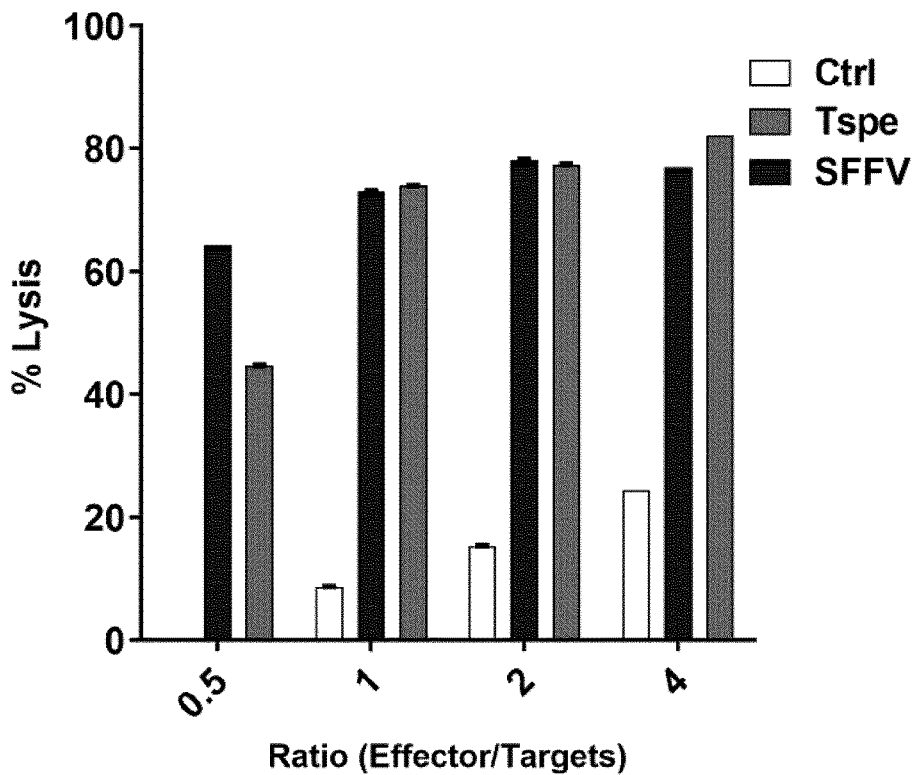
Figure 10D:
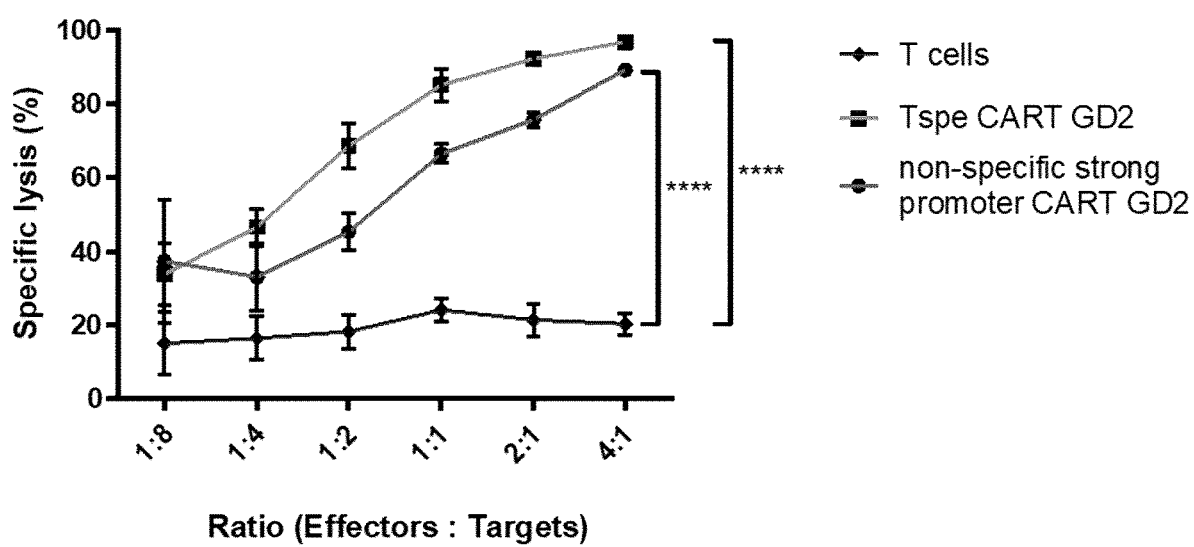

The therapeutic potential of the construct was explored through cytotoxic assays using CAR-CD33, CAR-CD22 or CAR-GD2. A sequence encoding a CAR-CD33, CAR-CD22 or CAR-GD2 was put under the control of a strong non-specific promoter (SFFV) or under the control of the synthetic T-cell specific promoter (Tenh Chr16-445). Its ability to drive the expression of a functional transgene was assessed by transducing primary T-cells with the CAR and performing cytotoxic assays against human AML cell lines expressing or not CD33, against human ALL cell line expressing CD22 (RS4; 11), or against a $GD2^+$ neuroblastoma (NB)-cell line (SK-N-DZ). Primary T-cells transduced with the CAR-CD33 construct under the control of the non-specific SFFV promoter or the T-cell specific promoter showed CAR-CD33 expression, as confirmed by flow cytometry (FIG. 10A). The results of cytotoxicity experiments show that the CAR-CD33 construct efficiently triggered lysis of $CD33^+$ AML cells, even when its expression was driven by the specific T cell promoter (FIG. 10B). Unspecific lysis measured in $CD33^-$ cells (right bars) was minimal and significantly lower than CAR-mediated lysis (* $p<0.001$). Similarly, CAR-CD22 expressed under the Tenh Chr16-445 promoter induced a CAR expression strong enough to induce a similar CAR-specific cytotoxicity against RS4; 11 ALL-cell line to that of SFFV (strong) promoter (FIG. 10C). Similarly, the results depicted in FIG. 10D show that in a context of solid tumor, a CAR-GD2 expressed under the Tenh Chr16-445 promoter construct also induced target lysis at levels significantly higher than untransduced primary T cells (** $p<0.0001$), and comparable to the levels of a CAR-GD2 driven by the strong unspecific promoter SFFV.

Example 11: Kinetic of Expression During T-Cell Differentiation of a CAR Under the T-Specific Promoter Construct (Chr16-445)

Figure 11A:
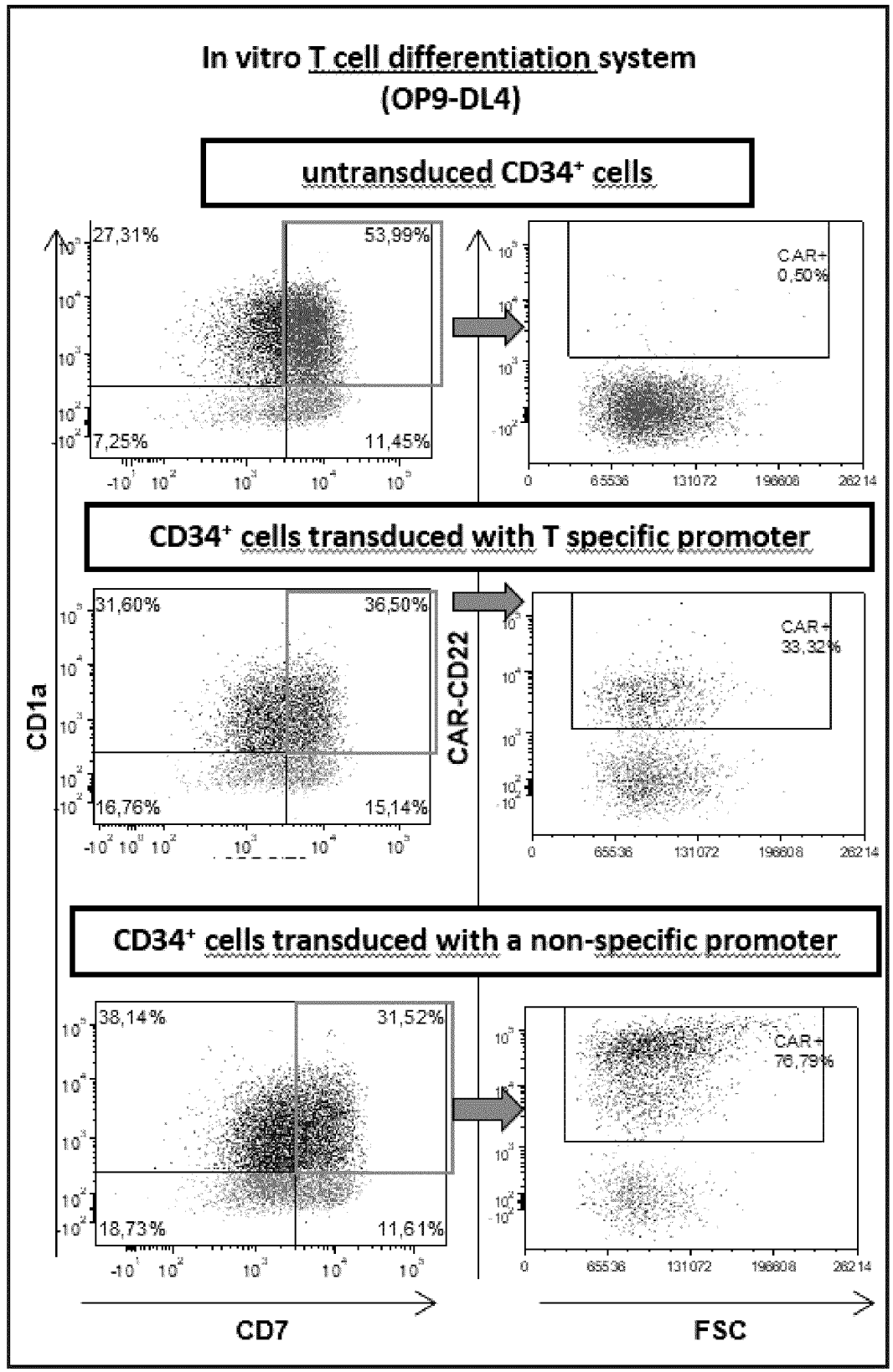
FIGS. 11A-C show the results of in vitro experiments aiming at determining the T cell differentiation stage at which the T-cell specific promoter is expressed. In vitro differentiation system allowing for maturation of CD34$^+$ cell into T cells (OP9-DL4-, FIG. 11A) or B cells (OP9, FIG. 11B) shows that the CAR is expressed early In T cells differentiation process (CD1aCD7$^+$ stage) but is not expressed in B cells, confirming its T cell specificity. FIG.
Figure 11B:
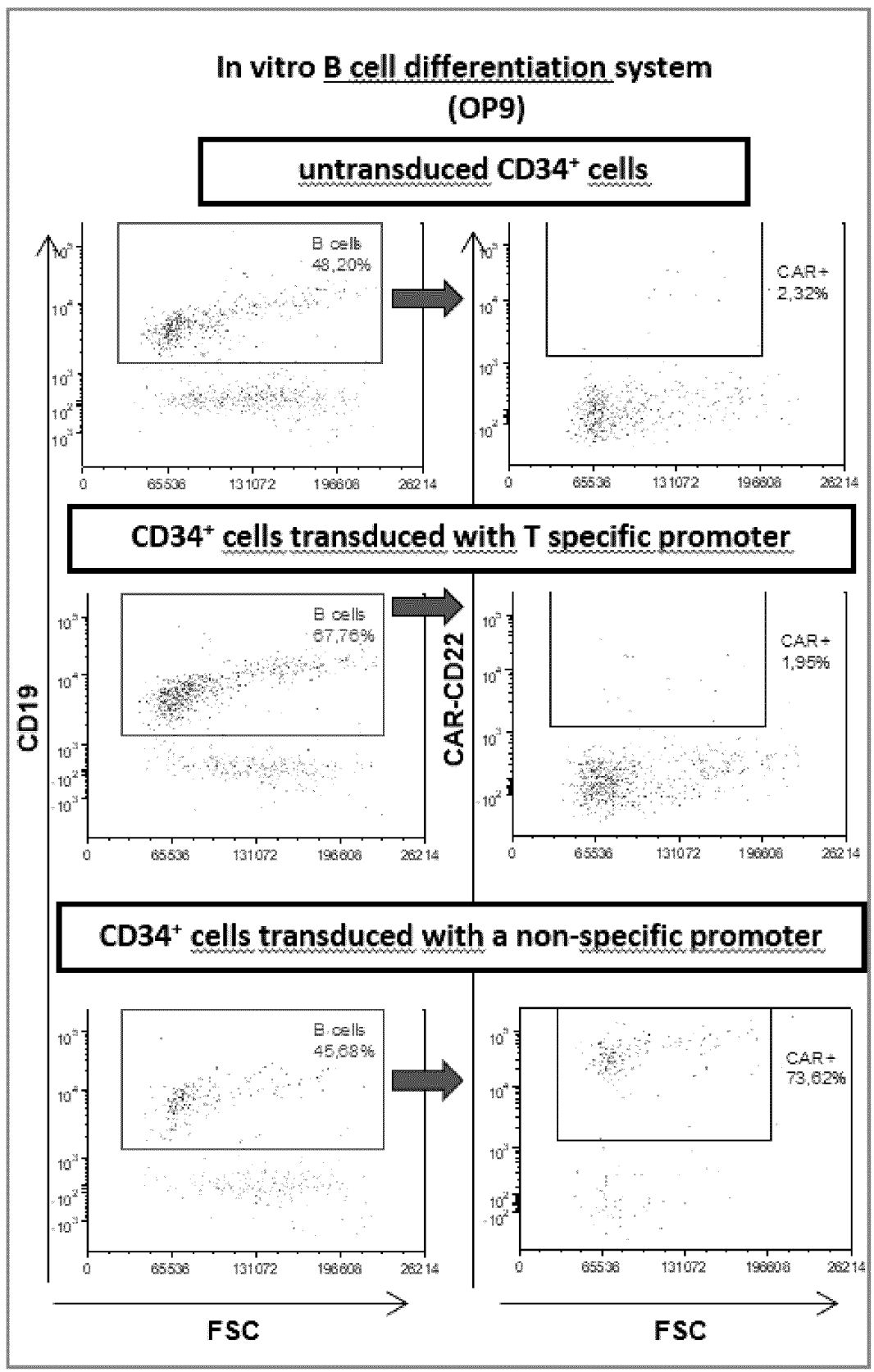
Figure 11C:
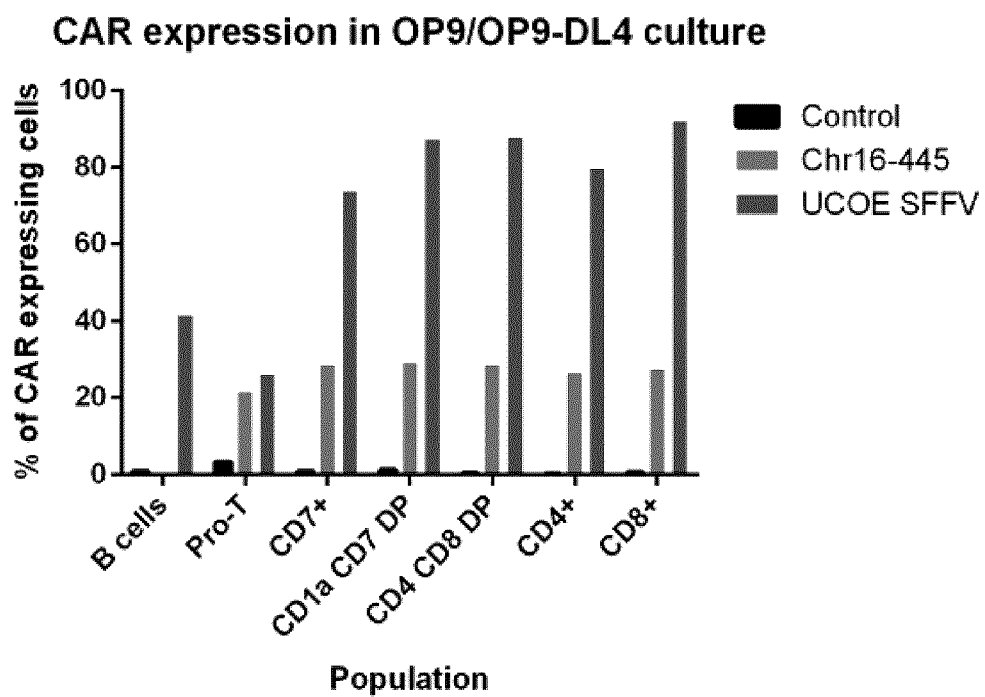

Using OP9-DL4 cells to mimic in vitro thymic differentiation and using a CAR-CD22 construct, it was observed that the specific promoter induced the expression of CAR-CD22 early in the T-cell differentiation process (as soon as $CD7^+CD1^+$ stage) (FIG. 11A). As a control, HSC engineered cells were co-cultured with OP9 cells, which results in B cell differentiation, and no CAR expression was detected (FIG. 11B). This data further evidences the specificity of the T-specific/Chr16-445 synthetic promoter. The results depicted in FIG. 11C shows that the Tenh Chr16-445 promoter is active in all stages of T cell differentiation: in pro-T, $CD7^+$, $CD7^+CD1a^+$, $CD4^+CD8^+$ double-positive, as well as $CD4^+$ and $CD8^+$ single-positive T cells. Similar results were obtained when Chr16-445 was inserted in the reverse orientation, confirming that this sequence shares this feature of transcription enhancers (i.e. orientation-independent).

Example 12: In Vivo T-Cell Differentiation of $CD34^+$ Cells Transduced with a CAR Under the T-Specific Promoter Construct The in vivo T-cell differentiation of $CD34^+$ cells transduced with a CAR was assessed in a mouse in which transduced $CD34^+$ cells were engrafted along with a fetal human thymus (BLT model). Blood sampling of the mice 30 weeks after humanization shows that T cells expressed the CAR-CD22 at their surface (FIG. 12). Consistent with the previous findings, B cells and monocytes did not express the GFP. Again, similar results were obtained when Chr16-445 was inserted in the reverse orientation. These results confirm the specificity of the T-specific/Chr16-445 promoter, but also suggest that thymic selection does not interfere with CAR-positive T cell development.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

REFERENCES

1. Hacein-Bey-Abina S, Hauer J, Lim A, et al. Efficacy of gene therapy for X-linked severe combined immunodeficiency. N Engl J Med 2010; 363:355-64.
2. Hacein-Bey-Abina S, Pai S Y, Gaspar H B, et al. A modified gamma-retrovirus vector for X-linked severe combined immunodeficiency. N Engl J Med 2014; 371: 1407-17.
3. Lizio M, Harshbarger J, Shimoji H, et al. Gateways to the FANTOM5 promoter level mammalian expression atlas. Genome Biol 2015; 16:22.
4. Andersson R, Gebhard C, Miguel-Escalada I, et al. An atlas of active enhancers across human cell types and tissues. Nature 2014; 507:455-461.
5. Boshart M, Weber F, Jahn G, et al. A very strong enhancer is located upstream of an immediate early gene of human cytomegalovirus. Cell 1985; 41:521-30.
6. Ede C, Chen X, Lin M Y, et al. Quantitative Analyses of Core Promoters Enable Precise Engineering of Regulated Gene Expression in Mammalian Cells. ACS Synth Biol 2016; 5:395-404.
7. Matsuda K, Mikami T, Oki S, et al. ChIP-seq analysis of genomic binding regions of five major transcription factors highlights a central role for ZIC2 in the mouse epiblast stem cell gene regulatory network. Development 2017; 144:1948-1958.
8. Levy C, Amirache F, Costa C, et al. Lentiviral vectors displaying modified measles virus gp overcome pre-existing immunity in in vivo-like transduction of human T and B cells. Mol Ther 2012; 20:1699-712.
9. Humbert J M, Frecha C, Amirache Bouafia F, et al. Measles virus glycoprotein-pseudotyped lentiviral vectors are highly superior to vesicular stomatitis virus G pseudotypes for genetic modification of monocyte-derived dendritic cells. J Virol 2012; 86:5192-203.
10. Girard-Gagnepain A, Amirache F, Costa C, et al. Baboon envelope pseudotyped LVs outperform VSV-G-LVs for gene transfer into early-cytokine-stimulated and resting HSCs. Blood 2014; 124:1221-31.
11. Lowe E, Truscott L C, De Oliveira S N. In Vitro Generation of Human NK Cells Expressing Chimeric Antigen Receptor Through Differentiation of Gene-Modified Hematopoietic Stem Cells. Methods Mol Biol 2016; 1441:241-51.
12. Huang J, Nguyen-McCarty M, Hexner E O, et al. Maintenance of hematopoietic stem cells through regulation of Wnt and mTOR pathways. Nat Med 2012; 18:1778-85.
13. Markert M L, Devlin B H, McCarthy E A. Thymus transplantation. Clin Immunol 2010; 135:236-46.
14. Kalscheuer H, Danzl N, Onoe T, et al. A model for personalized in vivo analysis of human immune responsiveness. Sci Transl Med 2012; 4:125ra30.
15. Laing A A, Harrison C J, Gibson B E S, et al. Unlocking the potential of anti-CD33 therapy in adult and childhood acute myeloid leukemia. Exp Hematol 2017; 54:40-50.
16. La Motte-Mohs R N, Herer E, Zuniga-Pflucker J C. Induction of T-cell development from human cord blood hematopoietic stem cells by Delta-like 1 in vitro. Blood 2005; 105:1431-9.
17. Halkias J, Melichar H J, Taylor K T, et al. Tracking migration during human T cell development. Cell Mol Life Sci 2014; 71:3101-17.
18. Kurd N, Robey E A. T-cell selection in the thymus: a spatial and temporal perspective. Immunol Rev 2016; 271:114-26.
19. Poulin J F, Sylvestre M, Champagne P, et al. Evidence for adequate thymic function but impaired naive T-cell survival following allogeneic hematopoietic stem cell transplantation in the absence of chronic graft-versus-host disease. Blood 2003; 102:4600-7.
20. Dion M L, Poulin J F, Bordi R, et al. HIV infection rapidly induces and maintains a substantial suppression of thymocyte proliferation. Immunity 2004; 21:757-68.
21. Sportes C, Hakim F T, Memon S A, et al. Administration of rhIL-7 in humans increases in vivo TCR repertoire diversity by preferential expansion of naive T cell subsets. J Exp Med 2008; 205:1701-14.
22. Kershaw M H, Westwood J A, Darcy P K. Gene-engineered T cells for cancer therapy. Nat Rev Cancer 2013; 13:525-41.
23. Porter D L, Hwang W T, Frey N V, et al. Chimeric antigen receptor T cells persist and induce sustained remissions in relapsed refractory chronic lymphocytic leukemia. Sci Transl Med 2015; 7:303ra139.
24. Savoldo B, Ramos C A, Liu E, et al. CD28 costimulation improves expansion and persistence of chimeric antigen receptor-modified T cells in lymphoma patients. J Clin Invest 2011; 121:1822-6.
25. Maude S L, Teachey D T, Porter D L, et al. CD19-targeted chimeric antigen receptor T-cell therapy for acute lymphoblastic leukemia. Blood 2015; 125:4017-23.
26. Maude S L, Frey N, Shaw P A, et al. Chimeric antigen receptor T cells for sustained remissions in leukemia. N Engl J Med 2014; 371:1507-17.

27. Grupp S A, Kalos M, Barrett D, et al. Chimeric antigen receptor-modified T cells for acute lymphoid leukemia. N Engl J Med 2013; 368:1509-18.
28. Haso W, Lee D W, Shah N N, et al. Anti-CD22-chimeric antigen receptors targeting B-cell precursor acute lymphoblastic leukemia. Blood 2013; 121:1165-74.
29. Lee D W, Kochenderfer J N, Stetler-Stevenson M, et al. T cells expressing CD19 chimeric antigen receptors for acute lymphoblastic leukaemia in children and young adults: a phase 1 dose-escalation trial. Lancet 2015; 385:517-28.
30. Fitzgerald J C, Weiss S L, Maude S L, et al. Cytokine Release Syndrome After Chimeric Antigen Receptor T Cell Therapy for Acute Lymphoblastic Leukemia. Crit Care Med 2017; 45:e124-e131.
31. Teachey D T, Lacey S F, Shaw P A, et al. Identification of Predictive Biomarkers for Cytokine Release Syndrome after Chimeric Antigen Receptor T-cell Therapy for Acute Lymphoblastic Leukemia. Cancer Discov 2016; 6:664-79.
32. Jena B, Maiti S, Huls H, et al. Chimeric antigen receptor (CAR)-specific monoclonal antibody to detect CD19-specific T cells in clinical trials. PLoS One 2013; 8:e57838.

---

What is claimed is:

1. A synthetic expression cassette for expressing a nucleic acid of interest in a T cell and natural killer (NK) cell comprising:
   (i) a minimal promoter; and
   (ii) a transcriptional enhancer operatively coupled to the minimal promoter for expression of the nucleic acid of interest in the cell, wherein the transcriptional enhancer comprises a sequence having at least 95% sequence identity with the nucleotide sequence set forth in SEQ ID NO: 24.

2. The synthetic expression cassette of claim 1, wherein the transcriptional enhancer comprises a sequence having at least 98% sequence identity with the nucleotide sequence set forth in SEQ ID NO: 24.

3. The synthetic expression cassette of claim 1, wherein the transcriptional enhancer comprises a sequence having at least 99% sequence identity with the nucleotide sequence set forth in SEQ ID NO:24.

4. The synthetic expression cassette of claim 1, wherein the transcriptional enhancer comprises the nucleotide sequence set forth in SEQ ID NO:24.

5. The synthetic expression cassette of claim 1, wherein the minimal promoter is a human cytomegalovirus CMV minimal promoter (miniCMV).

6. The synthetic expression cassette of claim 5, wherein the minimal promoter comprises the sequence of SEQ ID NO: 6.

7. The synthetic expression cassette of claim 1, wherein the transcriptional enhancer is upstream of the minimal promoter in the synthetic expression cassette.

8. The synthetic expression cassette of claim 1, further comprising the nucleic acid of interest operatively coupled to the minimal promoter and transcriptional enhancer.

9. The synthetic expression cassette of claim 8, wherein the nucleic acid of interest encodes a chimeric antigen receptor (CAR).

10. A vector comprising the synthetic expression cassette of claim 1.

11. An isolated A host cell comprising the synthetic expression cassette of claim 1.

12. The host cell of claim 11, wherein said cell is a hematopoietic stem cell, a T cell, or a natural killer (NK) cell.

13. A method for inducing the expression of a nucleic acid of interest in a cell, the method comprising introducing the synthetic expression cassette of claim 8 into said cell.

14. The method of claim 13, wherein the nucleic acid of interest encodes a chimeric antigen receptor (CAR).

15. The method of claim 13, wherein said cell is a hematopoietic stem cell, a T cell, or a natural killer (NK) cell.

* * * * *

SEQUENCE LISTING

<160> NUMBER OF SEQ ID NOS: 82

<210> SEQ ID NO 1
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 1
atcatcgcgg ccgcgggtct gacgtgctct gt                                       32

<210> SEQ ID NO 2
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 2
attcggtacc gtgggacacc agtcatctta                                          30

<210> SEQ ID NO 3
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 3
atatgcggcc gcgaccaggt ttggccaata ga                                       32

<210> SEQ ID NO 4
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 4
atcaggatcc gacacttgtt ctgggaccta                                          30

<210> SEQ ID NO 5
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 5
cagggaattc gcttacttgt tagcatccct ctcatacgc                                39

```
<210> SEQ ID NO 6
<211> LENGTH: 59
<212> TYPE: DNA
<213> ORGANISM: Cytomegalovirus

<400> SEQUENCE: 6
gtaggcgtgt acggtgggag gtctatataa gcagagctcg tttagtgaac cgtcagatc    59

<210> SEQ ID NO 7
<211> LENGTH: 445
<212> TYPE: DNA
<213> ORGANISM: Homo sapiens

<400> SEQUENCE: 7
ctggtggtgt ggagggccgg gtggtgacac tcagtgacag gtgaggatgt ggcacggtgt    60
ggagggccgg gtggtgacgc tgagtgacag gtgaggatgt ggcacggtgt ggagggccgg   120
gtggtgacgc tgagtgacag gtgaggatgt ggcacggtgt ggagggccgg gtggtgacgc   180
tgagtgacag gtgaggatgt ggcacggtgt ggagggccgg gtggtgacgc tgagtgacag   240
gtgaggatgt ggcacggtgt ggagggccgg gtggtgacgc tgagtgacac gtgaggatgt   300
ggcacggtgt ggagggccgg gtggtgacgc tgagtgacag gtgaggatgt ggcacggtgt   360
ggagggccgg gtggtgacgc tgagtgacag gtgaggatgt ggcataggga aacacatcct   420
cgccgagcgc acagtgggag ctccg                                         445

<210> SEQ ID NO 8
<211> LENGTH: 438
<212> TYPE: DNA
<213> ORGANISM: Homo sapiens

<400> SEQUENCE: 8
ctgaggactt ctagctcttc ctggatcctt atatgcccat ttgctattgt aaatagctat    60
atgacgttgt gatactattc caaaccctag tcatagcaac cacataccta atagccaagg   120
gataaccata ctatcttccc tttctgaaga acctttcagc aaaagatttc agggaatttt   180
accaagaaaa ccatcccatc ccctcctcct tccatttgac aggtggagaa gtgaggcaca   240
gtgaagccag aggagcctgg tcagacggtg agtcagaagt agagcagggc tgcacctggt   300
gacacctatt tcctcccttg tggtttggcc cctgcctcat aggcttcctg aaaggtgta   360 gcttcttcat ggcttacttg ttgagtaaac actgctatga gctttcaaat atttccctag   420
gttgcaggag gttgtgtc                                                 438

<210> SEQ ID NO 9
<211> LENGTH: 432
<212> TYPE: DNA
<213> ORGANISM: Homo sapiens

<400> SEQUENCE: 9
ctaaaaacaa acaaagccaa aaaaccatag cactttattt taaggatatt tctactttaa    60
tccataaatg gtttctagtt cttgtattaa tggcgacatc atgttccatg ttttcatgaa   120
ctgtgattta tcagagaagc ccttgcaacg gtgatctagg ttgtgtcatc gcttctgcgt   180
aacagcaagg caaagctgcg gatttatcgc cgttctaccc aggtttcctg ttgattacgg   240
cagggtttga ggtgcggtcc ctggtgtttc atcatgacaa gtggaggttt gcaggagaac   300
ttcataacca tctgcagaaa aggtgaagtc acatcttgag accagctcta gatatgttac   360
```

```
cgatgggcta atggttttga tgtaaaataa gtaaaaacat taaagggcta gaagaagcca    420
gaggaaaagt ca                                                        432

<210> SEQ ID NO 10
<211> LENGTH: 199
<212> TYPE: DNA
<213> ORGANISM: Homo sapiens

<400> SEQUENCE: 10
gtgaaataag acacacacag aaagaaaaat atgatatgat atcggttgta tgtggagtct     60
tgaaaaaaat caccatagaa acagtgtagg aagatggtta ccaggggcgg ggtaggggaa    120
atgggaagat gtaggtcaaa aggtacgaag ttgcggttag attctaatgt tctagtgtgt    180
aacataagga ctatagtta                                                 199

<210> SEQ ID NO 11
<211> LENGTH: 580
<212> TYPE: DNA
<213> ORGANISM: Homo sapiens

<400> SEQUENCE: 11
gcacattcat ctctctgaga aacacctccc tatgctggga aatgtgaaag caggtgggac     60
accagtcatc ttagtacatc acattgtcac tgccgcgaat gtgtgggaca cccatcatct    120
taccacatca catcgtcact gccgcgaacg tgtgggacac ccatcatctt accacatcac    180
atcgtcactg ccacgaacgt gtgggacacc catcatctta ccacatcaca tcgtcactgc    240
cgcgaacgtg tgggacaccc atcatcttac cacatcacat cgtcactgcc gcgaacgtgt    300
gggacaccca tcatcttacc acatcacatc gtcactgccg cgaacgtgtg gacacccat    360 catcttacca catcacatcg tcactgcgtg aatgttttc tgaatacatc acacatttgg     420
ctccataaaa tctgttttct aatctacttt ttaacttagt atgttggcct caactttgca    480
ctttattttt cttcgtgact gtgtggtgct ctcctctctg gaggtgcctt cactgaggct    540
gcattgaagg gctgtgtggg ccagcgagtg ctgtggtcgg                          580

<210> SEQ ID NO 12
<211> LENGTH: 539
<212> TYPE: DNA
<213> ORGANISM: Homo sapiens

<400> SEQUENCE: 12
ctcttcattg accctgagtt tgaccaggtt tggccaatag aagtcagagg aagtgacagg     60
tgccagttac aagaagttcc acaacccctt ttagaaatca actaaccac tgtgtgaata    120 aagccaggtt agcctgctgg agaatgaggc ccaattgctc ccatcatctc acatgacagc    180
caaccaacca ccagtcatgt gactgaggtc atcttggacc agccaaattc caaccaacct    240
tttcagtaga cctcagacac atgaacaaac ccaactaaga tcaaccaacc ctagacagtt    300
ctgcagagtt gcccagtaac acacagaatc atgaccaata ataaatgtgt actgtttgaa    360
gttgccacat tgttaagtgg tttgttatgc cacaaaaact aactgacaca tcaactctga    420
aacctccttg gttaatcagg gtgctggca ggtacgagc aactgtgccc agggtaacat     480
tacttagtct cagaatcata attaattaaa ttgcaagtga cagaaatata ataaaatct    539

<210> SEQ ID NO 13
<211> LENGTH: 591
<212> TYPE: DNA
```

<213> ORGANISM: Homo sapiens

<400> SEQUENCE: 13

```
tgattttaag tgaaaggttt ctgaactgta tatatacaat atttcagaac agtaatttcc      60
tttgcttcat agtacggcac aacagtgttt gcacttgatg tttagcgtag ccttggtttt     120
ggttgttcag aagcctttgt tagctctttg gttgtgccaa gaatatattg ttttttgagtc    180
tccttgccgg gcctcctcgc cttcttgtca tgcacatcct gtacctgggt tgtggttgta     240
ttgatttgct ggggcgctgc tgttgcaaat gtctggagtg aatgagaatg tgtttgtggg     300
tgtctgccct caccttggcc actgatctgc tttcagccct gaagtactgc catctgcatg     360
aacattaggg accccccagcc tcccccacca cttagtaaag taccctgcac atgtttggga    420
ttcaggaaat gtttgtagaa aggaaaaatt ccttatcatt ccttaccatt ctctgtcttg     480
agtctgagtc atgattcaaa cacttttgct aaaaggtttt cgcttgaaaa attcatattc     540
aggtacagat ttactttttt ttggtgtgtg tgagtttaag agctgcctca g              591
```

<210> SEQ ID NO 14
<211> LENGTH: 608
<212> TYPE: DNA
<213> ORGANISM: Homo sapiens

<400> SEQUENCE: 14

```
atcagaagtt gcgtgggtca tgaagcccaa ggccagcagt tctggatgcc tccatgaagc      60
tggatattgc ttacttgtta gcatccctct ctggcaatca tcaataacct cttttcaaaa     120
gtacctcctt atacaagact cttatcaact gatttcatca ttttttagcac tgaaaccttg    180
gtcttcctgc tctctgctct gacagcatct ctctgataac ctgagaaatc agagtttcac    240
ccctgaaaact aaacaggcca ttatttccta attttaaatg atgacatgac aagccttcac    300
cctatctgtt tcttatttcc ttgaactctc ccaccctcac cagcagccaa cacaaatcac    360
aacgcaatgc aaaggccagg ccacagaaca cgctgtgaat cgacagtttc agaagacgtc    420
attcacacaa tgtgcaaggc acttcctgca cagccatctc tgtgcccctg caaagggcat    480
gtggcatgag gcagtaaaat aagtatagtc tgtgtttggg tatgaaaggt ggtgggtggg    540
gcgtgaatac atccaagata tgctttagga ctaagtcaaa agagaactga gagtgagaaa    600
gaagattg                                                               608
```

<210> SEQ ID NO 15
<211> LENGTH: 392
<212> TYPE: DNA
<213> ORGANISM: Homo sapiens

<400> SEQUENCE: 15

```
tgggcatggt ggctcatacc tgtaatccta gcactttggg aggctgaggc aggtggatca      60
cttgaggtca ggagctccag accagcctgc ccaacatgca ttgcatccat agcttggctg     120
actttcttaa aaaacaggtt gatggcaaga aaagagaact gagtagatgt tataaatagt     180
taagtacaaa tctatcacta cttcttgcga aaatgctcag gctgccacac tgatgatgaa    240
tagatagctc gttcttccca aactgagtgc agtagagtgt tgcagtgctc agttgggtag    300
gacagatgtt ggataattgg ggttatccaa catctctact aaaaatacaa aaattagctg     360
tgcgtggtgg aaggtgcctg taatcccagc ta                                    392
```

<210> SEQ ID NO 16
<211> LENGTH: 305

<212> TYPE: DNA
<213> ORGANISM: Homo sapiens

<400> SEQUENCE: 16

```
aaggaggaat tgctgtctga gagggtattt tgttccccag tgactgaggg cagggcaggg      60
gcagggaagg cttcccctct cttctggccc tagaggccct gtaaatgcac tgtgcagtca     120
ctgacgtgcc ctcaggcagg gccctggcgg aagggggct gttccaggtc taccagcttc      180
acacccttat tctattgaat tctcatgaaa acaaaatctg tgaaacagct gtgatcttca     240
ttttctgatg agggaacaga gcctccgtgc ccccgagatc actggtatga ctccaaagat     300
tttcc                                                                  305
```

<210> SEQ ID NO 17
<211> LENGTH: 433
<212> TYPE: DNA
<213> ORGANISM: Homo sapiens

<400> SEQUENCE: 17

```
gactcacacc tttggccact gacccctgcc ccaccttctg agtggggttc agggactgtg      60
ctgagtctgt ctctgggaag cagcagggtg caggggcaca ctgatgagtg gtgcatgtgc     120
ccagggcaa catcagagcc gtttagccac cagggcagtc aggcatggac agacgcattt      180
gggaggggc gggccctgt gtcagctgtt aacacttcag ttcctgaagc agagaagtct       240
ggagttctgg ggaggggcca gggaggcagg agagggaaac actgggaggg tttagggctt     300
ggcctgttta tcaactactg tggaagtatt ttcactgttc tgacaatccc tgcaactatg     360
tccatggacc tgctgtctat ccgccctgtt catcgggagg aagagatgga gaaggctgcc     420
ggggttctgg gag                                                         433
```

<210> SEQ ID NO 18
<211> LENGTH: 695
<212> TYPE: DNA
<213> ORGANISM: Homo sapiens

<400> SEQUENCE: 18

```
ccaaccccc ttccccaccc caaactctgc ttataggttc ttatatgata atttaaacta      60
tatatgatat taaattagca ctccaatagc aaaaataaag tgttcccaca tcaccttctt    120
tgaaatatt tatttaaata ggatgaaatg ttattgaggg cttttgtgtc tagaaacagg      180
gttaattaaa gatttcctgc ctgctttgtg ggtaggtgac actctcattg agatagcagc    240
aatgccctat ttagtggtct ctcagctttc tttctattca tctggtttgg tagtggaatt    300
ccatgggaag tttgacccta ttcagtgatg agagaagcaa aatactgttg ttcacctaga    360
ggctgtttgc tcagaaaaac agggtgtcag agacatggga cgcaaaccca gagtgacata    420
gcgcagggac ttggctcact tttctgagat ctgtaaaatg tgatgtgact ggctctcaga    480
aaggaggctg aagggttcct gcccgattgg ttttcaaagg gcaagagccc cgctgctgag    540
gagctgcggc tttgttagac aaaagcccag ggcagccccc tcctgggctc agcgttttcc    600
ccacctcccc ctttctcaca ggcggtttcc ctgaaatgaa agaactgtga tgcatttgcg    660
ccttcaaaag cagttttaa aatgcattaa accca                                 695
```

<210> SEQ ID NO 19
<211> LENGTH: 383
<212> TYPE: DNA
<213> ORGANISM: Homo sapiens

<400> SEQUENCE: 19

```
tagcagggag gggaattttc ctttctggtc acgtaggctg ctgtcttcgg cttcgattcg      60
taagccacct cccaagcccc cattagcccc aggtagggga catcccatcc ccctaaacct     120
ccttcttgaa ctgacagttc acccctagaa ggaggtggga aaccactcag atccatctca     180
aagggatgcc taccagggta ggtgtgtggg aggaaggctg agcccatgct gtgttcaggg     240
gccccccag aaggtgtcag cctggaggaa catgccccac agttataaaa ggcatcattc      300
caggagctat catggcgtct gctaggggca gagaggaagg ggaggcagga aaggggctga     360
gtattttggg gctgtatgct tat                                             383
```

<210> SEQ ID NO 20
<211> LENGTH: 364
<212> TYPE: DNA
<213> ORGANISM: Homo sapiens

<400> SEQUENCE: 20

```
ggcctttcct ccggggagac tgtggaggtg tcccctcagg cagcaaaagc accatcgcag      60
ccctcggtgt caaggcctct ctgagtcgcg ctttgcctta ccgtacctcg tttctgggct     120
aggatatttt gaaacacttt tgtctattag ctttatctaa aatagctaaa atatcagtct     180
ccatagaggc aaagtaagtg gcactgagaa gcaaaaaatc cagccaatgt gcagttttct     240
cctcctgccc cctatttgtg gaaatgaggc acggccccca tcttgtctgc tgggtggggt     300
tctgtttacc acgcttggca gccaccgcca cccaacaatc tttcattttt ctttctaact     360
tcac                                                                  364
```

<210> SEQ ID NO 21
<211> LENGTH: 495
<212> TYPE: DNA
<213> ORGANISM: Homo sapiens

<400> SEQUENCE: 21

```
gagctccctg gtgtggtgtc tcaagcctga agctcagagg ctggagctat tgcccctggc      60
tgtctcccct gaagtcacta aattccagcg ttctgggtcc ccttgtcccc agcacacaag     120
gatgggctgc tctgagcaag ctcaggcacc ctcactctgc cacactgtgt gtgtgactta     180
gaccccacaa ggcttttctg agaaaacagc tgtgacctga cagaaacccc tgcagctgca     240
cgggcctcag aatcccccga ggcgctggcc cgggctgtgc ctggctccct ggtgggagca     300
gaagtgccca tggcctctcc tgccctccca acagggcccc taaacaaatt cccacaccca     360
ggtgagttac caggagcgat caggtgggcc gaggacattt gcttgcttca ccttccctgt     420
ttctttagat tgaaattcag cctgccccac ttctcaggaa gatgccacga ggctgatccc     480
cctgagcagt ttgtc                                                      495
```

<210> SEQ ID NO 22
<211> LENGTH: 418
<212> TYPE: DNA
<213> ORGANISM: Homo sapiens

<400> SEQUENCE: 22

```
tggctggcaa tcctttttag ccatcatata taatagctat ctaactcttg attttgtgt       60
aacataaagc ggtgtttcat aatgaatcat tttgtctgtt cgtgttcaag tgccctatct     120
attctatcat ttgaaaagct agttatgata gtatggtttc aattgtcaga cattctcttt     180
attctaaaaa aataggttga cccacattta gatgttttcc tactcaaagg actttgaaag     240
```

```
aacttttat gtaacactta gtcattgccc ttttcacagt ccctcttccg ctgcttctaa      300
ttaggctctt tggtagctgg aatcgtcatt tccctggcat gaaggcacat ggtaccaact      360
tgttggttgc ttgatttgga gggtcaaata tggacttgct tcttttggtc taccttgc       418
```

<210> SEQ ID NO 23
<211> LENGTH: 303
<212> TYPE: DNA
<213> ORGANISM: Homo sapiens

<400> SEQUENCE: 23

```
ctgacaagat gcaagctcat cattttgttt tgtgtcataa gggcatttgc ctactaatta      60
gcgttttgga aaacttcccc aataatgggg cccacagtct ctaacactgc cccctttgaag     120 ctagtgatcc aaaaataata tcatttgaca aggtaatttc ccaagccacg cctgaaatgt      180
aaaacaaaaa aagcacctca ctgcttaaag gtgctccacc agggaccttg ggttttccac      240
caaaacttgc ctcccccacc ctgttactaa agttgacact gaatttgcct gcagtctccc      300
cca                                                                    303
```

<210> SEQ ID NO 24
<211> LENGTH: 183
<212> TYPE: DNA
<213> ORGANISM: Homo sapiens

<400> SEQUENCE: 24

```
tgagctgtcg cccttgggta caccagtagc aaaaacactc ctgtcctcct atgctgctgt      60
gacaccacac cccacttcct cccgcgggcg tgtgacactt ttcaaagaaa atacagtatt     120
tggtagtatc aatacagcaa gcggaagcag cagtgctcag tccgcagtga gctaacagtt     180
tta                                                                    183
```

<210> SEQ ID NO 25
<211> LENGTH: 258
<212> TYPE: DNA
<213> ORGANISM: Homo sapiens

<400> SEQUENCE: 25

```
cagacataca gtactatttt gttttttta aaaaaggctt agtaaacaca aagaggagtt        60
acatactgaa acccacagct gatttaattt gcaaaaccac agcgttagct tgactaaagt     120
aaagatgaca cagataaaat gcaaccagaa aactgagata aagatacag gataaataac      180 ttaagctgat ggtttagcaa gcaaacatca tgggtgtaac atgaagatct gagaagtgac     240
ttcggtccag gaaactca                                                    258
```

<210> SEQ ID NO 26
<211> LENGTH: 278
<212> TYPE: DNA
<213> ORGANISM: Homo sapiens

<400> SEQUENCE: 26

```
ctaaaaatta caccttctgc tcactctaat ttattgctgt agaagaaaga ataagtgaga      60
tatttccatt tctagtgaca ggtggctggc actttgaaac cttccatttc attactcacc    120
ttaatgtttt cactaaaaca catgtggttt tcaaacacag gaaggaaaac atggtaacct    180
gtggttacaa tttccactag aaaatagaaa aggtgtaggt cagaaagaat gtttgtgggg    240
tgttcctttt ttactttaaa catgaaaacc catgtcag                              278
```

<210> SEQ ID NO 27
<211> LENGTH: 140
<212> TYPE: DNA
<213> ORGANISM: Homo sapiens

<400> SEQUENCE: 27
ttaagagaaa aaaaaaacac ccatttatgt gaccagtatt gtctgtcttt tttttaatcc      60
aataaaactt tcaactacaa tcggtgctga tgtcaccatg ttagcggcac acactcttga     120
ctctggtttg cacagttcac                                                140

<210> SEQ ID NO 28
<211> LENGTH: 192
<212> TYPE: DNA
<213> ORGANISM: Homo sapiens

<400> SEQUENCE: 28
cggcggagga gggaaagccg agcgccagga aaagctccta tttgcagcac acctacccc      60 accgtgtgcc aggcactcat cataaatgtc acaatgacag atgaggaaac cgcggctcag    120
aaggtcaagt ggctgccgga ggctggcagg gagcagggtg gggctctgac tcgggctgtg    180
ttctttccca ca                                                        192

<210> SEQ ID NO 29
<211> LENGTH: 528
<212> TYPE: DNA
<213> ORGANISM: Homo sapiens

<400> SEQUENCE: 29
tgaaaaccac agaggaacgg cgagaaggaa tgggagggag gaaaatacat tccgtggcag     60
tgaagttatt gaagtgccag agccaaagaa cagataattt aaggaaaaaa ttctgtggca    120
tctcccatcc tacacataaa tcactgttct ctattttctg aacacgagcc tatgcagggc    180
ctaggagagt ccatgtgtga aactgaatac agaatatacg acgatgtaag acgtacaacg    240
cgcacgtatg aactatgtgt gaataggtag cgacgtaggt atcgctgaga agagaaacta    300
caatttgaga tcccacctgt ggttacagaa aagcagacag agccctcgat gaattaaatg    360
cagaatgcat cagaaatgtg gcagtacaga aacgccccgc agacgaggaa atcctaaatc    420
tgttgtctgc atctctctaa gaaaagaac ctacaaggta aagaaacagt cctcacaaag     480
ccggtcccag aaaccattaa ttacacttta gaaagaaata ggagttta                 528

<210> SEQ ID NO 30
<211> LENGTH: 897
<212> TYPE: DNA
<213> ORGANISM: Homo sapiens

<400> SEQUENCE: 30
aatttcaaac tcattttcta attcaaaaga aacacagatg aatttaaaaa ttagcagagg     60
tcacacgtgc ctgttcgcaa gcacccctcc tcctcagctt cgtcttttgc caagactatg    120
taccagcact ttttcctttc tctcctcttt tttttatttt tttattttttg gtaacatctg   180 gtattctttc ctttttttgg cagtctctgc cttttcactt tcctcatgca gcagccctgc    240 gagccccgt aattgagttt gaaggtgtcc aaagccgttt gctgtgctgc agctctgatt     300
tctgcgtcaa gtcctaacag ccaaccaacc tgggagccag gcctgttgg cgtcccgag      360 acagccccgg gattatccag gcctccaggg ctcagttctg agctgggatc tccacgtccc    420
agaccagaga tccaactcac tgcctctaag ggagtctggg aggaaaagaa acaaacaaaa    480

```
aatatctcct tcccctccca ctttcagcgt tgaaagttaa accccctgaga tgacagggtg    540 ttcacccgat tccaaagaac ggggtttcct ctccccacca cccaggctgt ggcgctgtgc    600
cttggcctgc tgtgtgcgac acttcccagg aaggtagcaa ggtcaccctc aacatcaggc    660
agcagagtca cccccagccc caaatttctg ggtcagagta agtggaccaa gtgggcctga    720
aagctcacgt tcaaggcctt tgtagacacc cccaaagact gtggtttcac ttccgctggc    780
aggcagatac caagctaggc gtgtagggtg cctgcatatg tgtgcatgtg tccctcctta    840
gaactgtatc gataatggaa gaaataaaag gagaaagcca agccctggga agggcaa      897
```

```
<210> SEQ ID NO 31
<211> LENGTH: 526
<212> TYPE: DNA
<213> ORGANISM: Homo sapiens

<400> SEQUENCE: 31
tggctcctat gctgggtttt caggggaggg gagaaccact ttatatattt atttatttat    60
ttaaattttt taaaatataa cataaatatt cggctctcgg ccgcccggca gccagtcctc   120
tgcggtgact gggcgcgcag ccctctcgag ctccgcgcgg gcagcccggc cccagcccgg   180
cgaggtgcgc ggcggattgc aagcatataa cctgcccgcg gtctcgatgg cacccagagg   240
atgttttatt tctattgcag ttaaaaaaaa aaaaaaaaa aaaaaaaaa aaaaaagga     300 acggcgaccc aggcaccgcg agagaaagaa cggcggggaa atgttcgcgc gcagcgaaga   360
agccgccccg cgggctgcgg cgggcgggga gcgccgcaaa gccaccttcc cggtgcaagt   420
gtgcggggac tcgggcgggg ttcccctgca aacaccgtac ctggcccgct cgcgctcgct   480
tttcccctct gctaaataaa cccaacaggg acggtggaag ctgctg                526
```

```
<210> SEQ ID NO 32
<211> LENGTH: 189
<212> TYPE: DNA
<213> ORGANISM: Homo sapiens

<400> SEQUENCE: 32
cagctagtgg gtggtggatc cgtgctcttg accaccccac tctgttgcct ttctgttaga    60
caacaccttg tctactttct cttccccatt tcacagatga ggagacagga ccggaactgt   120
gaggacaatc tgtctatagt taggcagtga gctgactgca gactcaggct ctcctgggac   180
cctcttcag                                                         189
```

```
<210> SEQ ID NO 33
<211> LENGTH: 438
<212> TYPE: DNA
<213> ORGANISM: Homo sapiens

<400> SEQUENCE: 33
gcaaaaaggc aggggctgca ggggacttta taaagttgtg ctgtctgggc tgaaggcttg    60
cagacaggaa gcttgggtgc aggtgggctg tgagctgaat gcttgcaaca ggatgtttgg   120
gtgctagtga gctgtttgct gttgacccta tttctcagaa cattcactcc cctctacccc   180
tgtgtctgtt cttgccagct aagctcattt ccaatttttct tttagctcct tagggctcca   240
catgcgtgac ttattagagg agcaaaagaa gccgaatatg gaaggggaaa gccttggcct   300
gatccagggt gctctagaac aaattcctcc cactgaactg tcctgctgtg gggcaagcag   360
```
gtgagcactt gttctgttgt cagtcaccat ttgccccggg gtggggtgt aacctgccag    420 gcatcctcaa gggatgca                                                 438

<210> SEQ ID NO 34
<211> LENGTH: 301
<212> TYPE: DNA
<213> ORGANISM: Homo sapiens

<400> SEQUENCE: 34
cccccaggct ggtatttcag tgacactctt agtctgttgt tgtcccaaat gctgcgtacc    60
tgaaagaaag agcacccctt ttgaggcatc aagacttgat tcagtctcag ttctgagact   120
gaatcaacaa ctttcaacag gtgaataata agaacctcag aaacctgcgc tgacgccctc   180
agaagctggt ttcccgtcct ctgtggaagt ggatttagaa gccagttgag cagccatgtg   240
accttgaaca agtcacttct gtgttctgca ctgtgagctc tattccactg ccccctttct   300
a                                                                  301

<210> SEQ ID NO 35
<211> LENGTH: 342
<212> TYPE: DNA
<213> ORGANISM: Homo sapiens

<400> SEQUENCE: 35
tgaacccaag actctacaac atcctggcct cgattttttgg tccagctctg gttggttctt    60
tctgtgttat tctgttctgc tcctcaattc ctctcccctc cctccccct cctctcccca   120 ccccttcccc caccccctcc cctccccctc ttctgtcacc ttgcactgtg cactttaatg   180
cacattgcac tatgtcaagg tactaacttt gacaactgct ctcataattc caaccacatt   240
caggctgagg gttgcagctt ggctccccct cactcttctc accttcacca cacaggacat   300
tggctgtgca cagccacttg tttattgcag ctggagacca ca                     342

<210> SEQ ID NO 36
<211> LENGTH: 99
<212> TYPE: DNA
<213> ORGANISM: Homo sapiens

<400> SEQUENCE: 36
cttgctggct ctcctcggtg gcttcctctt gaatgaacct ttcttctgaa ggcttgattt    60
ccttccggga ggcttagtgt ttctgctcag ccttctttc                          99

<210> SEQ ID NO 37
<211> LENGTH: 658
<212> TYPE: DNA
<213> ORGANISM: Homo sapiens

<400> SEQUENCE: 37
tctgtcactc cctcgttgcg gactcctatg taggtcgcct ggtgtgggga gaagcattct    60
ttgtggtatt cggttgggta gaagccaatc acagcttcca cctacactca aggggaggga   120
gttgtacagg gtgtaagcaa tttggggagt caccttagaa ttctgcccac cacagtacct   180
ttctggttat ttcatggact tccgttccca gaaaatctga gcgtttgcgt cctaggaaga   240
ctggtgagag cagccccagt ggaggaataa aaactaagat ctggaaaatc agcagtgggt   300
tgttttcatc tctcagcagg caggaaacag gaggagaaag gaatgtctgt aggctcccaa   360
cactgatggg aaggaggtgt ttggctgggg tagagctccg caggaatctc ccaggctcct   420

```
ctagctaggt gcagccgtgt tttatccggc tgtctttaca tgggctgatc actcaggagt      480
ggcatatggc aggagcacgc tttggggtac gagcctcctg gagaatgaac tgcagcacac      540
aagccagaca gatggtggct tagtccccct tggacaagag tgtgtcctgc acactggagg      600
gcggggtgct gagaggcgct tgtggtgtct gaggccgagc tttgctgagt tcacctga       658

<210> SEQ ID NO 38
<211> LENGTH: 351
<212> TYPE: DNA
<213> ORGANISM: Homo sapiens

<400> SEQUENCE: 38
tgaaagaaag agaataaagc actgggcttt gcaaactagg ctaaggcccc aaaccacaag      60
attatcttga tgcatgtgat tgggaaggag gactaattag aagagaggat gtcattttat     120
tttctaacca gccctctctg atctgaagcc atgcaccccc ctcacttgtt acctagcaac     180
ccttctttgt atatgtaagg ttacttcatt cctgcattgt tattcaattt atttgccatt     240
ttaagtgtct tgatcctctc taggatcacc ctggtgtgat tggctggcat tagtctctaa     300
aataccggag ggcagtctat taagtggatc caaatgtcat tgtacagctc a               351

<210> SEQ ID NO 39
<211> LENGTH: 153
<212> TYPE: DNA
<213> ORGANISM: Homo sapiens

<400> SEQUENCE: 39
ctgagatgtt cgtagtattg tcatctacat ttcatagaag aagaaactga aacaggttag      60
gtaacttact cgtggtcaca gaggtaattg gtggatttga ggattcacag gattctaaaa     120
tcgagttgct gcactgcctt ctttaaaaaa tta                                   153

<210> SEQ ID NO 40
<211> LENGTH: 210
<212> TYPE: DNA
<213> ORGANISM: Homo sapiens

<400> SEQUENCE: 40
tgtcagccag tggggtggca gccccttttgt acagagcacc atggggggttg gggtggggag     60 gataaggcaa catgtcaaac ccatcaagga ggctttgtga ccccagtgat attttttgca     120
gaacgtggtg gattttcgat gtgaccacaa tgacatccgc cttgcagtgg cagaacagat     180
gcaattgcac aagttctgga gaaactttct                                      210

<210> SEQ ID NO 41
<211> LENGTH: 154
<212> TYPE: DNA
<213> ORGANISM: Homo sapiens

<400> SEQUENCE: 41
tgctctctgc ttaccaaact cctctcccct aagacccagc tcaagcatct ccttcctgtg      60
gggtttagct ccttcccccct cccactccca gacagtacag accacatcct tctcttctct    120
gtgtcacccg gaccttgggt atctgcagac tgga                                 154

<210> SEQ ID NO 42
<211> LENGTH: 165
<212> TYPE: DNA
<213> ORGANISM: Homo sapiens
```

<400> SEQUENCE: 42

```
taacttaagc gtgttggtat ctctgttagt ggtgaagtcg ctgcaaacc acaaaacacc      60 tgactgctac ggaagatatt aacagggact ttttccttc tgcataacag gaagtcttga     120
gtaggtagtc gaggttgggt agaggacact tctgtttcaa ttcta                    165
```

<210> SEQ ID NO 43
<211> LENGTH: 391
<212> TYPE: DNA
<213> ORGANISM: Homo sapiens

<400> SEQUENCE: 43

```
gcattgctca gaattgctcg actttgatta taattatcct acgatcgata aggatccagg     60
tgtacgtaac ataacactgt atcacattat ttaaatcagg tccttttcat taagctgtgt    120
ctgttggtgc tggctagttt attggtgtgt gtgggtgtgt gggggtgtgt gtgtgtgtgt    180
gttagaaact tgtaactata gtttcagttt tctggcctat tatattccta ctgtctttgt    240
atgtttgttt tgtatgattc ttattatttt caccagaagc ggaaacccctt tttaagctga   300 aaaaggatga ttcatttcgt acacagtgag ggccctctta ccttatttat ttgctcacat    360
attaatagag gagacagttt ttcatgcagt g                                    391
```

<210> SEQ ID NO 44
<211> LENGTH: 281
<212> TYPE: DNA
<213> ORGANISM: Homo sapiens

<400> SEQUENCE: 44

```
ttctgcatga gcaggccccg ctgaaaagga aggcggctcg ccagatttgt ttcgaattat     60
gaaaatagat gttgtctccc caccacatct gttttgcctg acaaatgagc agcagctcgc    120
ctcctaaata aggcagcaca ccaagacggt cttgaaactc cggcttctcc aactcttcag    180
aaaaggagaa gaagaagaaa aaagagtcca agcctcccag gtttgagctc taaaagccag    240
acctttttca atgtcatctc tcacgccgca gtctccgggg g                        281
```

<210> SEQ ID NO 45
<211> LENGTH: 118
<212> TYPE: DNA
<213> ORGANISM: Homo sapiens

<400> SEQUENCE: 45

```
tattaacaag tttgtggtaa ggtgttatga caatgataga aaactaatac acggggattt     60
cccaagactc tcaagtgatt gttcatttc cttttaggtt cttttttttt tttttga       118
```

<210> SEQ ID NO 46
<211> LENGTH: 500
<212> TYPE: DNA
<213> ORGANISM: Homo sapiens

<400> SEQUENCE: 46

```
gccggctctg tcgtcgaggc gctcacaggc aggcacacgt gagctcctgg aggacaggga     60
gagcggccgc cccgcccctg cggagcacag acgcttcct gccaccctg cagagcatgg     120 gacgcttcct gccatggtgc cgtggcaatg ggtggcacct gcctgtggcc ccttctcaga    180
aggacgtttt aaacgcgtga ggtctgatgc acagccacag ggagacacag acgagcagat    240
gtgggcatcc gagtatttac aaggtctggt ggctcctgca gccgcgacac gggctgagcg    300
```

| | |
|---|---|
| caagtgatgt gtgaggtgtc cccaacagat ggcacgggga gcgcccacac ccgccaccgc | 360 |
| ggggtctgcg gaagctcgtg tcagctggag gttagggaag acgcacaggg gctcattctc | 420 |
| cacccaggtt caaactccct gaactcacga gacccaggct gaagacatgg acagactccc | 480 |
| agccccagcg cccctctgac | 500 |

<210> SEQ ID NO 47
<211> LENGTH: 155
<212> TYPE: DNA
<213> ORGANISM: Homo sapiens

<400> SEQUENCE: 47

| | |
|---|---|
| ctgactgata aagaaaaac aaattttcct tcaaggcagt atgataacaa tctcttaacc | 60 |
| actgggagga atgtttatga cattcatctc tgagctgtga actgccaaaa tgaggcacgc | 120 |
| ctagcaacat aacctggccg accctaggcc gcgag | 155 |

<210> SEQ ID NO 48
<211> LENGTH: 81
<212> TYPE: DNA
<213> ORGANISM: Homo sapiens

<400> SEQUENCE: 48

| | |
|---|---|
| gtacttatat aaggggtgg gggcgcgttc gtcctcagtc gcgatcgaac actcgagccg | 60 |
| agcagacgtg cctacggacc g | 81 |

<210> SEQ ID NO 49
<211> LENGTH: 76
<212> TYPE: DNA
<213> ORGANISM: Homo sapiens

<400> SEQUENCE: 49

| | |
|---|---|
| caacaaaatg tcgtaacaag ggcggtaggc gtgtacggtg ggaggtctat ataagcagag | 60 |
| ctcgtttagt gaaccg | 76 |

<210> SEQ ID NO 50
<211> LENGTH: 31
<212> TYPE: DNA
<213> ORGANISM: Homo sapiens

<400> SEQUENCE: 50

| | |
|---|---|
| agagggtata taatggaagc tcgacttcca g | 31 |

<210> SEQ ID NO 51
<211> LENGTH: 63
<212> TYPE: DNA
<213> ORGANISM: Homo sapiens

<400> SEQUENCE: 51

| | |
|---|---|
| ttcgcatatt aaggtgacgc gtgtggcctc gaacaccgag cgaccctgca gcgacccgct | 60 |
| taa | 63 |

<210> SEQ ID NO 52
<211> LENGTH: 203
<212> TYPE: DNA
<213> ORGANISM: Homo sapiens

<400> SEQUENCE: 52

| | |
|---|---|
| tgcatctcaa ttagtcagca accatagtcc cgcccctaac tccgcccatc ccgcccctaa | 60 |
| ctccgcccag ttccgcccat tctccgcccc atcgctgact aatttttttt atttatgcag | 120 | aggccgaggc cgcctcggcc tctgagctat tccagaagta gtgaggaggc ttttttggag    180 gcctaggctt ttgcaaaaag ctt    203

<210> SEQ ID NO 53
<211> LENGTH: 41
<212> TYPE: DNA
<213> ORGANISM: Homo sapiens

<400> SEQUENCE: 53 gggggctat aaaaggggt ggggcgttc gtcctcactc t    41

<210> SEQ ID NO 54
<211> LENGTH: 178
<212> TYPE: DNA
<213> ORGANISM: Homo sapiens

<400> SEQUENCE: 54
ctgacaaatt cagtataaaa gcttggggct ggggccgagc actggggact ttgagggtgg    60
ccaggccagc gtaggaggcc agcgtaggat cctgctggga gcggggaact gagggaagcg    120
acgccgagaa agcaggcgta ccacggaggg agagaaaagc tccggaagcc cagcagcg    178

<210> SEQ ID NO 55
<211> LENGTH: 25
<212> TYPE: DNA
<213> ORGANISM: Homo sapiens

<400> SEQUENCE: 55
tctagagggt atataatggg ggcca    25

<210> SEQ ID NO 56
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 56
tattcagcgg ccgcacctgg gtcagtgcgt ca    32

<210> SEQ ID NO 57
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 57
gtacgaattc gagagcacca cacagtca    28

<210> SEQ ID NO 58
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 58
gcgactagtt gccagcaccc tgattaaa    28

<210> SEQ ID NO 59
<211> LENGTH: 36
<212> TYPE: DNA

<213> ORGANISM: Artificial Sequence
<220> FEATURE:
<223> OTHER INFORMATION: Synthetic oligonucleotide

<400> SEQUENCE: 59
cgcgcgaatt caccatactg gtatattcat tctctc                                36

<210> SEQ ID NO 60
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 60
ggccgctgac ttagtcctaa agcatatctt gg                                    32

<210> SEQ ID NO 61
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 61
acggcaatct tggtaccctc cagtgccaga tttttcaggg                            40

<210> SEQ ID NO 62
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 62
catgcgggta ccagtacgac tagtgaactg gctgggctat tttgtgc                    47

<210> SEQ ID NO 63
<211> LENGTH: 50
<212> TYPE: DNA
<213> ORGANISM: Homo sapiens

<400> SEQUENCE: 63
ggtgtggagg gccgggtggt gacrctsagt gacaggtgag gatgtggcay                 50

<210> SEQ ID NO 64
<211> LENGTH: 50
<212> TYPE: DNA
<213> ORGANISM: Homo sapiens

<400> SEQUENCE: 64
cggtgtggag gccgggtgg tgacgctgag tgacaggtga ggatgtggca                  50

<210> SEQ ID NO 65
<211> LENGTH: 41
<212> TYPE: DNA
<213> ORGANISM: Homo sapiens

<400> SEQUENCE: 65
gtgggacacc catcatctta ccacatcaca tcgtcactgc c                          41

<210> SEQ ID NO 66
<211> LENGTH: 21
<212> TYPE: DNA
<213> ORGANISM: Homo sapiens

```
<400> SEQUENCE: 66
yscctycccc wccycytycc h                                              21

<210> SEQ ID NO 67
<211> LENGTH: 15
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is a, c, g, or t

<400> SEQUENCE: 67
aaaadaaana aarwa                                                     15

<210> SEQ ID NO 68
<211> LENGTH: 20
<212> TYPE: DNA
<213> ORGANISM: Homo sapiens

<400> SEQUENCE: 68
ytggkggshr ggsgkstgtg                                                20

<210> SEQ ID NO 69
<211> LENGTH: 45
<212> TYPE: DNA
<213> ORGANISM: Homo sapiens
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 69
ctcvgvscdg gndgcchggc hmanvccggg ccwgbbbcgc ggvsg                    45

<210> SEQ ID NO 70
<211> LENGTH: 11
<212> TYPE: DNA
<213> ORGANISM: Homo sapiens

<400> SEQUENCE: 70
tcwstkttct g                                                         11

<210> SEQ ID NO 71
<211> LENGTH: 14
<212> TYPE: DNA
<213> ORGANISM: Homo sapiens

<400> SEQUENCE: 71
gtgdmasgtg cctg                                                      14

<210> SEQ ID NO 72
<211> LENGTH: 21
<212> TYPE: DNA
<213> ORGANISM: Homo sapiens

<400> SEQUENCE: 72
gcagccrccy crckgkctga g                                              21

<210> SEQ ID NO 73
```

```
<211> LENGTH: 29
<212> TYPE: DNA
<213> ORGANISM: Homo sapiens

<400> SEQUENCE: 73
cccctgcrga gcayrggacg cttcctgcc                                              29

<210> SEQ ID NO 74
<211> LENGTH: 15
<212> TYPE: DNA
<213> ORGANISM: Homo sapiens

<400> SEQUENCE: 74
tgkcctctmc ccacm                                                             15

<210> SEQ ID NO 75
<211> LENGTH: 21
<212> TYPE: DNA
<213> ORGANISM: Homo sapiens

<400> SEQUENCE: 75
gccytbhtgt yasrcamaas m                                                      21

<210> SEQ ID NO 76
<211> LENGTH: 37
<212> TYPE: DNA
<213> ORGANISM: Homo sapiens

<400> SEQUENCE: 76
swmtgacacm ctgtgkgtgt gmsyywgmms ycasywg                                     37

<210> SEQ ID NO 77
<211> LENGTH: 21
<212> TYPE: DNA
<213> ORGANISM: Homo sapiens

<400> SEQUENCE: 77
acytkctgcw cwgccttmtt t                                                      21

<210> SEQ ID NO 78
<211> LENGTH: 11
<212> TYPE: DNA
<213> ORGANISM: Homo sapiens

<400> SEQUENCE: 78
cggggagcgc c                                                                 11

<210> SEQ ID NO 79
<211> LENGTH: 19
<212> TYPE: DNA
<213> ORGANISM: Homo sapiens

<400> SEQUENCE: 79
agghagcava gkcaccctc                                                         19

<210> SEQ ID NO 80
<211> LENGTH: 36
<212> TYPE: DNA
<213> ORGANISM: Homo sapiens
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
```

```
<222> LOCATION: (19)..(19)
<223> OTHER INFORMATION: n is a, c, g, or t

<400> SEQUENCE: 80
tbtggcgagb cdccttngnh ttcwgygbgc chcact                              36

<210> SEQ ID NO 81
<211> LENGTH: 11
<212> TYPE: DNA
<213> ORGANISM: Homo sapiens

<400> SEQUENCE: 81
tgtgcccagg g                                                         11

<210> SEQ ID NO 82
<211> LENGTH: 11
<212> TYPE: DNA
<213> ORGANISM: Homo sapiens

<400> SEQUENCE: 82
gaggtgtccc c                                                         11
```